United States Patent
Xu et al.

(10) Patent No.: US 9,909,184 B1
(45) Date of Patent: Mar. 6, 2018

(54) METHODS, COMPOSITIONS, AND DIAGNOSTIC KITS FOR THE DETECTION OF ALPHA AND BETA THALASSEMIA

(71) Applicant: URIT Medical Electronic Co., Ltd., Guilin, Guangxi (CN)

(72) Inventors: Tom Cheng Xu, Castro Valley, CA (US); Jun Liu, Guilin (CN); Chengfeng Jiang, Guilin (CN); Jinlan Xu, Guilin (CN); Lili Sun, Guilin (CN)

(73) Assignee: URIT Medical Electronic Co., Ltd., Guilin (CN)

( * ) Notice: Subject to any disclaimer, the term of this patent is extended or adjusted under 35 U.S.C. 154(b) by 0 days.

(21) Appl. No.: 15/684,281

(22) Filed: Aug. 23, 2017

(30) Foreign Application Priority Data

Aug. 31, 2016 (CN) .......................... 2016 1 0775943

(51) Int. Cl.
*C07H 21/04* (2006.01)
*C12Q 1/68* (2018.01)

(52) U.S. Cl.
CPC ...... *C12Q 1/6883* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,604,350 A | 8/1986 | De Matteis | |
| 5,281,519 A | 1/1994 | Schechter et al. | |
| 5,665,392 A | 9/1997 | Kumar et al. | |
| 5,693,671 A | 12/1997 | Niihara et al. | |
| 5,750,345 A | 5/1998 | Bowie | |
| 5,861,251 A | 1/1999 | Park et al. | |
| 6,322,981 B1 | 11/2001 | Rodgers et al. | |
| 6,372,213 B2 | 4/2002 | Um et al. | |
| 7,572,827 B2 | 8/2009 | Bianchi et al. | |
| 8,563,330 B2 | 10/2013 | Kasinrerk et al. | |
| 8,822,491 B2 | 9/2014 | Shen et al. | |
| 9,347,885 B2 | 5/2016 | Salhi et al. | |
| 9,377,471 B2 | 6/2016 | Hermine et al. | |

OTHER PUBLICATIONS

Bio-Rad Rea-Time PCR Applications Guide.
Luo, Hong-Cheng, et al. "Impact of genotype on endocrinal complications of Children with Alpha-thalassemia in China." *Scientific Reports* 7 (2017).
Randhawa, Gurinder Jit, et al. "Multitarget real-time PCR-based system: monitoring for unauthorized genetically modified events in India." *Journal of agricultural and food chemistry* 62.29 (2014): 7118-7130.
Tang, Wenjun, et al. "Spectrum of α-thalassemia and β-thalassemia mutations in the Guilin Region of southern China." *Clinical biochemistry* 48.16 (2015): 1068-1072.

Primary Examiner — Jeanine A Goldberg
(74) Attorney, Agent, or Firm — Levine Bagade Han LLP

(57) ABSTRACT

Disclosed are methods, compositions, and diagnostic kits for the rapid detection of certain types of α-thalassemia and β-thalassemia. In some embodiments, a diagnostic kit, reagents, and methods are disclosed for the rapid detection of various α-thalassemia and β-thalassemia genotypes in multiple patient samples using real-time PCR. More specifically, in certain embodiments, diagnostic kits, reagents, and methods are disclosed for the rapid detection of up to seven different α-thalassemia genotypes and twenty different β-thalassemia genotypes in one single multiplex real-time PCR reaction.

19 Claims, 16 Drawing Sheets

METHODS, COMPOSITIONS, AND DIAGNOSTIC KITS FOR THE DETECTION OF ALPHA AND BETA THALASSEMIA

CROSS-REFERENCE TO RELATED APPLICATION

This application claims priority under 35 U.S.C. § 119 from Chinese Patent Application No. 201610775943.0, filed on Aug. 31, 2016, the content of which is hereby incorporated by reference in its entirety.

SEQUENCE LISTING

The present application is being filed along with a Sequence Listing in electronic format. The Sequence Listing is provided as a file entitled 05_URTMNZ00100_20170823_sequence_listing.txt, created Aug. 23, 2017, which is 15.9 Kb in size. The information in the electronic format of the Sequence Listing is incorporated herein by reference in its entirety.

TECHNICAL FIELD

The present disclosure relates generally to the field of medical diagnostics; more specifically, to methods, compositions, reagents, and diagnostic kits for the rapid detection of certain types of α-thalassemia and β-thalassemia.

BACKGROUND

Thalassemia is the name given to a group of inherited blood disorders characterized by abnormal hemoglobin production. Hemoglobin is the oxygen-carrying molecule of red blood cells. The dominant hemoglobin in adult humans (hemoglobin A) is comprised of four protein chains (or globins) including two α-chains (or α-globin) and two β-chains (β-globin). Other types of globin in two minor forms of hemoglobin include γ-globin and δ-globin. If a person's body does not produce enough of these protein chains, red blood cells do not form properly resulting in a condition known as anemia, or a deficiency of functional red blood cells.

Thalassemia is usually divided into four types: α, β, δβ and δ. Among them, α and β are the main types of thalassemia. The severity of α-thalassemia and β-thalassemia depends on how many of the four genes coding for α-globin and the two genes coding for β-globin are missing or mutated, respectively. The human α-globin gene cluster is located on the short arm of chromosome 16 (cytogenetic location: 16p13.33) and comprises the HBA1 (α1-globin) and HBA2 (α2-globin) genes. The human β-globin gene cluster is located on the short arm of chromosome 11 (cytogenetic location: lip 15.4) and comprises the HBB gene (β-globin gene).

Thalassemia is more prevalent in tropical and sub-tropical regions. See U.S. Pat. No. 6,322,981, the content of which has been incorporated herein by reference in its entirety, for a further discussion of the prevalence of thalassemia around the world. Thus, those afflicted with thalassemia are often of Asian, African, Mediterranean, or Middle Eastern descent. In China, thalassemia is prevalent in provinces south of the Yangtze river including Guangxi, Guangdong, Guizhou, Hainan, Yunnan, and parts of Sichuan.

Among Chinese patients, α-thalassemia is often caused by α-globin gene deletions such as the large fragment 3.7 kb deletion ($-\alpha^{3.7}$ or –a3.7), the large fragment 4.2 kb deletion ($-\alpha^{4.2}$ or –α4.2), and the multi-gene Southeast Asia-deletion ($--^{SEA}$ or −−SEA) and Thai-deletion ($--^{THAI}$ or −−THAI). See U.S. Pat. No. 5,750,345, the content of which has been incorporated herein by reference in its entirety, for a further discussion on $-\alpha^{3.7}$, $-\alpha^{4.2}$, and $--^{SEA}$ deletions.

In addition, some of the more common α-globin gene point mutations among Chinese α-thalassemia patients include the αConstantSpringα ($\alpha^{CS}\alpha$ or αCSα), αQuongSzeα ($\alpha^{QS}\alpha$ or αQSα), and αWestmeadα ($\alpha^{WS}\alpha$ or αWSα) mutations. The αCSα mutation is caused by a terminator codon mutation of the α2-globin gene which results in reduced α-globin chain synthesis. The αQSα mutation is caused by a mutation of the α2-globin gene whereby the amino acid leucine of codon 125 is substituted by proline. The αWSα mutation is caused by a mutation of the α2-globin gene whereby the amino acid histidine of codon 122 is substituted by glutamine. In all such cases, these mutations result in reduced or defective α-globin chain synthesis.

In addition, β-thalassemia among Chinese patients is often caused by β-globin gene mutations including the following common mutations: (1) a frame-shift codon 41/42 (–TCTT) deletion mutation (also referred to as a 41-42M or a CD41-42M/N mutation), (2) a –28M/N (A-G) (also referred to as a –28M mutation), (3) a CD71/72 (+A) (also referred to as a 71–72M insertion mutation), (4) a CD17 (A-T) (also referred to as a 17M mutation), (5) a BEM/N (also referred to as a βEM mutation), (6) an IVS-2-654 (C-T) (also referred to as a 654M/N or a 654 M mutation). Other less common β-globin mutations include: (1) a –31 (A-G) deletion mutation (also referred to as a 31M mutation), (2) a 14-15M insertion mutation, (3) a CD 43 (G-T) (also referred to as a 43M/N or a 43M mutation), (4) a 27/28M insertion mutation, (5) an IVS-I-1M mutation, (6) an IVS-1-5 (G-C) (also referred to as an IVS-1-5M) mutation, (7) a CAPM deletion mutation, (8) an IntM mutation, (9) a –30M mutation, (10) a –29M/N (also referred to as a –29M mutation), (11) a –32M/N (also referred to as a –32M mutation), (12) a CD37M point mutation, (13) a 90M point mutation, and (14) an IVS-II-5M point mutation. See Luo, Hong-Cheng, et al. "Impact of genotype on endocrinal complications of Children with Alpha-thalassemia in China." Scientific Reports 7 (2017).

Since α-thalassemia is often caused by large genomic fragment deletions while β-thalassemia is often caused by point mutations, different diagnostic methods have been developed for each type of disorder. For example, most laboratories and hospitals currently use breakpoint polymerase chain reaction (PCR) or Gap-PCR followed by agarose gel electrophoresis to diagnose α-thalassemia and use reverse dot-blot hybridization to diagnose β-thalassemia. However, both methods are labor intensive, involve more than ten operational steps between the two methods, and require almost two to three days to complete. In addition, the risks of contamination are high as amplified PCR tubes must be opened as part of both methods.

Other common diagnostic methods for diagnosing α-thalassemia and β-thalassemia include high resolution melting (HRM) analysis, multiplex PCR, and multiplex ligation-dependent probe amplification (MLPA). However, all such methods are also inefficient or time-consuming and lack specificity and accuracy. In addition, current methods also often require that DNA be extracted from the patient's blood rather than other bodily fluids or samples.

Therefore, a solution is needed which reduces the number of operational steps needed to complete a diagnosis for α-thalassemia and β-thalassemia yet maintains or improves the level of accuracy of such multi-step procedures. Moreover, such a solution should also reduce the amount of time needed to make an accurate diagnosis from between two to three days to less than two hours. In addition, such a solution should also lessen the risk of contamination by not necessitating that amplified PCR tubes be opened as part of the diagnostic procedure. Furthermore, such a solution should work equally well with DNA extracted from a patient's blood as DNA extracted from other bodily fluids or samples including amniotic fluid, samples derived from chorionic villus sampling (CVS), and samples derived from swabs.

SUMMARY

Disclosed herein are methods, compositions, and diagnostic kits for the rapid detection of certain types of α-thalassemia and β-thalassemia. In some embodiments, a diagnostic kit, reagents, and methods are disclosed for the rapid detection of various α-thalassemia and β-thalassemia genotypes in multiple patient samples using real-time PCR. More specifically, in certain embodiments, diagnostic kits, reagents, and methods are disclosed for the rapid detection of seven different types of α-thalassemia (i.e., seven different α-thalassemia genotypes) and twenty different types of β-thalassemia (i.e., twenty different β-thalassemia genotypes) in one single multiplex real-time PCR reaction.

In one embodiment, a diagnostic kit for detecting multiple forms of thalassemia using real-time PCR can comprise a reagent mixture for detecting an α-thalassemia −α3.7 deletion genotype or an α-thalassemia −α4.2 deletion genotype. The reagent mixture can comprise a first forward oligonucleotide primer consisting of SEQ ID NO. 1; a second forward oligonucleotide primer consisting of SEQ ID NO. 3; a first reverse oligonucleotide primer consisting of SEQ ID NO. 2; a second reverse oligonucleotide primer consisting of SEQ ID NO. 4; a first fluorescent probe comprising oligonucleotides consisting of SEQ ID NO. 5; a second fluorescent probe comprising oligonucleotides consisting of SEQ ID NO. 6; a forward reference oligonucleotide primer for an internal reference gene consisting of SEQ ID NO. 7; a reverse reference oligonucleotide primer for the internal reference gene consisting of SEQ ID NO. 8; and a reference fluorescent probe for the internal reference gene comprising oligonucleotides consisting of SEQ ID NO. 9.

The first fluorescent probe can comprise a 6-carboxyfluorescein (FAM) fluorophore and a Black Hole Quencher®-1 (BHQ-1) dye having an absorption spectra between about 480 nm and 580 nm. The second fluorescent probe can comprise a hexachloro-6-carboxy-fluorescein (HEX) fluorophore and a Black Hole Quencher®-2 (BHQ-2) dye having an absorption spectra between about 560 nm and about 670 nm. The reference fluorescent probe can comprise a 6-carboxy-X-rhodamine (ROX) fluorophore. In one embodiment, the internal reference gene can be the human lissencephaly type 1 (LIS1) gene.

In some embodiments, the reagent mixture can be an aqueous mixture contained in a single reaction vessel of a multi-vessel container. In other embodiments, the reagent mixture can be pre-spotted in lyophilized form in a single well of a multi-well PCR plate.

In these and other embodiments, the reagent mixture can further comprise a PCR master mix comprising tris(hydroxymethyl)aminomethane (Tris) buffer, deoxynucleotide triphosphates (dNTPs), magnesium chloride (MgCl$_2$), and *Thermus aquaticus* (Taq) polymerase.

The diagnostic kit or the multi-well plate can comprise another reagent mixture for detecting an α-thalassemia −−SEA deletion genotype. The reagent mixture can comprise a SEA forward oligonucleotide primer consisting of SEQ ID NO. 10; a SEA reverse oligonucleotide primer consisting of SEQ ID NO. 11; and a SEA fluorescent probe comprising oligonucleotides consisting of SEQ ID NO. 12.

The diagnostic kit or the multi-well plate can comprise another reagent mixture for detecting an α-thalassemia −−THAI deletion genotype. The reagent mixture can comprise a THAI forward oligonucleotide primer consisting of SEQ ID NO. 100; a THAI reverse oligonucleotide primer consisting of SEQ ID NO. 101; and a THAI fluorescent probe comprising oligonucleotides consisting of SEQ ID NO. 108.

The diagnostic kit or the multi-well plate can comprise another reagent mixture for detecting an α-thalassemia αCSα mutation genotype. The reagent mixture can comprise an αCSα forward oligonucleotide primer consisting of SEQ ID NO. 13; an αCSα reverse oligonucleotide primer consisting of SEQ ID NO. 14; an αCSα fluorescent normal probe comprising oligonucleotides consisting of SEQ ID NO. 19; and an αCSα fluorescent mutant probe comprising oligonucleotides consisting of SEQ ID NO. 20.

The diagnostic kit or the multi-well plate can comprise another reagent mixture for detecting an α-thalassemia αQSα mutation genotype. The reagent mixture can comprise an αQSα forward oligonucleotide primer consisting of SEQ ID NO. 15; an αQSα reverse oligonucleotide primer consisting of SEQ ID NO. 16; an αQSα fluorescent normal probe comprising oligonucleotides consisting of SEQ ID NO. 21; and an αQSα fluorescent mutant probe comprising oligonucleotides consisting of SEQ ID NO. 22.

The diagnostic kit or the multi-well plate can comprise another reagent mixture for detecting α-thalassemia αWSα mutation genotype. The reagent mixture can comprise an αWSα forward oligonucleotide primer consisting of SEQ ID NO. 17; an αWSα reverse oligonucleotide primer consisting of SEQ ID NO. 18; an αWSα fluorescent normal probe comprising oligonucleotides consisting of SEQ ID NO. 23; and an αWSα fluorescent mutant probe comprising oligonucleotides consisting of SEQ ID NO. 24.

The diagnostic kit or the multi-well plate can comprise another reagent mixture for detecting a β-thalassemia 41-42M deletion mutation genotype. The reagent mixture can comprise a 41-42M forward oligonucleotide primer consisting of SEQ ID NO. 25; a 41-42M reverse oligonucleotide primer consisting of SEQ ID NO. 26; a 41-42M fluorescent normal probe comprising oligonucleotides consisting of SEQ ID NO. 59; and a 41-42M fluorescent mutant probe comprising oligonucleotides consisting of SEQ ID NO. 60.

The diagnostic kit or the multi-well plate can comprise another reagent mixture for detecting a β-thalassemia −28M mutation genotype. The reagent mixture can comprise a −28M forward oligonucleotide primer consisting of SEQ ID NO. 27; a −28M reverse oligonucleotide primer consisting of SEQ ID NO. 28; a −28M fluorescent normal probe comprising oligonucleotides consisting of SEQ ID NO. 61; and a −28M fluorescent mutant probe comprising oligonucleotides consisting of SEQ ID NO. 62.

The diagnostic kit or the multi-well plate can comprise another reagent mixture for detecting a β-thalassemia −29M mutation genotype. The reagent mixture comprising a −29M forward oligonucleotide primer consisting of SEQ ID NO. 55; a −29M reverse oligonucleotide primer consisting of SEQ ID NO. 56; a −29M fluorescent normal probe comprising oligonucleotides consisting of SEQ ID NO. 90; and a −29M fluorescent mutant probe comprising oligonucleotides consisting of SEQ ID NO. 91.

The diagnostic kit or the multi-well plate can comprise another reagent mixture for detecting a β-thalassemia 17M mutation genotype. The reagent mixture can comprise a 17M forward oligonucleotide primer consisting of SEQ ID NO. 31; a 17M reverse oligonucleotide primer consisting of SEQ ID NO. 32; a 17M fluorescent normal probe comprising oligonucleotides consisting of SEQ ID NO. 65; and a 17M fluorescent mutant probe comprising oligonucleotides consisting of SEQ ID NO. 66.

The diagnostic kit or the multi-well plate can comprise another reagent mixture for detecting other reagent mixture for detecting a β-thalassemia 71-72M insertion mutation genotype. The reagent mixture can comprise a 71-72M forward oligonucleotide primer consisting of SEQ ID NO. 29; a 71-72M reverse oligonucleotide primer consisting of SEQ ID NO. 30; a 71-72M fluorescent normal probe comprising oligonucleotides consisting of SEQ ID NO. 63; and a 71-72M fluorescent mutant probe comprising oligonucleotides consisting of SEQ ID NO. 64.

DETAILED DESCRIPTION

Figure 1:
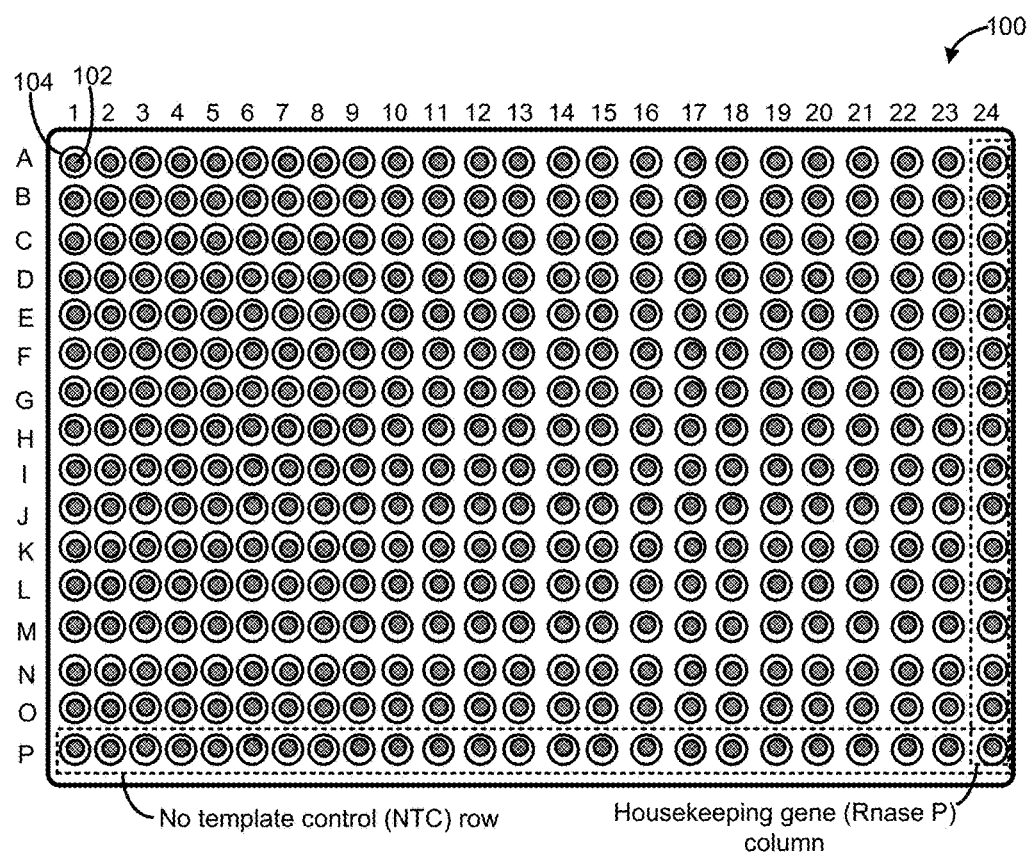
FIG. 1 illustrates a top plan view of a multi-well plate having reagent mixtures pre-spotted in lyophilized form within wells of the multi-well plate.

Disclosed herein are methods, compositions, and diagnostic kits for the rapid detection of certain types of α-thalassemia and β-thalassemia. In some embodiments, a diagnostic kit, certain reagents, and methods are disclosed for the rapid detection of various α-thalassemia and β-thalassemia genotypes in multiple patient samples using real-time PCR. More specifically, in certain embodiments, diagnostic kits, reagents, and methods are disclosed for the rapid detection of seven (7) different α-thalassemia genotypes and twenty (20) different β-thalassemia genotypes in one single multiplex real-time PCR reaction. Table 1 identifies the seven different types of α-thalassemia and the twenty different types of β-thalassemia that can be diagnosed using the kits, reagents, and methods disclosed herein. Table 1 also classifies the disorders by their respective genetic mutations.

TABLE 1

Types of Thalassemia Capable of Being Detected and Classification of Disorders

| Classification | α-thalassemia | β-thalassemia |
| --- | --- | --- |
| Large Fragment Deletion | $-\alpha^{3.7}$ <br> $-\alpha^{4.2}$ <br> __SEA <br> __THAI | |

TABLE 1-continued

Types of Thalassemia Capable of Being Detected and Classification of Disorders

| Classification | α-thalassemia | β-thalassemia |
|---|---|---|
| Short Fragment Deletion | | 31M |
| | | 41-42M |
| | | CAPM |
| Point Mutation | $\alpha^{CS}\alpha$ | -28M |
| | $\alpha^{QS}\alpha$ | -29M |
| | $\alpha^{WS}\alpha$ | -30M |
| | | -32M |
| | | 17M |
| | | 43M |
| | | 90M |
| | | 654M |
| | | IntM |
| | | IVS-I-1M |
| | | IVS-I-5M |
| | | IVS-II-5M |
| | | βEM |
| | | CD37M |
| Insertion Mutation | | 14-15M |
| | | 27/28M |
| | | 71-72M |

One advantage of these kits, reagents, and methods is the ability to make an accurate diagnosis of multiple thalassemia disease profiles in about 120 minutes (2 hours) or between 60 minutes (1 hr) and 120 minutes (2 hours). Such a diagnostic time frame is presently much shorter than the two- to three-days currently required to diagnose such thalassemia profiles using traditional methods. Another advantage of these kits, reagents, and methods is the ability to perform high-throughput analysis of multiple patient biological samples in one single multiplex real-time PCR reaction.

PCR Reagent Mixture

Disclosed herein are various ready-to-use PCR reagent mixtures for use in the diagnosis of various α-thalassemia and β-thalassemia genotypes with real-time PCR detection instruments. In some embodiments, each of the PCR reagent mixtures can comprise the components and concentrations shown in Table 2.

TABLE 2

Real-Time PCR Reagent Mixture

| PCR Reagent Mixture Component | Concentration |
|---|---|
| Tris buffer | 50 mM |
| MgCl$_2$ | 5 mM |
| dNTPs | Each 0.2 mM |
| Taq DNA Polymerase | 0.05 units (U)/μL |
| Forward Primer(s) | 0.9 μM |
| Reverse Primer(s) | 0.9 μM |
| Mutant Probe(s) | 0.25 μM |
| Normal Probe(s), if any | 0.25 μM |
| Total Volume (per reaction well or tube): | ~18 μL |

The forward primers and reverse primers indicated in Table 2 can be any of the forward and reverse primers included in Table 3. Moreover, the allelic specific probes indicated in Table 2 can be any of the fluorescent probes included in Table 3. As will be discussed the following sections, a reaction container or vessel, such as a well of a multi-well plate or a PCR reaction tube, can be pre-spotted, pre-filled, or pre-aliquoted with the PCR reagent mixture indicated in Table 2. For example, each of the wells of a multi-well plate or a PCR reaction tube can be pre-spotted, pre-filled, or pre-aliquoted with about 18 μL of the PCR reagent mixture.

Primers and Probes

Table 3 below includes sequences for certain forward primers, reverse primers, normal or wildtype probes, and mutant probes designed for detecting the types of α-thalassemia and β-thalassemia genotypes indicated in Table 1. Such primers and probes can be included as part of various ready-to-use PCR reagent mixtures, such as mixtures indicated in Table 2.

TABLE 3

Primer and probe sequences for detecting α-thalassemia and β-thalassemia genotypes

| SEQ ID NO. | Primer Direction/ Probe Type | Primer or Probe Name | Length | Sequence (5'-3') | Deletion or Mutation Targeted |
|---|---|---|---|---|---|
| 1 | Forward | α1-F | 25 | TGTGTGTACTTGTGTGATGGTTAGA | $-\alpha^{3.7}$, $-\alpha^{4.2}$ |
| 2 | Reverse | α1-R | 28 | CTGGTTAAACAGGTAAACAAAGCAATAG | $-\alpha^{3.7}$, $-\alpha^{4.2}$ |
| 3 | Forward | α2-F | 18 | TCCTTGCACCGGCCCTTC | $-\alpha^{3.7}$, $-\alpha^{4.2}$ |
| 4 | Reverse | α2-R | 22 | GTCCTTGGTCTGAGACAGGTAA | $-\alpha^{3.7}$, $-\alpha^{4.2}$ |
| 5 | Probe | Probe-α1 | 28 | TGCCTACCTCCCAGAGGAGGTTGAATGC | $-\alpha^{3.7}$, $-\alpha^{4.2}$ |
| 6 | Probe | Probe-α2 | 31 | TGAATAAAGTCTGAGTGGGCAGCAGCCTGTG | $-\alpha^{3.7}$, $-\alpha^{4.2}$ |
| 7 | Forward | LIS1-F | 20 | GATTGCCACAGCCTGCTGCT | N/A |
| 8 | Reverse | LIS1-R | 21 | AGGGCTCATTACATGTGGACC | N/A |
| 9 | Probe | Probe-LIS1 | 29 | CCAGACATCCTCCATGTGAGAAGCAGCGA | N/A |
| 10 | Forward | SEA-F | 23 | CTCTGTGTTCTCAGTATTGGAGG | $--^{SEA}$ |
| 11 | Reverse | SEA-R | 22 | GAGTGCAGTGTTGTAGTCATGG | $--^{SEA}$ |

TABLE 3-continued

Primer and probe sequences for detecting α-thalassemia and β-thalassemia genotypes

| SEQ ID NO. | Primer Direction/ Probe Type | Primer or Probe Name | Length | Sequence (5'-3') | Deletion or Mutation Targeted |
|---|---|---|---|---|---|
| 12 | Probe | Probe-SEA | 26 | AGGGGAGAAGCTGAGTGATGGGTCCG | --$^{SEA}$ |
| 13 | Forward | CS-F | 21 | CTGGACAAGTTCCTGGCTTCT | α$^{CS}$α |
| 14 | Reverse | CS-R | 18 | GTGCAAGGAGGGGAGGAG | α$^{CS}$α |
| 15 | Forward | QS-F | 18 | ACCTCCCCGCCGAGTTCA | α$^{QS}$α |
| 16 | Reverse | QS-R | 21 | GAGGCTCCAGCTTAACGGTAT | α$^{QS}$α |
| 17 | Forward | WS-F | 18 | ACCTCCCCGCCGAGTTCA | α$^{WS}$α |
| 18 | Reverse | WS-R | 21 | GAGGCTCCAGCTTAACGGTAT | α$^{CS}$α |
| 19 | Normal Probe | Probe-CSN | 30 | CACCGTGCTGACCTCCAAATACCGTTAAGC | α$^{CS}$α |
| 20 | Mutant Probe | Probe-CSM | 30 | CACCGTGCTGACCTCCAAATACCGTCAAGC | α$^{CS}$α |
| 21 | Normal Probe | Probe-QSN | 22 | CTGCGGTGCACGCCTCCCTGGA | α$^{QS}$α |
| 22 | Mutant Probe | Probe-QSM | 22 | CTGCGGTGCACGCCTCCCCGGA | α$^{QS}$α |
| 23 | Normal Probe | Probe-WSN | 22 | CTGCGGTGCACGCCTCCCTGGA | α$^{WS}$α |
| 24 | Mutant Probe | Probe-WSM | 22 | CTGCGGTGCAGGCCTCCCTGGA | α$^{WS}$α |
| 25 | Forward | 41-42M-F | 21 | CTTAGGCTGCTGGTGGTCTAC | 41-42M |
| 26 | Reverse | 41-42M-R | 22 | CAGCATCAGGAGTGGACAGATC | 41-42M |
| 27 | Forward | -28M-F | 16 | GCAGGGAGGGCAGGAG | -28M |
| 28 | Reverse | -28M-R | 25 | GTTGTGTCAGAAGCAAATGTAAGCA | -28M |
| 29 | Forward | 71-72M-F | 21 | AAGGCTCATGGCAAGAAAGTG | 71-72M |
| 30 | Reverse | 71-72M-R | 21 | AAAGGTGCCCTTGAGGTTGTC | 71-72M |
| 31 | Forward | 17M-F | 22 | GAGGAGAAGTCTGCCGTTACTG | 17M |
| 32 | Reverse | 17M-R | 20 | GGCCTCACCACCAACTTCAT | 17M |
| 33 | Forward | βEM-F | 21 | GCAAGGTGAACGTGGATGAAG | βEM |
| 34 | Reverse | βEM-R | 26 | GTCTCCTTAAACCTGTCTTGTAACCT | βEM |
| 35 | Forward | 654M-F | 25 | TGCCTCTTTGCACCATTCTAAAGAA | 654M |
| 36 | Reverse | 654M-R | 34 | AACCTCTTACATCAGTTACAATTTATATGCAGAA | 654M |
| 37 | Forward | 31M-F | 23 | ACTGACTCTCTCTGCCTATTGGT | 31M |
| 38 | Reverse | 31M-R | 20 | CCTCTGGGTCCAAGGGTAGA | 31M |
| 39 | Forward | 14-15M-F | 24 | CTAGCAACCTCAAACAGACACCAT | 14-15M |
| 40 | Reverse | 14-15M-R | 21 | CACCAACTTCATCCACGTTCA | 14-15M |
| 41 | Forward | 43M-F | 21 | CTTAGGCTGCTGGTGGTCTAC | 43M |
| 42 | Reverse | 43M-R | 22 | CAGCATCAGGAGTGGACAGATC | 43M |
| 43 | Forward | 27/28M-F | 22 | GGTGAACGTGGATGAAGTTGGT | 27/28M |
| 44 | Reverse | 27/28M-R | 26 | GTCTCCTTAAACCTGTCTTGTAACCT | 27/28M |

TABLE 3-continued

Primer and probe sequences for detecting α-thalassemia and β-thalassemia genotypes

| SEQ ID NO. | Primer Direction/ Probe Type | Primer or Probe Name | Length | Sequence (5'-3') | Deletion or Mutation Targeted |
|---|---|---|---|---|---|
| 45 | Forward | IVS-I-1M-F | 22 | GGTGAACGTGGATGAAGTTGGT | IVS-I-1M |
| 46 | Reverse | IVS-I-1M-R | 25 | GCCCAGTTTCTATTGGTCTCCTTAA | IVS-I-1M |
| 47 | Forward | IVS-I-5M-F | 22 | GGTGAACGTGGATGAAGTTGGT | IVS-I-5M |
| 48 | Reverse | IVS-I-5M-R | 25 | GCCCAGTTTCTATTGGTCTCCTTAA | IVS-I-5M |
| 49 | Forward | CAPM-F | 25 | GCTTACATTTGCTTCTGACACAACT | CAPM |
| 50 | Reverse | CAPM-R | 21 | CTCAGGAGTCAGATGCACCAT | CAPM |
| 51 | Forward | IntM-F | 24 | CTGTGTTCACTAGCAACCTCAAAC | IntM |
| 52 | Reverse | IntM-R | 21 | GGCAGTAACGGCAGACTTCTC | IntM |
| 53 | Forward | -30M-F | 16 | GCAGGGAGGGCAGGAG | -30M |
| 54 | Reverse | -30M-R | 25 | GTTGTGTCAGAAGCAAATGTAAGCA | -30M |
| 55 | Forward | -29M-F | 16 | GCAGGGAGGGCAGGAG | -29M |
| 56 | Reverse | -29M-R | 25 | GTTGTGTCAGAAGCAAATGTAAGCA | -29M |
| 57 | Forward | -32M-F | 16 | GCAGGGAGGGCAGGAG | -32M |
| 58 | Reverse | -32M-R | 25 | GTTGTGTCAGAAGCAAATGTAAGCA | -32M |
| 59 | Normal Probe | Probe-41-42N | 18 | AGGACTCAAAGAACCTCT | 41-42M |
| 60 | Mutant Probe | Probe-41-42M | 17 | CAAAGGACTCAACCTCT | 41-42M |
| 61 | Normal Probe | Probe-28N | 17 | CCCTGACTTTTATGCCC | -28M |
| 62 | Mutant Probe | Probe-28M | 16 | CCTGACTTCTATGCCC | -28M |
| 63 | Normal Probe | Probe-71-72N | 15 | TCGGTGCCTTTAGTG | 71-72M |
| 64 | Mutant Probe | Probe-71-72M | 15 | CGGTGCCTTTAAGTG | 71-72M |
| 65 | Normal Probe | Probe-17N | 18 | CACGTTCACCTTGCCCCA | 17M |
| 66 | Mutant Probe | Probe-17M | 17 | ACGTTCACCTAGCCCCA | 17M |
| 67 | Normal Probe | Probe-βEN | 15 | TGGTGGTGAGGCCCT | βEM |
| 68 | Mutant Probe | Probe-βEM | 16 | TTGGTGGTAAGGCCCT | βEM |
| 69 | Normal Probe | Probe-654N | 21 | AGATATTGCTATTGCCTTAAC | 654M |
| 70 | Mutant Probe | Probe-654M | 21 | AGATATTGCTATTACCTTAAC | 654M |
| 71 | Normal Probe | Probe-31N | 15 | CACCAGCAGCCTAAG | 31M |
| 72 | Mutant Probe | Probe-31M | 15 | CCACCAGCACCTAAG | 31M |
| 73 | Normal Probe | Probe-14-15N | 16 | CGTTACTGCCCTGTGG | 14-15M |

TABLE 3-continued

Primer and probe sequences for detecting α-thalassemia and β-thalassemia genotypes

| SEQ ID NO. | Primer Direction/ Probe Type | Primer or Probe Name | Length | Sequence (5'-3') | Deletion or Mutation Targeted |
|---|---|---|---|---|---|
| 74 | Mutant Probe | Probe-14-15M | 16 | CGTTACTGCCCTGGTG | 14-15M |
| 75 | Normal Probe | Probe-43N | 19 | AGAGGTTCTTTGAGTCCTT | 43M |
| 76 | Mutant Probe | Probe-43M | 20 | CAGAGGTTCTTTTAGTCCTT | 43M |
| 77 | Normal Probe | Probe-27/28N | 16 | TGAGGCCCCTGGGCAG | 27/28M |
| 78 | Mutant Probe | Probe-27/28M | 15 | TGAGGCCCTGGGCAG | 27/28M |
| 79 | Normal Probe | Probe-IVS-I-1N | 16 | CTGGGCAGGTTGGTAT | IVS-I-1M |
| 80 | Mutant Probe | Probe-IVS-I-1M-A | 16 | CTGGGCAGATTGGTAT | IVS-I-1M |
| 81 | Mutant Probe | Probe-IVS-I-1M-T | 16 | CTGGGCAGTTTGGTAT | IVS-I-1M |
| 82 | Normal Probe | Probe-IVS-I-5N | 16 | CAGGTTGGTATCAAGG | IVS-I-5M |
| 83 | Mutant Probe | Probe-IVS-I-5M | 16 | CAGGTTGCTATCAAGG | IVS-I-5M |
| 84 | Normal Probe | Probe-CAPN | 18 | CAACCTCAAACAGACACC | CAPM |
| 85 | Mutant Probe | Probe-CAPM | 17 | TAGCAACCTCAGACACC | CAPM |
| 86 | Normal Probe | Probe-IntN | 17 | TCAAACAGACACCATGG | IntM |
| 87 | Mutant Probe | Probe-IntM | 17 | TCAAACAGACACCAGGG | IntM |
| 88 | Normal Probe | Probe-30N | 19 | CCCTGACTTTTATGCCCAG | -30M |
| 89 | Mutant Probe | Probe-30M | 18 | CCTGACTTTTGTGCCCAG | -30M |
| 90 | Normal Probe | Probe-29N | 17 | CCCTGACTTTTATGCCC | -29M |
| 91 | Mutant Probe | Probe29M | 16 | CCTGACTTTCATGCCC | -29M |
| 92 | Normal Probe | Probe-32N | 20 | CCTGACTTTTATGCCCAGCC | -32M |
| 93 | Mutant Probe | Probe-32M | 21 | CCCTGACTTTTATTCCCAGCC | -32M |
| 94 | Forward | CD37M-F | 26 | TCTCTCTGCCTATTGGTCTATTTTCC | CD37M |
| 95 | Reverse | CD37M-R | 22 | GATCCCCAAAGGACTCAAAGAA | CD37M |
| 96 | Forward | 90M-F | 24 | CAGGTACGGCTGTCATCACTTAGA | 90M |
| 97 | Reverse | 90M-R | 22 | TAGATGGCTCTGCCCTGACTTT | 90M |
| 98 | Forward | IVS-II-5M-F | 20 | CTGGACAACCTCAAGGGCAC | IVS-II-5M |
| 99 | Reverse | IVS-II-5M-R | 22 | AAAGAAAACATCAAGGGTCCCA | IVS-II-5M |

TABLE 3-continued

Primer and probe sequences for detecting α-thalassemia and β-thalassemia genotypes

| SEQ ID NO. | Primer Direction/ Probe Type | Primer or Probe Name | Length | Sequence (5'-3') | Deletion or Mutation Targeted |
|---|---|---|---|---|---|
| 100 | Forward | THAI-F | 23 | TGACTGCATCATAATTCCAGCAG | --$^{THAI}$ |
| 101 | Reverse | THAI-R | 21 | CAAGTGGGCTGAGCCCTTGAG | --$^{THAI}$ |
| 102 | Mutant Probe | Probe-CD37M | 16 | TGGTCTACCCTTAGAC | CD37M |
| 103 | Normal Probe | Probe-CD37N | 16 | TGGTCTACCCTTGGAC | CD37M |
| 104 | Mutant Probe | Probe-90M | 14 | TGGAGCCATACCCT | 90M |
| 105 | Normal Probe | Probe-90N | 14 | TGGAGCCACACCCT | 90M |
| 106 | Mutant Probe | Probe-IVS-II-5M | 16 | ACTTCAGGGTGACTCT | IVS-II-5M |
| 107 | Normal Probe | Probe-IVS-II-5N | 17 | AACTTCAGGGTGAGTCT | IVS-II-5M |
| 108 | Probe | Probe-THAI | 34 | AGGAAGAATAAAGCGAGAGGAATCACATTCCTCA | --$^{THAI}$ |

Table 4 below discloses certain fluorescent probes designed for detecting the types of α-thalassemia and β-thalassemia genotypes indicated in Table 1. As shown in Table 4, certain reporter fluorophore and quencher pairs were selected based on their absorption spectra and detection specificity. For example, the inventors discovered that fluorescent probes designed with a 6-carboxy-fluorescine (FAM) fluorophore (or fluorescent dye molecule) and a Black Hole Quencher®-1 (BHQ-1) dye having an absorption spectra between about 480 nm and 580 nm could be used to selectively generate certain fluorescent signals indicating the presence of mutant alleles. Also, for example, the inventors discovered that fluorescent probes designed with a hexachloro-6-carboxy-fluorescine (HEX) fluorophore and a BHQ-1 dye could be used to selectively generate certain fluorescent signals indicating the presence of certain normal or wild-type alleles or certain mutant alleles. Although HEX fluorophores are indicated in Table 4, it is contemplated by this disclosure that other fluorophores such as VIC™ fluorescent dyes or fluorophores can also be used in lieu or HEX. Moreover, the inventors discovered that fluorescent probes designed with a 6-carboxy-X-rhodamine (ROX) fluorophore and a Black Hole Quencher®-2 (BHQ-2) dye having an absorption spectra between about 560 nm and about 670 nm could be used to selectively generate certain fluorescent signals indicating the level of certain internal reference genes.

TABLE 4

Fluorescent probes for detecting α-thalassemia and β-thalassemia deletion and mutant genotypes.

| Probe Name | Probe Type | Probe with Fluorescent Reporter and Quencher (5''-3') | SEQ ID NO. of sequence included as part of probe | Reporter/ Quencher |
|---|---|---|---|---|
| Probe-α1 | Probe | FAM-TGCCTACCTCCCAGAGGAGGTTGAATGC-BHQ1 | 5 | FAM/BHQ1 |
| Probe-α2 | Probe | HEX-TGAATAAAGTCTGAGTGGGCAGCAGCCTGTG-BHQ1 | 6 | HEX/BHQ1 |
| Probe-U1 | Probe | ROX-CCAGACATCCTCCATGTGAGAAGCAGCGA-BHQ2 | 9 | ROX/BHQ2 |
| Probe-SEA | Probe | FAM-AGGGGAGAAGCTGAGTGATGGGTCCG-BHQ1 | 12 | FAM/BHQ1 |
| Probe-CSN | Normal | HEX-CACCGTGCTGACCTCCAAATACCGTTAAGC-BHQ1 | 19 | HEX/BHQ1 |
| Probe-CSM | Mutant | FAM-CACCGTGCTGACCTCCAAATACCGTCAAGC-BHQ1 | 20 | FAM/BHQ1 |

TABLE 4-continued

Fluorescent probes for detecting α-thalassemia and β-thalassemia deletion and mutant genotypes.

| Probe Name | Probe Type | Probe with Fluorescent Reporter and Quencher (5''-3') | SEQ ID NO. of sequence included as part of probe | Reporter/ Quencher |
| --- | --- | --- | --- | --- |
| Probe-QSN | Normal | HEX-CTGCGGTGCACGCCTCCCTGGA | 21 | HEX/BHQ1 |
| Probe-QSM | Mutant | FAM-CTGCGGTGCACGCCTCCCCGGA-BHQ1 | 22 | FAM/BHQ1 |
| Probe-WSN | Normal | HEX-CTGCGGTGCACGCCTCCCTGGA-BHQ1 | 23 | HEX/BHQ1 |
| Probe-WSM | Mutant | FAM-CTGCGGTGCAGGCCTCCCTGGA-BHQ1 | 24 | FAM/BHQ1 |
| Probe-41-42N | Normal | HEX-AGGACTCAAAGAACCTCT-BHQ1 | 59 | HEX/BHQ1 |
| Probe-41-42M | Mutant | FAM-CAAAGGACTCAACCTCT-BHQ1 | 60 | FAM/BHQ1 |
| Probe-28N | Normal | HEX-CCCTGACTTTTATGCCC-BHQ1 | 61 | HEX/BHQ1 |
| Probe-28M | Mutant | FAM-CCTGACTTCTATGCCC-BHQ1 | 62 | FAM/BHQ1 |
| Probe-71-72N | Normal | HEX-TCGGTGCCTTTAGTG-BHQ1 | 63 | HEX/BHQ1 |
| Probe-71-72M | Mutant | FAM-CGGTGCCTTTAAGTG-BHQ1 | 64 | FAM/BHQ1 |
| Probe-17N | Normal | HEX-CACGTTCACCTTGCCCCA-BHQ1 | 65 | HEX/BHQ1 |
| Probe-17M | Mutant | FAM-ACGTTCACCTAGCCCCA-BHQ1 | 66 | FAM/BHQ1 |
| Probe-βEN | Normal | HEX-TGGTGGTGAGGCCCT-BHQ1 | 67 | HEX/BHQ1 |
| Probe-βEM | Mutant | FAM-TTGGTGGTAAGGCCCT-BHQ1 | 68 | FAM/BHQ1 |
| Probe-654N | Normal | HEX-AGATATTGCTATTGCCTTAAC-BHQ1 | 69 | HEX/BHQ1 |
| Probe-654M | Mutant | FAM-AGATATTGCTATTACCTTAAC-BHQ1 | 70 | FAM/BHQ1 |
| Probe-31N | Normal | HEX-CACCAGCAGCCTAAG-BHQ1 | 71 | HEX/BHQ1 |
| Probe-31M | Mutant | FAM-CCACCAGCACCTAAG-BHQ1 | 72 | FAM/BHQ1 |
| Probe-14-15N | Normal | HEX-CGTTACTGCCCTGTGG-BHQ1 | 73 | HEX/BHQ1 |
| Probe-14-15M | Mutant | FAM-CGTTACTGCCCTGGTG-BHQ1 | 74 | FAM/BHQ1 |
| Probe-43N | Normal | HEX-AGAGGTTCTTTGAGTCCTT-BHQ1 | 75 | HEX/BHQ1 |
| Probe-43M | Mutant | FAM-CAGAGGTTCTTTTAGTCCTT-BHQ1 | 76 | FAM/BHQ1 |
| Probe-27/28N | Normal | HEX-TGAGGCCCCTGGGCAG-BHQ1 | 77 | HEX/BHQ1 |
| Probe-27/28M | Mutant | FAM-TGAGGCCCTGGGCAG-BHQ1 | 78 | FAM/BHQ1 |

TABLE 4-continued

Fluorescent probes for detecting α-thalassemia and β-thalassemia deletion and mutant genotypes.

| Probe Name | Probe Type | Probe with Fluorescent Reporter and Quencher (5''-3') | SEQ ID NO. of sequence included as part of probe | Reporter/ Quencher |
|---|---|---|---|---|
| Probe-IVS-I-1N | Normal | HEX-CTGGGCAGGTTGGTAT-BHQ1 | 79 | HEX/BHQ1 |
| Probe-IVS-I-1M-A | Mutant | FAM-CTGGGCAGATTGGTAT-BHQ1 | 80 | FAM/BHQ1 |
| Probe-IVS-I-1M-T | Mutant | FAM-CTGGGCAGTTTGGTAT-BHQ1 | 81 | FAM/BHQ1 |
| Probe-IVS-I-5N | Normal | HEX-CAGGTTGGTATCAAGG-BHQ1 | 82 | HEX/BHQ1 |
| Probe-IVS-I-5M | Mutant | FAM-CAGGTTGCTATCAAGG-BHQ1 | 83 | FAM/BHQ1 |
| Probe-CAPN | Normal | HEX-CAACCTCAAACAGACACC-BHQ1 | 84 | HEX/BHQ1 |
| Probe-CAPM | Mutant | FAM-TAGCAACCTCAGACACC-BHQ1 | 85 | FAM/BHQ1 |
| Probe-IntN | Normal | HEX-TCAAACAGACACCATGG-BHQ1 | 86 | HEX/BHQ1 |
| Probe-IntM | Mutant | FAM-TCAAACAGACACCAGGG-BHQ1 | 87 | FAM/BHQ1 |
| Probe-30N | Normal | HEX-CCCTGACTTTTATGCCCAG-BHQ1 | 88 | HEX/BHQ1 |
| Probe-30M | Mutant | FAM-CCTGACTTTTGTGCCCAG-BHQ1 | 89 | FAM/BHQ1 |
| Probe-29N | Normal | HEX-CCCTGACTTTTATGCCC-BHQ1 | 90 | HEX/BHQ1 |
| Probe29M | Mutant | FAM-CCTGACTTTCATGCCC-BHQ1 | 91 | FAM/BHQ1 |
| Probe-32N | Normal | HEX-CCTGACTTTTATGCCCAGCC-BHQ1 | 92 | HEX/BHQ1 |
| Probe-32M | Mutant | FAM-CCCTGACTTTTATTCCCAGCC-BHQ1 | 93 | FAM/BHQ1 |
| Probe-CD37M | Mutant | FAM-TGGTCTACCCTTAGAC-BHQ1 | 102 | FAM/BHQ1 |
| Probe-CD37N | Normal | HEX-TGGTCTACCCTTGGAC-BHQ1 | 103 | HEX/BHQ1 |
| Probe-90M | Mutant | FAM-TGGAGCCATACCCT-BHQ1 | 104 | FAM/BHQ1 |
| Probe-90N | Normal | HEX-TGGAGCCACACCCT-BHQ1 | 105 | HEX/BHQ1 |
| Probe-IVS-II-5M | Mutant | FAM-ACTTCAGGGTGACTCT-BHQ1 | 106 | FAM/BHQ1 |
| Probe-IVS-II-5N | Normal | HEX-AACTTCAGGGTGAGTCT-BHQ1 | 107 | HEX/BHQ1 |
| Probe-THAI | Probe | FAM-AGGAAGAATAAAGCGAGAGGAATCACATTCCTCA-BHQ1 | 108 | FAM/BHQ1 |

In one embodiment, a diagnostic kit for detecting multiple forms of thalassemia using real-time PCR can comprise a first α-thalassemia reagent mixture for detecting an α-thalassemia −α3.7 deletion genotype or an α-thalassemia −α4.2 deletion genotype. The first α-thalassemia reagent mixture can comprise a PCR master mix or PCR reaction mix comprising Tris buffer, magnesium chloride ($MgCl_2$), deoxynucleotide triphosphates (dNTPs), and *Thermus aquaticus* (Taq) DNA polymerase in the concentrations indicated in Table 2.

The primers and probes of the first α-thalassemia reagent mixture can comprise a first forward oligonucleotide primer consisting of SEQ ID NO. 1, a first reverse oligonucleotide primer consisting of SEQ ID NO. 2, a second forward oligonucleotide primer consisting of SEQ ID NO. 3, a second reverse oligonucleotide primer consisting of SEQ ID NO. 4, a first fluorescent probe comprising oligonucleotides consisting of SEQ ID NO. 5, a second fluorescent probe comprising oligonucleotides consisting of SEQ ID NO. 6, a forward reference oligonucleotide primer for an internal reference gene consisting of SEQ ID NO. 7, a reverse reference oligonucleotide primer for the internal reference gene consisting of SEQ ID NO. 8, and a reference fluorescent probe for the internal reference gene comprising oligonucleotides consisting of SEQ ID NO. 9.

In one embodiment, the first forward oligonucleotide primer consisting of SEQ ID NO. 1, the second forward oligonucleotide primer consisting of SEQ ID NO. 3, and the forward reference oligonucleotide primer for an internal reference gene consisting of SEQ ID NO. 7 can be prepared and provided in the total concentration indicated in Table 2 (e.g., 0.9 µM). In this and other embodiments, the first α-thalassemia reagent mixture can comprise the first reverse oligonucleotide primer consisting of SEQ ID NO. 2, the second reverse oligonucleotide primer consisting of SEQ ID NO. 4, and the reverse reference oligonucleotide primer for the internal reference gene consisting of SEQ ID NO. 8 in the total concentration indicated in Table 2 (e.g., 0.9 µM). Also, in these and other embodiments, the first α-thalassemia reagent mixture can comprise the first fluorescent probe comprising oligonucleotides consisting of SEQ ID NO. 5, the second fluorescent probe comprising oligonucleotides consisting of SEQ ID NO. 6, and the reference fluorescent probe for the internal reference gene comprising oligonucleotides consisting of SEQ ID NO. 9 in a total concentration of 0.25 µM or between 0.25 µM and 0.50 µM. One benefit of the first α-thalassemia reagent mixture is the ability to detect one of two α-thalassemia genotypes (the −α3.7 deletion genotype or the −α4.2 deletion genotype) by applying a patient DNA template to the reagent mixture and performing a real-time PCR amplification using one reaction vessel, tube, or well comprising the patient DNA template and the reagent mixture.

In the same or different embodiment, the diagnostic kit can comprise another reagent mixture or a second α-thalassemia reagent mixture for detecting an α-thalassemia −−SEA (or −−$^{SEA}$) deletion genotype. The second α-thalassemia reagent mixture can comprise the pre-formulated PCR master mix or PCR reaction mix previously disclosed in the concentrations indicated in Table 2. The primers and probes of the second α-thalassemia reagent mixture can comprise a SEA forward oligonucleotide primer consisting of SEQ ID NO. 10, a SEA reverse oligonucleotide primer consisting of SEQ ID NO. 11, and a SEA fluorescent probe comprising oligonucleotides consisting of SEQ ID NO. 12.

In this and other embodiments, the second α-thalassemia reagent mixture can comprise the SEA forward oligonucleotide primer consisting of SEQ ID NO. 10 in the concentration indicated in Table 2 (e.g., 0.9 µM). In these and other embodiments, the second α-thalassemia reagent mixture can comprise the SEA reverse oligonucleotide primer consisting of SEQ ID NO. 11 in the concentration indicated in Table 2 (e.g., 0.9 µM). Also, in these and other embodiments, the second α-thalassemia reagent mixture can comprise the SEA fluorescent probe comprising oligonucleotides consisting of SEQ ID NO. 12 in the amount of 0.25 µM or between 0.25 µM and 0.50 µM.

In the same or different embodiment, the diagnostic kit can comprise another reagent mixture or a third α-thalassemia reagent mixture for detecting an α-thalassemia −−THAI (or −−$^{THAI}$) deletion genotype. The third α-thalassemia reagent mixture can comprise the pre-formulated PCR master mix or PCR reaction mix previously disclosed in the concentrations indicated in Table 2. The primers and probes of the third α-thalassemia reagent mixture can comprise a THAI forward oligonucleotide primer consisting of SEQ ID NO. 100, a THAI reverse oligonucleotide primer consisting of SEQ ID NO. 101, and a THAI fluorescent probe comprising oligonucleotides consisting of SEQ ID NO. 108.

In this and other embodiments, the third α-thalassemia reagent mixture can comprise the THAI forward oligonucleotide primer consisting of SEQ ID NO. 100 in the concentration indicated in Table 2 (e.g., 0.9 µM). In these and other embodiments, the third α-thalassemia reagent mixture can comprise the THAI reverse oligonucleotide primer consisting of SEQ ID NO. 101 in the concentration indicated in Table 2 (e.g., 0.9 µM). Also, in these and other embodiments, the third α-thalassemia reagent mixture can comprise the THAI fluorescent probe comprising oligonucleotides consisting of SEQ ID NO. 108 in the amount of 0.25 µM or between 0.25 µM and 0.50 µM.

In the same or different embodiment, the diagnostic kit can comprise another reagent mixture or a fourth α-thalassemia reagent mixture for detecting an α-thalassemia αCSα mutation genotype. The fourth α-thalassemia reagent mixture can comprise the pre-formulated PCR master mix or PCR reaction mix previously disclosed in the concentrations indicated in Table 2. The primers and probes of the fourth α-thalassemia reagent mixture can comprise an αCSα forward oligonucleotide primer consisting of SEQ ID NO. 13, an αCSα reverse oligonucleotide primer consisting of SEQ ID NO. 14, an αCSα fluorescent normal probe comprising oligonucleotides consisting of SEQ ID NO. 19, and an αCSα fluorescent mutant probe comprising oligonucleotides consisting of SEQ ID NO. 20.

In this and other embodiments, the fourth α-thalassemia reagent mixture can comprise the αCSα forward oligonucleotide primer consisting of SEQ ID NO. 13 in the concentration indicated in Table 2 (e.g., 0.9 µM). In these and other embodiments, the fourth α-thalassemia reagent mixture can comprise the αCSα reverse oligonucleotide primer consisting of SEQ ID NO. 14 in the concentration indicated in Table 2 (e.g., 0.9 µM). Also, in these and other embodiments, the fourth α-thalassemia reagent mixture can comprise the αCSα fluorescent normal probe comprising oligonucleotides consisting of SEQ ID NO. 19 in the concentration indicated in Table 2 (e.g., 0.25 µM) and the αCSα fluorescent mutant probe comprising oligonucleotides consisting of SEQ ID NO. 20 in the concentration indicated in Table 2 (e.g., 0.25 µM).

In the same or different embodiment, the diagnostic kit can comprise another reagent mixture or a fifth α-thalassemia reagent mixture for detecting an α-thalassemia αQSα mutation genotype. The fifth α-thalassemia reagent mixture can comprise the pre-formulated PCR master mix or PCR reaction mix previously disclosed in the concentrations indicated in Table 2. The primers and probes of the fifth α-thalassemia reagent mixture can comprise an αQSα forward oligonucleotide primer consisting of SEQ ID NO. 15, an αQSα reverse oligonucleotide primer consisting of SEQ ID NO. 16, an αQSα fluorescent normal probe comprising oligonucleotides consisting of SEQ ID NO. 21, and an αQSα fluorescent mutant probe comprising oligonucleotides consisting of SEQ ID NO. 22.

In this and other embodiments, the fifth α-thalassemia reagent mixture can comprise the αQSα forward oligonucleotide primer consisting of SEQ ID NO. 15 in the concentration indicated in Table 2 (e.g., 0.9 µM). In these and other embodiments, the fifth α-thalassemia reagent mixture can comprise the αQSα reverse oligonucleotide primer consisting of SEQ ID NO. 16 in the concentration indicated in Table 2 (e.g., 0.9 µM). Also, in these and other embodiments, the fifth α-thalassemia reagent mixture can comprise the αQSα fluorescent normal probe comprising oligonucleotides consisting of SEQ ID NO. 21 in the concentration indicated in Table 2 (e.g., 0.25 µM) and the αQSα fluorescent mutant probe comprising oligonucleotides consisting of SEQ ID NO. 22 in the concentration indicated in Table 2 (e.g., 0.25 µM).

In the same or different embodiment, the diagnostic kit can comprise another reagent mixture or a sixth α-thalassemia reagent mixture for detecting an α-thalassemia αWSα mutation genotype. The sixth α-thalassemia reagent mixture can comprise the pre-formulated PCR master mix or PCR reaction mix previously disclosed in the concentrations indicated in Table 2. The primers and probes of the sixth α-thalassemia reagent mixture can comprise an αWSα forward oligonucleotide primer consisting of SEQ ID NO. 17, an αWSα reverse oligonucleotide primer consisting of SEQ ID NO. 18, an αWSα fluorescent normal probe comprising oligonucleotides consisting of SEQ ID NO. 23, and an αWSα fluorescent mutant probe comprising oligonucleotides consisting of SEQ ID NO. 24.

In this and other embodiments, the sixth α-thalassemia reagent mixture can comprise the αWSα forward oligonucleotide primer consisting of SEQ ID NO. 17 in the concentration indicated in Table 2 (e.g., 0.9 µM). In these and other embodiments, the sixth α-thalassemia reagent mixture can comprise the αWSα reverse oligonucleotide primer consisting of SEQ ID NO. 18 in the concentration indicated in Table 2 (e.g., 0.9 µM). Also, in these and other embodiments, the sixth α-thalassemia reagent mixture can comprise the αWSα fluorescent normal probe comprising oligonucleotides consisting of SEQ ID NO. 23 in the concentration indicated in Table 2 (e.g., 0.25 µM) and the αWSα fluorescent mutant probe comprising oligonucleotides consisting of SEQ ID NO. 24 in the concentration indicated in Table 2 (e.g., 0.25 µM).

In the same or different embodiment, the diagnostic kit can comprise another reagent mixture or a first β-thalassemia reagent mixture for detecting a β-thalassemia 41-42M deletion genotype. The first β-thalassemia reagent mixture can comprise the pre-formulated PCR master mix or PCR reaction mix previously disclosed in the concentrations indicated in Table 2. The primers and probes of the first β-thalassemia reagent mixture can comprise a 41-42M forward oligonucleotide primer consisting of SEQ ID NO. 25, a 41-42M reverse oligonucleotide primer consisting of SEQ ID NO. 26, a 41-42M fluorescent normal probe comprising oligonucleotides consisting of SEQ ID NO. 59, and a 41-42M fluorescent mutant probe comprising oligonucleotides consisting of SEQ ID NO. 60.

In this and other embodiments, the first β-thalassemia reagent mixture can comprise the 41-42M forward oligonucleotide primer consisting of SEQ ID NO. 25 in the concentration indicated in Table 2 (e.g., 0.9 µM). In these and other embodiments, the first β-thalassemia reagent mixture can comprise the 41-42M reverse oligonucleotide primer consisting of SEQ ID NO. 26 in the concentration indicated in Table 2 (e.g., 0.9 µM). Also, in these and other embodiments, the first β-thalassemia reagent mixture can comprise the 41-42M fluorescent normal probe comprising oligonucleotides consisting of SEQ ID NO. 59 in the concentration indicated in Table 2 (e.g., 0.25 µM) and the 41-42M fluorescent mutant probe comprising oligonucleotides consisting of SEQ ID NO. 60 in the concentration indicated in Table 2 (e.g., 0.25 µM).

In the same or different embodiment, the diagnostic kit can comprise another reagent mixture or a second β-thalassemia reagent mixture for detecting a β-thalassemia −28M mutation genotype. The second β-thalassemia reagent mixture can comprise the pre-formulated PCR master mix or PCR reaction mix previously disclosed in the concentrations indicated in Table 2. The primers and probes of the second β-thalassemia reagent mixture can comprise a −28M forward oligonucleotide primer consisting of SEQ ID NO. 27, a −28M reverse oligonucleotide primer consisting of SEQ ID NO. 28, a −28M fluorescent normal probe comprising oligonucleotides consisting of SEQ ID NO. 61, and a −28M fluorescent mutant probe comprising oligonucleotides consisting of SEQ ID NO. 62.

In this and other embodiments, the second β-thalassemia reagent mixture can comprise the −28M forward oligonucleotide primer consisting of SEQ ID NO. 27 in the concentration indicated in Table 2 (e.g., 0.9 µM). In these and other embodiments, the second β-thalassemia reagent mixture can comprise the −28M reverse oligonucleotide primer consisting of SEQ ID NO. 28 in the concentration indicated in Table 2 (e.g., 0.9 µM). Also, in these and other embodiments, the second β-thalassemia reagent mixture can comprise the −28M fluorescent normal probe comprising oligonucleotides consisting of SEQ ID NO. 61 in the concentration indicated in Table 2 (e.g., 0.25 µM) and the −28M fluorescent mutant probe comprising oligonucleotides consisting of SEQ ID NO. 62 in the concentration indicated in Table 2 (e.g., 0.25 µM).

In the same or different embodiment, the diagnostic kit can comprise another reagent mixture or a third β-thalassemia reagent mixture for detecting a β-thalassemia −29M mutation genotype. The third β-thalassemia reagent mixture can comprise the pre-formulated PCR master mix or PCR reaction mix previously disclosed in the concentrations indicated in Table 2. The primers and probes of the third β-thalassemia reagent mixture can comprise a −29M forward oligonucleotide primer consisting of SEQ ID NO. 55, a −29M reverse oligonucleotide primer consisting of SEQ ID NO. 56, a −29M fluorescent normal probe comprising oligonucleotides consisting of SEQ ID NO. 90, and a −29M fluorescent mutant probe comprising oligonucleotides consisting of SEQ ID NO. 91.

In this and other embodiments, the third β-thalassemia reagent mixture can comprise the −29M forward oligonucleotide primer consisting of SEQ ID NO. 55 in the concentration indicated in Table 2 (e.g., 0.9 µM). In these and other embodiments, the third β-thalassemia reagent mixture can comprise the −29M reverse oligonucleotide primer consisting of SEQ ID NO. 56 in the concentration indicated in Table 2 (e.g., 0.9 μM). Also, in these and other embodiments, the third β-thalassemia reagent mixture can comprise the −29M fluorescent normal probe comprising oligonucleotides consisting of SEQ ID NO. 90 in the concentration indicated in Table 2 (e.g., 0.25 μM) and the −29M fluorescent mutant probe comprising oligonucleotides consisting of SEQ ID NO. 91 in the concentration indicated in Table 2 (e.g., 0.25 μM).

In the same or different embodiment, the diagnostic kit can comprise another reagent mixture or a fourth β-thalassemia reagent mixture for detecting a β-thalassemia 17M point mutation genotype. The fourth β-thalassemia reagent mixture can comprise the pre-formulated PCR master mix or PCR reaction mix previously disclosed in the concentrations indicated in Table 2. The primers and probes of the fourth β-thalassemia reagent mixture can comprise a 17M forward oligonucleotide primer consisting of SEQ ID NO. 31, a 17M reverse oligonucleotide primer consisting of SEQ ID NO. 32, a 17M fluorescent normal probe comprising oligonucleotides consisting of SEQ ID NO. 65, and a 17M fluorescent mutant probe comprising oligonucleotides consisting of SEQ ID NO. 66.

In this and other embodiments, the fourth β-thalassemia reagent mixture can comprise the 17M forward oligonucleotide primer consisting of SEQ ID NO. 31 in the concentration indicated in Table 2 (e.g., 0.9 μM). In these and other embodiments, the fourth β-thalassemia reagent mixture can comprise the 17M reverse oligonucleotide primer consisting of SEQ ID NO. 32 in the concentration indicated in Table 2 (e.g., 0.9 μM). Also, in these and other embodiments, the fourth β-thalassemia reagent mixture can comprise the 17M fluorescent normal probe comprising oligonucleotides consisting of SEQ ID NO. 65 in the concentration indicated in Table 2 (e.g., 0.25 μM) and the 17M fluorescent mutant probe comprising oligonucleotides consisting of SEQ ID NO. 66 in the concentration indicated in Table 2 (e.g., 0.25 μM).

In the same or different embodiment, the diagnostic kit can comprise another reagent mixture or a fifth β-thalassemia reagent mixture for detecting a β-thalassemia 71-72M insertion mutation genotype. The fifth β-thalassemia reagent mixture can comprise the pre-formulated PCR master mix or PCR reaction mix previously disclosed in the concentrations indicated in Table 2. The primers and probes of the fifth β-thalassemia reagent mixture can comprise a 71-72 M forward oligonucleotide primer consisting of SEQ ID NO. 29, a 71-72M reverse oligonucleotide primer consisting of SEQ ID NO. 30, a 71-72M fluorescent normal probe comprising oligonucleotides consisting of SEQ ID NO. 63, and a 71-72M fluorescent mutant probe comprising oligonucleotides consisting of SEQ ID NO. 64.

In this and other embodiments, the fifth β-thalassemia reagent mixture can comprise the 71-72M forward oligonucleotide primer consisting of SEQ ID NO. 29 in the concentration indicated in Table 2 (e.g., 0.9 μM). In these and other embodiments, the fifth β-thalassemia reagent mixture can comprise the 71-72M reverse oligonucleotide primer consisting of SEQ ID NO. 30 in the concentration indicated in Table 2 (e.g., 0.9 μM). Also, in these and other embodiments, the fifth β-thalassemia reagent mixture can comprise the 71-72M fluorescent normal probe comprising oligonucleotides consisting of SEQ ID NO. 63 in the concentration indicated in Table 2 (e.g., 0.25 μM) and the 71-72M fluorescent mutant probe comprising oligonucleotides consisting of SEQ ID NO. 64 in the concentration indicated in Table 2 (e.g., 0.25 μM).

In the same or different embodiment, the diagnostic kit can comprise another reagent mixture or a sixth β-thalassemia reagent mixture for detecting a β-thalassemia βEM point mutation genotype. The sixth β-thalassemia reagent mixture can comprise the pre-formulated PCR master mix or PCR reaction mix previously disclosed in the concentrations indicated in Table 2. The primers and probes of the sixth β-thalassemia reagent mixture can comprise a βEM forward oligonucleotide primer consisting of SEQ ID NO. 33, a βEM reverse oligonucleotide primer consisting of SEQ ID NO. 34, a βEM fluorescent normal probe comprising oligonucleotides consisting of SEQ ID NO. 67, and a βEM fluorescent mutant probe comprising oligonucleotides consisting of SEQ ID NO. 68.

In this and other embodiments, the sixth β-thalassemia reagent mixture can comprise the βEM forward oligonucleotide primer consisting of SEQ ID NO. 33 in the concentration indicated in Table 2 (e.g., 0.9 μM). In these and other embodiments, the sixth β-thalassemia reagent mixture can comprise the βEM reverse oligonucleotide primer consisting of SEQ ID NO. 34 in the concentration indicated in Table 2 (e.g., 0.9 μM). Also, in these and other embodiments, the sixth β-thalassemia reagent mixture can comprise the βEM fluorescent normal probe comprising oligonucleotides consisting of SEQ ID NO. 67 in the concentration indicated in Table 2 (e.g., 0.25 μM) and the βEM fluorescent mutant probe comprising oligonucleotides consisting of SEQ ID NO. 68 in the concentration indicated in Table 2 (e.g., 0.25 μM).

In the same or different embodiment, the diagnostic kit can comprise another reagent mixture or a seventh β-thalassemia reagent mixture for detecting a β-thalassemia 654M point mutation genotype. The seventh β-thalassemia reagent mixture can comprise the pre-formulated PCR master mix or PCR reaction mix previously disclosed in the concentrations indicated in Table 2. The primers and probes of the seventh β-thalassemia reagent mixture can comprise a 654M forward oligonucleotide primer consisting of SEQ ID NO. 35, a 654M reverse oligonucleotide primer consisting of SEQ ID NO. 36, a 654M fluorescent normal probe comprising oligonucleotides consisting of SEQ ID NO. 69, and a 654M fluorescent mutant probe comprising oligonucleotides consisting of SEQ ID NO. 70.

In this and other embodiments, the seventh β-thalassemia reagent mixture can comprise the 654M forward oligonucleotide primer consisting of SEQ ID NO. 35 in the concentration indicated in Table 2 (e.g., 0.9 μM). In these and other embodiments, the seventh β-thalassemia reagent mixture can comprise the 654M reverse oligonucleotide primer consisting of SEQ ID NO. 36 in the concentration indicated in Table 2 (e.g., 0.9 μM). Also, in these and other embodiments, the seventh β-thalassemia reagent mixture can comprise the 654M fluorescent normal probe comprising oligonucleotides consisting of SEQ ID NO. 69 in the concentration indicated in Table 2 (e.g., 0.25 μM) and the 654M fluorescent mutant probe comprising oligonucleotides consisting of SEQ ID NO. 70 in the concentration indicated in Table 2 (e.g., 0.25 μM).

In the same or different embodiment, the diagnostic kit can comprise another reagent mixture or an eighth β-thalassemia reagent mixture for detecting a β-thalassemia 31M deletion genotype. The eighth β-thalassemia reagent mixture can comprise the pre-formulated PCR master mix or PCR reaction mix previously disclosed in the concentrations indicated in Table 2. The primers and probes of the eighth β-thalassemia reagent mixture can comprise a 31M forward oligonucleotide primer consisting of SEQ ID NO. 37, a 31M reverse oligonucleotide primer consisting of SEQ ID NO. 38, a 31M fluorescent normal probe comprising oligonucleotides consisting of SEQ ID NO. 71, and a 31M fluorescent mutant probe comprising oligonucleotides consisting of SEQ ID NO. 72.

In this and other embodiments, the eighth β-thalassemia reagent mixture can comprise the 31M forward oligonucleotide primer consisting of SEQ ID NO. 37 in the concentration indicated in Table 2 (e.g., 0.9 μM). In these and other embodiments, the eighth β-thalassemia reagent mixture can comprise the 31M reverse oligonucleotide primer consisting of SEQ ID NO. 38 in the concentration indicated in Table 2 (e.g., 0.9 μM). Also, in these and other embodiments, the eighth β-thalassemia reagent mixture can comprise the 31M fluorescent normal probe comprising oligonucleotides consisting of SEQ ID NO. 71 in the concentration indicated in Table 2 (e.g., 0.25 μM) and the 31M fluorescent mutant probe comprising oligonucleotides consisting of SEQ ID NO. 72 in the concentration indicated in Table 2 (e.g., 0.25 μM).

In the same or different embodiment, the diagnostic kit can comprise another reagent mixture or a ninth β-thalassemia reagent mixture for detecting a β-thalassemia 14-15M insertion mutation genotype. The ninth β-thalassemia reagent mixture can comprise the pre-formulated PCR master mix or PCR reaction mix previously disclosed in the concentrations indicated in Table 2. The primers and probes of the ninth β-thalassemia reagent mixture can comprise a 14-15M forward oligonucleotide primer consisting of SEQ ID NO. 39, a 14-15M reverse oligonucleotide primer consisting of SEQ ID NO. 40, a 14-15M fluorescent normal probe comprising oligonucleotides consisting of SEQ ID NO. 73, and a 14-15M fluorescent mutant probe comprising oligonucleotides consisting of SEQ ID NO. 74.

In this and other embodiments, the ninth β-thalassemia reagent mixture can comprise the 14-15M forward oligonucleotide primer consisting of SEQ ID NO. 39 in the concentration indicated in Table 2 (e.g., 0.9 μM). In these and other embodiments, the ninth β-thalassemia reagent mixture can comprise the 14-15M reverse oligonucleotide primer consisting of SEQ ID NO. 40 in the concentration indicated in Table 2 (e.g., 0.9 μM). Also, in these and other embodiments, the ninth β-thalassemia reagent mixture can comprise the 14-15M fluorescent normal probe comprising oligonucleotides consisting of SEQ ID NO. 73 in the concentration indicated in Table 2 (e.g., 0.25 μM) and the 14-15M fluorescent mutant probe comprising oligonucleotides consisting of SEQ ID NO. 74 in the concentration indicated in Table 2 (e.g., 0.25 μM).

In the same or different embodiment, the diagnostic kit can comprise another reagent mixture or a tenth β-thalassemia reagent mixture for detecting a β-thalassemia 43M point mutation genotype. The tenth β-thalassemia reagent mixture can comprise the pre-formulated PCR master mix or PCR reaction mix previously disclosed in the concentrations indicated in Table 2. The primers and probes of the tenth β-thalassemia reagent mixture can comprise a 43M forward oligonucleotide primer consisting of SEQ ID NO. 41, a 43M reverse oligonucleotide primer consisting of SEQ ID NO. 42, a 43M fluorescent normal probe comprising oligonucleotides consisting of SEQ ID NO. 75, and a 43M fluorescent mutant probe comprising oligonucleotides consisting of SEQ ID NO. 76.

In this and other embodiments, the tenth β-thalassemia reagent mixture can comprise the 43M forward oligonucleotide primer consisting of SEQ ID NO. 41 in the concentration indicated in Table 2 (e.g., 0.9 μM). In these and other embodiments, the tenth β-thalassemia reagent mixture can comprise the 43M reverse oligonucleotide primer consisting of SEQ ID NO. 42 in the concentration indicated in Table 2 (e.g., 0.9 μM). Also, in these and other embodiments, the tenth β-thalassemia reagent mixture can comprise the 43M fluorescent normal probe comprising oligonucleotides consisting of SEQ ID NO. 75 in the concentration indicated in Table 2 (e.g., 0.25 μM) and the 43M fluorescent mutant probe comprising oligonucleotides consisting of SEQ ID NO. 76 in the concentration indicated in Table 2 (e.g., 0.25 μM).

In the same or different embodiment, the diagnostic kit can comprise another reagent mixture or an eleventh β-thalassemia reagent mixture for detecting a β-thalassemia 27/28M insertion mutation genotype. The eleventh β-thalassemia reagent mixture can comprise the pre-formulated PCR master mix or PCR reaction mix previously disclosed in the concentrations indicated in Table 2. The primers and probes of the eleventh β-thalassemia reagent mixture can comprise a 27/28M forward oligonucleotide primer consisting of SEQ ID NO. 43, a 27/28M reverse oligonucleotide primer consisting of SEQ ID NO. 44, a 27/28M fluorescent normal probe comprising oligonucleotides consisting of SEQ ID NO. 77, and a 27/28M fluorescent mutant probe comprising oligonucleotides consisting of SEQ ID NO. 78.

In this and other embodiments, the eleventh β-thalassemia reagent mixture can comprise the 27/28M forward oligonucleotide primer consisting of SEQ ID NO. 43 in the concentration indicated in Table 2 (e.g., 0.9 μM). In these and other embodiments, the eleventh β-thalassemia reagent mixture can comprise the 27/28M reverse oligonucleotide primer consisting of SEQ ID NO. 44 in the concentration indicated in Table 2 (e.g., 0.9 μM). Also, in these and other embodiments, the eleventh β-thalassemia reagent mixture can comprise the 27/28M fluorescent normal probe comprising oligonucleotides consisting of SEQ ID NO. 77 in the concentration indicated in Table 2 (e.g., 0.25 μM) and the 27/28M fluorescent mutant probe comprising oligonucleotides consisting of SEQ ID NO. 78 in the concentration indicated in Table 2 (e.g., 0.25 μM).

In the same or different embodiment, the diagnostic kit can comprise another reagent mixture or a twelfth β-thalassemia reagent mixture for detecting a β-thalassemia IVS-I-1M point mutation genotype. The twelfth β-thalassemia reagent mixture can comprise the pre-formulated PCR master mix or PCR reaction mix previously disclosed in the concentrations indicated in Table 2. The primers and probes of the twelfth β-thalassemia reagent mixture can comprise an IVS-I-1M forward oligonucleotide primer consisting of SEQ ID NO. 45, an IVS-I-1M reverse oligonucleotide primer consisting of SEQ ID NO. 46, an IVS-I-1M fluorescent normal probe comprising oligonucleotides consisting of SEQ ID NO. 79, a first IVS-I-1M fluorescent mutant probe comprising oligonucleotides consisting of SEQ ID NO. 80, and a second IVS-I-1M fluorescent mutation probe comprising oligonucleotides consisting of SEQ ID NO. 81.

In this and other embodiments, the twelfth β-thalassemia reagent mixture can comprise the IVS-I-1M forward oligonucleotide primer consisting of SEQ ID NO. 45 in the concentration indicated in Table 2 (e.g., 0.9 μM). In these and other embodiments, the twelfth β-thalassemia reagent mixture can comprise the IVS-I-1M reverse oligonucleotide primer consisting of SEQ ID NO. 46 in the concentration indicated in Table 2 (e.g., 0.9 μM). Also, in these and other embodiments, the twelfth β-thalassemia reagent mixture can comprise the IVS-I-1M fluorescent normal probe comprising oligonucleotides consisting of SEQ ID NO. 79 in the concentration indicated in Table 2 (e.g., 0.25 µM) and the first IVS-I-1M fluorescent mutant probe comprising oligonucleotides consisting of SEQ ID NO. 80 and the second IVS-I-1M fluorescent mutant probe comprising oligonucleotides consisting of SEQ ID NO. 81 in a total concentration of 0.25 µM.

In the same or different embodiment, the diagnostic kit can comprise another reagent mixture or a thirteenth β-thalassemia reagent mixture for detecting a β-thalassemia IVS-I-5M point mutation genotype. The thirteenth β-thalassemia reagent mixture can comprise the pre-formulated PCR master mix or PCR reaction mix previously disclosed in the concentrations indicated in Table 2. The primers and probes of the thirteenth β-thalassemia reagent mixture can comprise a IVS-I-5M forward oligonucleotide primer consisting of SEQ ID NO. 47, an IVS-I-5M reverse oligonucleotide primer consisting of SEQ ID NO. 48, an IVS-I-5M fluorescent normal probe comprising oligonucleotides consisting of SEQ ID NO. 82, and an IVS-I-5M fluorescent mutant probe comprising oligonucleotides consisting of SEQ ID NO. 83.

In this and other embodiments, the thirteenth β-thalassemia reagent mixture can comprise the IVS-I-5M forward oligonucleotide primer consisting of SEQ ID NO. 47 in the concentration indicated in Table 2 (e.g., 0.9 µM). In these and other embodiments, the thirteenth β-thalassemia reagent mixture can comprise the IVS-I-5M reverse oligonucleotide primer consisting of SEQ ID NO. 48 in the concentration indicated in Table 2 (e.g., 0.9 µM). Also, in these and other embodiments, the thirteenth β-thalassemia reagent mixture can comprise the IVS-I-5M fluorescent normal probe comprising oligonucleotides consisting of SEQ ID NO. 82 in the concentration indicated in Table 2 (e.g., 0.25 µM) and the IVS-I-5M fluorescent mutant probe comprising oligonucleotides consisting of SEQ ID NO. 83 in the concentration indicated in Table 2 (e.g., 0.25 µM).

In the same or different embodiment, the diagnostic kit can comprise another reagent mixture or a fourteenth β-thalassemia reagent mixture for detecting a β-thalassemia CAPM genotype. The fourteenth β-thalassemia reagent mixture can comprise the pre-formulated PCR master mix or PCR reaction mix previously disclosed in the concentrations indicated in Table 2. The primers and probes of the fourteenth β-thalassemia reagent mixture can comprise a CAPM forward oligonucleotide primer consisting of SEQ ID NO. 49, a CAPM reverse oligonucleotide primer consisting of SEQ ID NO. 50, a CAPM fluorescent normal probe comprising oligonucleotides consisting of SEQ ID NO. 84, and a CAPM fluorescent mutant probe comprising oligonucleotides consisting of SEQ ID NO. 85.

In this and other embodiments, the fourteenth β-thalassemia reagent mixture can comprise the CAPM forward oligonucleotide primer consisting of SEQ ID NO. 49 in the concentration indicated in Table 2 (e.g., 0.9 µM). In these and other embodiments, the fourteenth β-thalassemia reagent mixture can comprise the CAPM reverse oligonucleotide primer consisting of SEQ ID NO. 50 in the concentration indicated in Table 2 (e.g., 0.9 µM). Also, in these and other embodiments, the fourteenth β-thalassemia reagent mixture can comprise the CAPM fluorescent normal probe comprising oligonucleotides consisting of SEQ ID NO. 84 in the concentration indicated in Table 2 (e.g., 0.25 µM) and the CAPM fluorescent mutant probe comprising oligonucleotides consisting of SEQ ID NO. 85 in the concentration indicated in Table 2 (e.g., 0.25 µM).

In the same or different embodiment, the diagnostic kit can comprise another reagent mixture or a fifteenth β-thalassemia reagent mixture for detecting a β-thalassemia IntM point mutation genotype. The fifteenth β-thalassemia reagent mixture can comprise the pre-formulated PCR master mix or PCR reaction mix previously disclosed in the concentrations indicated in Table 2. The primers and probes of the fifteenth β-thalassemia reagent mixture can comprise a IntM forward oligonucleotide primer consisting of SEQ ID NO. 51, an IntM reverse oligonucleotide primer consisting of SEQ ID NO. 52, an IntM fluorescent normal probe comprising oligonucleotides consisting of SEQ ID NO. 86, and an IntM fluorescent mutant probe comprising oligonucleotides consisting of SEQ ID NO. 87.

In this and other embodiments, the fifteenth β-thalassemia reagent mixture can comprise the IntM forward oligonucleotide primer consisting of SEQ ID NO. 51 in the concentration indicated in Table 2 (e.g., 0.9 µM). In these and other embodiments, the fifteenth β-thalassemia reagent mixture can comprise the IntM reverse oligonucleotide primer consisting of SEQ ID NO. 52 in the concentration indicated in Table 2 (e.g., 0.9 µM). Also, in these and other embodiments, the fifteenth β-thalassemia reagent mixture can comprise the IntM fluorescent normal probe comprising oligonucleotides consisting of SEQ ID NO. 86 in the concentration indicated in Table 2 (e.g., 0.25 µM) and the IntM fluorescent mutant probe comprising oligonucleotides consisting of SEQ ID NO. 87 in the concentration indicated in Table 2 (e.g., 0.25 µM).

In the same or different embodiment, the diagnostic kit can comprise another reagent mixture or a sixteenth β-thalassemia reagent mixture for detecting a β-thalassemia −30M point mutation genotype. The sixteenth β-thalassemia reagent mixture can comprise the pre-formulated PCR master mix or PCR reaction mix previously disclosed in the concentrations indicated in Table 2. The primers and probes of the sixteenth β-thalassemia reagent mixture can comprise a −30M forward oligonucleotide primer consisting of SEQ ID NO. 53, a −30M reverse oligonucleotide primer consisting of SEQ ID NO. 54, a −30M fluorescent normal probe comprising oligonucleotides consisting of SEQ ID NO. 88, and a −30M fluorescent mutant probe comprising oligonucleotides consisting of SEQ ID NO. 89.

In this and other embodiments, the sixteenth β-thalassemia reagent mixture can comprise the −30M forward oligonucleotide primer consisting of SEQ ID NO. 53 in the concentration indicated in Table 2 (e.g., 0.9 µM). In these and other embodiments, the sixteenth β-thalassemia reagent mixture can comprise the −30M reverse oligonucleotide primer consisting of SEQ ID NO. 54 in the concentration indicated in Table 2 (e.g., 0.9 µM). Also, in these and other embodiments, the sixteenth β-thalassemia reagent mixture can comprise the −30M fluorescent normal probe comprising oligonucleotides consisting of SEQ ID NO. 88 in the concentration indicated in Table 2 (e.g., 0.25 µM) and the −30M fluorescent mutant probe comprising oligonucleotides consisting of SEQ ID NO. 89 in the concentration indicated in Table 2 (e.g., 0.25 µM).

In the same or different embodiment, the diagnostic kit can comprise another reagent mixture or a seventeenth β-thalassemia reagent mixture for detecting a β-thalassemia −32M point mutation genotype. The seventeenth β-thalassemia reagent mixture can comprise the pre-formulated PCR master mix or PCR reaction mix previously disclosed in the concentrations indicated in Table 2. The primers and probes of the seventeenth β-thalassemia reagent mixture can comprise a −32M forward oligonucleotide primer consisting of SEQ ID NO. 57, a −32M reverse oligonucleotide primer consisting of SEQ ID NO. 58, a −32M fluorescent normal probe comprising oligonucleotides consisting of SEQ ID NO. 92, and a −32M fluorescent mutant probe comprising oligonucleotides consisting of SEQ ID NO. 93.

In this and other embodiments, the seventeenth β-thalassemia reagent mixture can comprise the −32M forward oligonucleotide primer consisting of SEQ ID NO. 57 in the concentration indicated in Table 2 (e.g., 0.9 µM). In these and other embodiments, the seventeenth β-thalassemia reagent mixture can comprise the −32M reverse oligonucleotide primer consisting of SEQ ID NO. 58 in the concentration indicated in Table 2 (e.g., 0.9 µM). Also, in these and other embodiments, the seventeenth β-thalassemia reagent mixture can comprise the −32M fluorescent normal probe comprising oligonucleotides consisting of SEQ ID NO. 92 in the concentration indicated in Table 2 (e.g., 0.25 µM) and the −32M fluorescent mutant probe comprising oligonucleotides consisting of SEQ ID NO. 93 in the concentration indicated in Table 2 (e.g., 0.25 µM).

In the same or different embodiment, the diagnostic kit can comprise another reagent mixture or an eighteenth β-thalassemia reagent mixture for detecting a β-thalassemia CD37M point mutation genotype. The eighteenth β-thalassemia reagent mixture can comprise the pre-formulated PCR master mix or PCR reaction mix previously disclosed in the concentrations indicated in Table 2. The primers and probes of the eighteenth β-thalassemia reagent mixture can comprise a CD37M forward oligonucleotide primer consisting of SEQ ID NO. 94, a CD37M reverse oligonucleotide primer consisting of SEQ ID NO. 95, a CD37M fluorescent normal probe comprising oligonucleotides consisting of SEQ ID NO. 103 and a CD37M fluorescent mutant probe comprising oligonucleotides consisting of SEQ ID NO. 102.

In this and other embodiments, the eighteenth β-thalassemia reagent mixture can comprise the CD37M forward oligonucleotide primer consisting of SEQ ID NO. 94 in the concentration indicated in Table 2 (e.g., 0.9 µM). In these and other embodiments, the eighteenth β-thalassemia reagent mixture can comprise the CD37M reverse oligonucleotide primer consisting of SEQ ID NO. 95 in the concentration indicated in Table 2 (e.g., 0.9 µM). Also, in these and other embodiments, the eighteenth β-thalassemia reagent mixture can comprise the CD37M fluorescent normal probe comprising oligonucleotides consisting of SEQ ID NO. 103 in the concentration indicated in Table 2 (e.g., 0.25 µM) and the CD37M fluorescent mutant probe comprising oligonucleotides consisting of SEQ ID NO. 102 in the concentration indicated in Table 2 (e.g., 0.25 µM).

In the same or different embodiment, the diagnostic kit can comprise another reagent mixture or a nineteenth β-thalassemia reagent mixture for detecting a β-thalassemia 90M genotype. The nineteenth β-thalassemia reagent mixture can comprise the pre-formulated PCR master mix or PCR reaction mix previously disclosed in the concentrations indicated in Table 2. The primers and probes of the nineteenth β-thalassemia reagent mixture can comprise a 90M forward oligonucleotide primer consisting of SEQ ID NO. 96, a 90M reverse oligonucleotide primer consisting of SEQ ID NO. 97, a 90M fluorescent normal probe comprising oligonucleotides consisting of SEQ ID NO. 105, and a 90M fluorescent mutant probe comprising oligonucleotides consisting of SEQ ID NO. 104.

In this and other embodiments, the nineteenth β-thalassemia reagent mixture can comprise the 90M forward oligonucleotide primer consisting of SEQ ID NO. 96 in the concentration indicated in Table 2 (e.g., 0.9 µM). In these and other embodiments, the nineteenth β-thalassemia reagent mixture can comprise the 90M reverse oligonucleotide primer consisting of SEQ ID NO. 97 in the concentration indicated in Table 2 (e.g., 0.9 µM). Also, in these and other embodiments, the nineteenth β-thalassemia reagent mixture can comprise the 90M fluorescent normal probe comprising oligonucleotides consisting of SEQ ID NO. 105 in the concentration indicated in Table 2 (e.g., 0.25 µM) and the 90M fluorescent mutant probe comprising oligonucleotides consisting of SEQ ID NO. 104 in the concentration indicated in Table 2 (e.g., 0.25 µM).

In the same or different embodiment, the diagnostic kit can comprise another reagent mixture or a twentieth β-thalassemia reagent mixture for detecting a β-thalassemia IVS-II-5M genotype. The twentieth β-thalassemia reagent mixture can comprise the pre-formulated PCR master mix or PCR reaction mix previously disclosed in the concentrations indicated in Table 2. The primers and probes of the twentieth β-thalassemia reagent mixture can comprise an IVS-II-5M forward oligonucleotide primer consisting of SEQ ID NO. 98, an IVS-II-5M reverse oligonucleotide primer consisting of SEQ ID NO. 99, an IVS-II-5M fluorescent normal probe comprising oligonucleotides consisting of SEQ ID NO. 107, and an IVS-II-5M fluorescent mutant probe comprising oligonucleotides consisting of SEQ ID NO. 106.

In this and other embodiments, the twentieth β-thalassemia reagent mixture can comprise the IVS-II-5M forward oligonucleotide primer consisting of SEQ ID NO. 98 in the concentration indicated in Table 2 (e.g., 0.9 µM). In these and other embodiments, the twentieth β-thalassemia reagent mixture can comprise the IVS-II-5M reverse oligonucleotide primer consisting of SEQ ID NO. 99 in the concentration indicated in Table 2 (e.g., 0.9 µM). Also, in these and other embodiments, the twentieth β-thalassemia reagent mixture can comprise the IVS-II-5M fluorescent normal probe comprising oligonucleotides consisting of SEQ ID NO. 107 in the concentration indicated in Table 2 (e.g., 0.25 µM) and the IVS-II-5M fluorescent mutant probe comprising oligonucleotides consisting of SEQ ID NO. 106 in the concentration indicated in Table 2 (e.g., 0.25 µM).

Any of the reagent mixtures disclosed in the preceding sections can be an aqueous mixture contained in a single reaction vessel or tube or as one well of a multi-well plate. As will be discussed in the following sections, any of the reagent mixtures can be pre-spotted in lyophilized form in a single well of a multi-well PCR plate, such as a 96-well or a 384-well plate.

Pre-Spotted Multiwell Plates

Disclosed herein is one embodiment of a diagnostic kit having the PCR reagents or reagent mixtures described in the preceding sections pre-spotted on wells of a multi-well plate. For example, the multi-well plate can be a 384-well plate or a 96-well plate. The multi-well plates can be PCR-compatible plates having reaction wells capable of being read by a high-throughput PCR instrument such as a CFX96 Touch™ Real-Time PCR Detection System from Bio-Rad®, a CFX384 Touch™ Real-Time PCR Detection System from Bio-Rad®, a CFX Connect™ Real-Time PCR Detection System from Bio-Rad®, or a LightCycler® 480 Instrument II from Roche®. In some embodiments, the multi-well plate can be skirted, semi-skirted, or unskirted. In these and other embodiments, the multi-well plate can have high-profile reaction wells, low-profile reaction wells, or a combination thereof.

The multi-well plate can have any of the reagent mixtures described in the preceding sections pre-spotted or pre-aliquoted within wells of the multi-well plate. For example, the multi-well plate can have the reagent mixtures pre-aliquoted as aqueous mixtures within the wells of the multi-well plate. Alternatively, FIG. 1 shows a top plan view of a 384-well multi-well plate 100 having reagent mixtures pre-spotted in lyophilized form 102 within each well 104.

In one or more embodiments, all wells within the same column of the multi-well plate 100 can contain the same reagent mixture with different columns of the multi-well plate 100 containing different reagent mixtures. For example, all wells in column 1 can contain the first α-thalassemia reagent mixture configured to detect an α-thalassemia −α3.7 deletion genotype or an α-thalassemia −α4.2 deletion genotype in a patient DNA template. Also, in this example, all wells in columns 2, 3, 4, 5, and 6 can contain the second α-thalassemia reagent mixture, the third α-thalassemia reagent mixture, the fourth α-thalassemia reagent mixture, the fifth α-thalassemia reagent mixture, and the sixth α-thalassemia reagent mixture, respectively. In this and other examples, all wells in columns 7 to 23 can contain any of the β-thalassemia reagent mixtures including any of the first through twentieth β-thalassemia reagent mixtures.

In some embodiments, the wells in column 24 can be reserved for PCR reagent mixtures designed for a housekeeping gene such as the human RNase P gene. For example, all wells in column 24 can contain a PCR reagent mixture comprising the PCR master mix disclosed above and primers and probes for the human RNase P gene. The human RNase P gene can be used as a positive control to monitor sample quality and to detect for inhibitors of the PCR reaction.

Isolated patient DNA or template DNA from multiple patients or samples can then be added to each row of wells 104 such that each row of wells represents template DNA from a different patient or sample. For example, the wells 104 in row A of the multi-well plate 100 can receive template DNA from patient 1 or sample 1 and the wells 104 in row B of the multi-well plate 100 can receive template DNA from patient 2 or sample 2. Row P of the multi-well plate 100 can be set aside as a no template control (NTC) to monitor for contaminations. By reserving different rows of the multi-well plate 100 for different patients or samples, the multi-well plate 100 can be used as part of a high-throughput thalassemia detection system.

Patient or template DNA can be isolated or extracted from patient blood or other bodily fluids. One unexpected advantage of the kits, reagents, and methods described herein is that they are also effective in detecting thalassemia genotypes in DNA extracted from bodily fluids other than blood including amniotic fluid, samples derived from chorionic villus sampling (CVS), and samples derived from saliva or other patient swabs.

Real-Time PCR Protocol

After adding isolated patient or template DNA to the various wells, the multi-well plate 100 can then be placed into one of the high-throughput PCR instruments disclosed in the preceding sections (e.g., the CFX96 Touch™ Real-Time PCR Detection System) and subject to a real-time PCR protocol comprising the steps of pre-reaction incubation, pre-denaturation, denaturation, annealing, and fluorescence collection. More specifically, the real-time PCR protocol can comprise the steps of incubating the PCR reagent mixtures at between about 49° C. and 51° C. (e.g., 50° C.) for about 1 to 3 minutes (e.g., about 2 minutes); activating the enzyme at about 95° C. in a pre-denaturation step for about 1 to 10 minutes (e.g., about 1 minute); denaturing the product at between about 94° C. to about 96° C. for between about 12 seconds to 20 seconds; allowing the probes to specifically hybridize to the amplicon during the annealing and extension steps at between about 55° C. to about 62° C. for about 0.5 minutes to 1.5 minutes; and repeating the denaturing and annealing steps for about 30 to 50 cycles. One or more fluorescence signals from the multi-well plate 100 can then be collected during each annealing step.

Method of Detection

Figure 2:
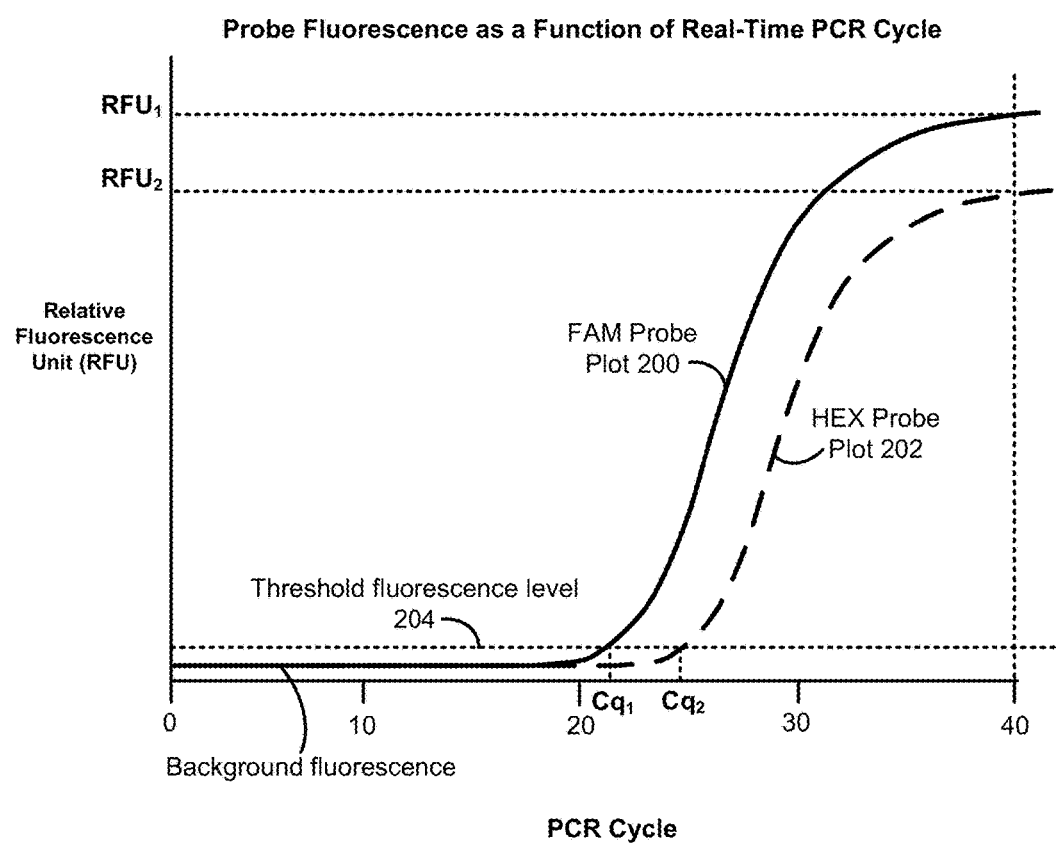
FIG. 2 illustrates an example graph of probe fluorescence as a function of PCR amplification cycle.

FIG. 2 illustrates an example graph of probe fluorescence as a function of PCR amplification cycle. For example, FIG. 2 can be generated by the software program of a high-throughput PCR instrument such as the CFX Manager™ software tool provided by Bio-Rad®. In other embodiments, the software program can be any software program capable of receiving raw fluorescence data and cycle information from a real-time PCR instrument. As shown in FIG. 2, the PCR cycle number is shown along the x-axis and the fluorescence or relative fluorescence (in Relative Fluorescence Units (RFUs)) of the amplification reaction is shown along the y-axis. The fluorescence level is proportional to the amount of amplified product in the reaction well, tube, or vessel.

FIG. 2 illustrates two amplification plots for two separate probes having different fluorescent reporters attached to each probe. For example, plot 200 shows the fluorescence level or signal of a probe having a 6-carboxy-fluorescein (FAM) fluorophore coupled to the probe. In addition, plot 202 shows the fluorescence level or signal of a probe having a hexachloro-6-carboxy-fluorescein (HEX) fluorophore coupled to the probe. As shown in FIG. 2, the fluorescence levels of both probes initially remain at background levels until enough amplified product accumulates to yield a detectable fluorescence signal. The detectable fluorescence signal can be a fluorescence level reaching a threshold fluorescence level 204. In one embodiment, the threshold fluorescence level 204 can be set by the software program of the high-throughput PCR instrument or by a user. The cycle number at which the amplification plot intersects the threshold fluorescence level 204 is known as a quantification cycle (Cq). The Cq is also referred to as a threshold cycle (Ct), a crossing point (Cp), or a take-off point (TOP). The Cq value represents the number of cycles needed to reach a set threshold fluorescence signal level. As shown in FIG. 2, the Cq value of one probe (e.g., $Cq_1$ of the probe having the FAM reporter) can be different than the Cq value of another probe (e.g., $Cq_2$ of the probe having the HEX reporter). Since the amount of PCR product approximately doubles in each real-time PCR cycle, the difference in Cq values can represent a significant difference in the amount of target DNA detected in the reaction well, tube, or vessel. As will be discussed in the following sections, one method of detecting the presence of certain thalassemia genotypes is by analyzing the difference in Cq values (or ΔCq) between two probe amplification plots.

FIG. 2 also illustrates that the fluorescence levels or relative fluorescence levels of the two amplification plots can differ at certain cycles. For example, the fluorescence level of plot 200 can be at $RFU_1$ at cycle 40 and the fluorescence level of plot 202 can be at $RFU_2$ at cycle 40. As will be discussed in the following sections, one method of detecting the presence of certain thalassemia genotypes is by analyzing the ratio of RFU values at certain cycles (e.g., cycle 40).

Figure 3A:
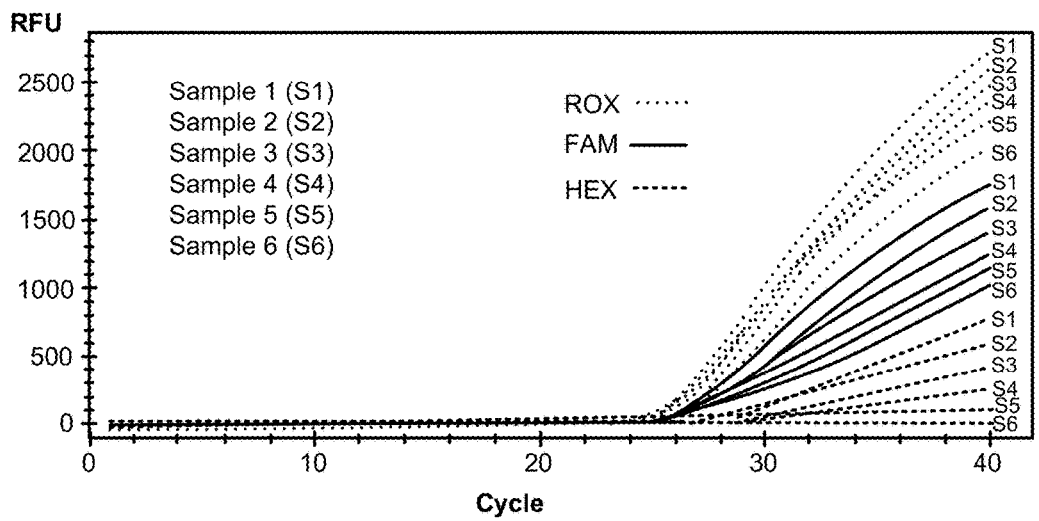
FIG. 3A illustrates amplification plots of DNA extracted or isolated from six patient samples.

FIG. 3A illustrates amplification plots of DNA extracted or isolated from six patient samples (samples 1-6). For example, the samples 1 through 6 can be injected, pipetted, or otherwise introduced to wells A1, B1, C1, D1, E1, and F1 of the multi-well plate 100 of FIG. 1 where each of such wells contain the first α-thalassemia reagent mixture for detecting the α-thalassemia −α3.7 deletion genotype or the α-thalassemia −α4.2 deletion genotype. The samples 1 through 6 can also be introduced to other wells of the multi-well plate 100 depending on the arrangement of the first α-thalassemia reagent mixture within the multi-well plate 100.

The amplification plots of FIG. 3A can be generated by the software program of the high-throughput PCR instrument (e.g., CFX Manager™ provided by Bio-Rad®). Each of the samples 1 through 6 can have three plots associated with the sample. The three plots can include the tracked fluorescence signals of the ROX, FAM, and HEX fluorophores in each reaction well, vessel, or tube. As indicated in Tables 3 and 4, the ROX reporter or fluorophore can be coupled to the LIS1 probe, the FAM reporter or fluorophore can be coupled to the α1 probe, and the HEX reporter or fluorophore can be coupled to the α2 probe. Although all three probe amplification plots for Samples 1 through 6 (18 plots total) are displayed in the example graph of FIG. 3A, it should be understood by one of ordinary skill in the art that the software program can display singular plots or any combination of plots to a user of the high-throughput PCR instrument.

In one embodiment, a method of detecting an −α3.7 large fragment deletion or an −α4.2 large fragment deletion genotype within each sample can comprise the following steps: (1) calculating a ΔCq between the FAM reporter (of the α1 probe) and the ROX reporter (of the LIS1 or internal reference gene probe) as shown in Equation 1 below (hereinafter known as an "α1ΔCq"), (2) calculating a ΔCq between the HEX reporter (of the α2 probe) and the ROX reporter (of the LIS1 or internal reference gene probe) as shown in Equation 2 below (hereinafter known as an "α2ΔCq"), and diagnosing the template or patient DNA within the sample as (i) heterozygous −α3.7/αα, (ii) heterozygous −α4.2/αα, or (iii) homozygous αα/αα if the conditions set forth in Conditions 1, 2, and 3 below are satisfied.

$$\alpha1\Delta Cq = Cq(FAM) - Cq(ROX) \quad \text{Equation 1:}$$

$$\alpha2\Delta Cq = Cq(HEX) - Cq(ROX) \quad \text{Equation 2:}$$

Condition 1: If α1ΔCq≥1.5 and α2ΔCq≥2.0, then genotype is −α3.7/αα

Condition 2: If 0.5≤α1ΔCq≤1.5 and α2ΔCq≥2.0, then genotype is −α4.2/αα

Condition 3: If 0.5≤α1ΔCq≤1.5 and α2ΔCq<2.0, then genotype is αα/αα

In an alternative embodiment, the detection method can also use the below conditions 4, 5, and 6 to make a diagnosis of the template or patient DNA as (i) heterozygous −α3.7/αα, (ii) heterozygous −α4.2/αα, or (iii) homozygous ac/αα:

Condition 4: If α1ΔCq≈2.0 and α2ΔCq≈2.0, then genotype is −α3.7/αα

Condition 5: If α1ΔCq≈1.0 and α2ΔCq≈2.0, then genotype is −α4.2/αα

Condition 6: If α1ΔCq≈1.0 and α2ΔCq≈1.0, then genotype is αα/αα or not −α3.7/αα and not −α4.2/αα

Figure 3B:
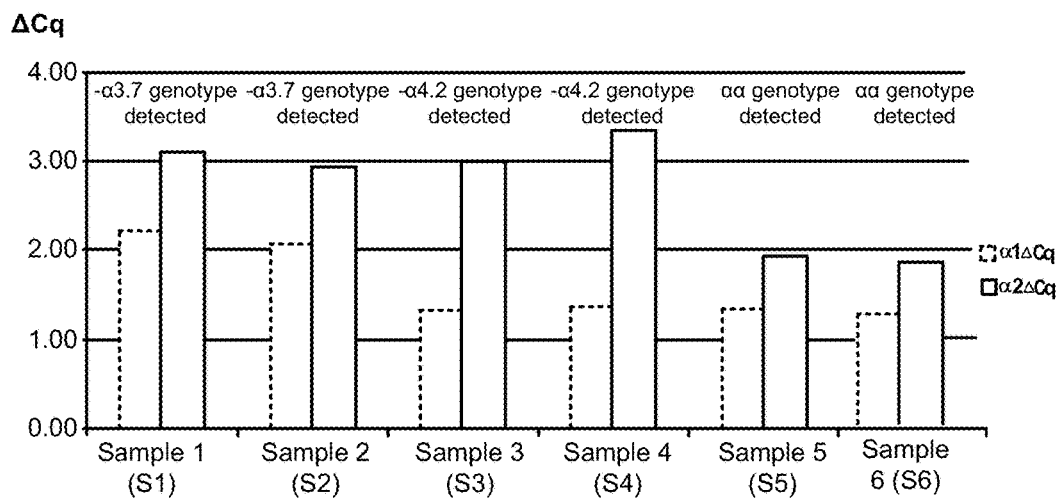
FIG. 3B illustrates a bar graph showing the results of a detection using certain methods and kits described herein.

FIG. 3B illustrates a bar graph showing the results of the detection based on the amplification plots of FIG. 3A. As shown in FIG. 3B, samples 1 and 2 were detected as samples from patients likely having the −α3.7/αα large fragment deletion genotype, samples 3 and 4 were detected as samples from patients likely having the −α4.2/αα large fragment deletion genotype, and samples 5 and 6 were detected as samples from patients likely not having the −α3.7/αα or the −α4.2/αα genotype or having the normal or wild-type αα/αα genotype. In some embodiments, such detection methods can be performed by a laboratory technician or medical professional. In other embodiments, such detection methods can be implemented as machine-executable software instructions programmed to run on a computer, a portable or handheld device such as a tablet or smartphone, a PCR instrument, or any combination thereof.

Figure 4:
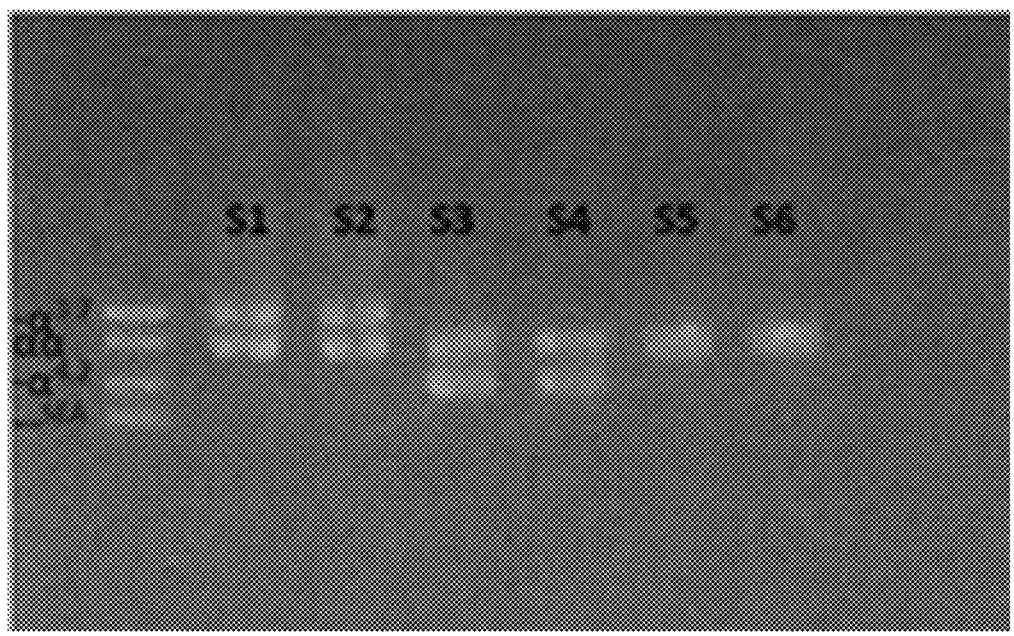
FIG. 4 is an annotated photograph of a gel electrophoresis corroborating the results of detection performed using the methods and kits described herein.

FIG. 4 illustrates an annotated photograph of a gel electrophoresis showing the results of the same samples 1 through 6 described in the preceding sections diagnosed using Gap-PCR followed by gel electrophoresis. As shown in FIG. 4, the traditional method of using Gap-PCR followed by gel electrophoresis confirmed samples 1 and 2 as the heterozygous −α3.7/αα genotype, samples 3 and 4 as the heterozygous −α4.2/αα, and samples 5 and 6 as the normal or wild-type αα/αα genotype.

Figure 5A:
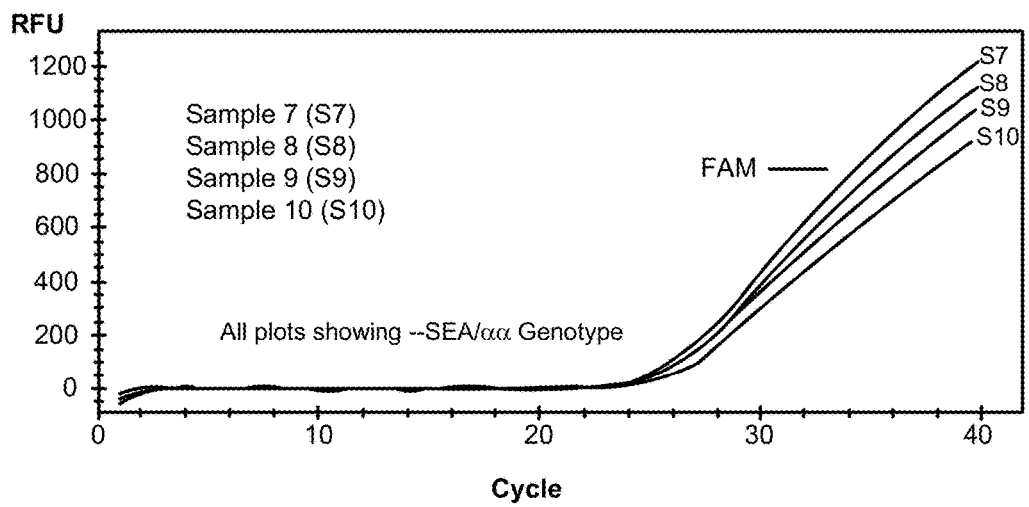
FIG. 5A illustrates amplification plots of DNA extracted or isolated from four patient samples.

FIG. 5A illustrates amplification plots of DNA extracted or isolated from four patient samples (e.g., samples 7-10). For example, the samples 7 through 10 can be injected, pipetted, or otherwise introduced to wells G2, H2, I2, and J2 of the multi-well plate 100 of FIG. 1 where each of such wells contain the second α-thalassemia reagent mixture for detecting the α-thalassemia −−SEA (or −−$^{SEA}$) deletion genotype. The samples 7 through 10 can also be introduced to other wells of the multi-well plate 100 depending on the arrangement of the second α-thalassemia reagent mixture within the multi-well plate 100.

Figure 5B:
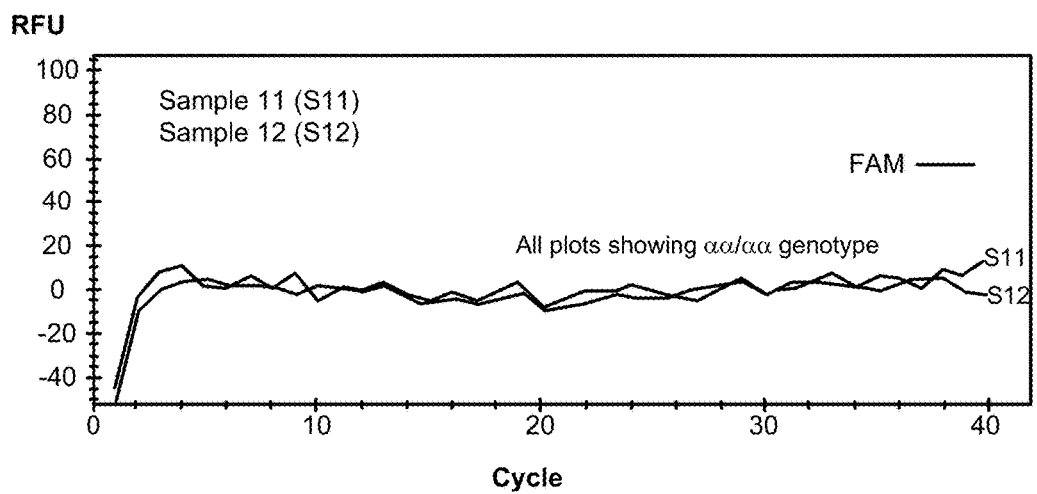
FIG. 5B illustrates amplification plots of DNA extracted or isolated from two patient samples.

FIG. 5B illustrates amplification plots of DNA extracted or isolated from two patient samples (e.g., samples 11 and 12). For example, the samples 11 and 12 can be injected, pipetted, or otherwise introduced to wells K2 and L2 of the multi-well plate 100 of FIG. 1 where each of such wells contain the second α-thalassemia reagent mixture for detecting the α-thalassemia −−SEA (or −−$^{SEA}$) deletion genotype. The samples 11 and 12 can also be introduced to other wells of the multi-well plate 100 depending on the arrangement of the second α-thalassemia reagent mixture within the multi-well plate 100.

The amplification plots of FIG. 5A and FIG. 5B can be generated by the software program of the high-throughput PCR instrument (e.g., CFX Manager™ provided by Bio-Rad®). Each of the samples 7 through 12 can have one amplification plot associated with each sample. The plots can be the tracked fluorescence signals of the FAM fluorophore in each reaction well, vessel, or tube. As indicated in Tables 3 and 4, the FAM reporter or fluorophore can be coupled to the SEA fluorescent probe.

In one embodiment, a method of detecting an −−SEA or −−$^{SEA}$ large fragment deletion genotype within each sample can comprise the following steps: (1) monitoring the fluorescence level of the FAM reporter (of the SEA fluorescence probe) and (2) diagnosing the template or patient DNA within the sample as either (i) likely having the heterozygous −−SEA/a genotype if the fluorescence level reaches and exceeds a threshold fluorescence level as shown in FIG. 5A (i.e., if a Cq value is present) or (ii) likely not having the −−SEA/αα genotype or having the homozygous αα/αα genotype if the fluorescence level of the FAM reporter never reaches the threshold fluorescence level as shown in FIG. 5B (i.e., if a Cq value is never established).

FIG. 5A illustrates that samples 7 through 10 were detected as samples from patients likely having the −−SEA/αα large fragment deletion genotype and FIG. 5B illustrates that samples 11 and 12 were detected as samples from patients likely having the normal or wild-type αα/αα genotype. In some embodiments, such detection methods can be performed by a laboratory technician or medical professional. In other embodiments, such detection methods can be implemented as machine-executable software instructions programmed to run on a computer, a portable or handheld device such as a tablet or smartphone, a PCR instrument, or any combination thereof.

Figure 6:
FIG. 6 is an annotated photograph of a gel electrophoresis corroborating the results of detection performed using the methods and kits described herein.

FIG. 6 illustrates an annotated photograph of a gel electrophoresis showing the results of the same samples 7 through 12 described in the preceding sections diagnosed using Gap-PCR followed by gel electrophoresis. As shown in FIG. 6, the traditional method of using Gap-PCR followed by gel electrophoresis confirmed samples 7 through 10 as the heterozygous --SEA/αα genotype and samples 11 and 12 as the normal or wild-type αα/αα genotype.

Although not shown in the figures, the same method of detecting the --SEA or --$^{SEA}$ large fragment deletion genotype can also be applied to detecting the --THAI or --THAI large fragment deletion genotype. For example, one or more samples can be injected, pipetted, or otherwise introduced to wells of the multi-well plate 100 of FIG. 1 containing the third α-thalassemia reagent mixture for detecting the α-thalassemia --THAI (or --$^{THAI}$) large fragment deletion genotype. An amplification plot similar to any of the amplification plots shown in FIG. 5A can be generated by the software program of the high-throughput PCR instrument (e.g., CFX Manager™ provided by Bio-Rad®). The plot(s) can be the tracked fluorescence signal(s) of the FAM fluorophore in each reaction well, vessel, or tube. As indicated in Tables 3 and 4, the FAM reporter or fluorophore can be coupled to the THAI fluorescent probe.

In one embodiment, a method of detecting an --THAI or --THAI large fragment deletion genotype within each sample can comprise the following steps: (1) monitoring the fluorescence level of the FAM reporter (of the THAI fluorescence probe) and (2) diagnosing the template or patient DNA within the sample as either (i) likely having the heterozygous --THAI/αα genotype if the fluorescence level reaches and exceeds a threshold fluorescence level (i.e., if a Cq value is present) or (ii) likely not having the --THAI/αα genotype or having the homozygous αα/αα genotype if the fluorescence level of the FAM reporter never reaches the threshold fluorescence level (i.e., if a Cq value is never established).

Figure 7A:
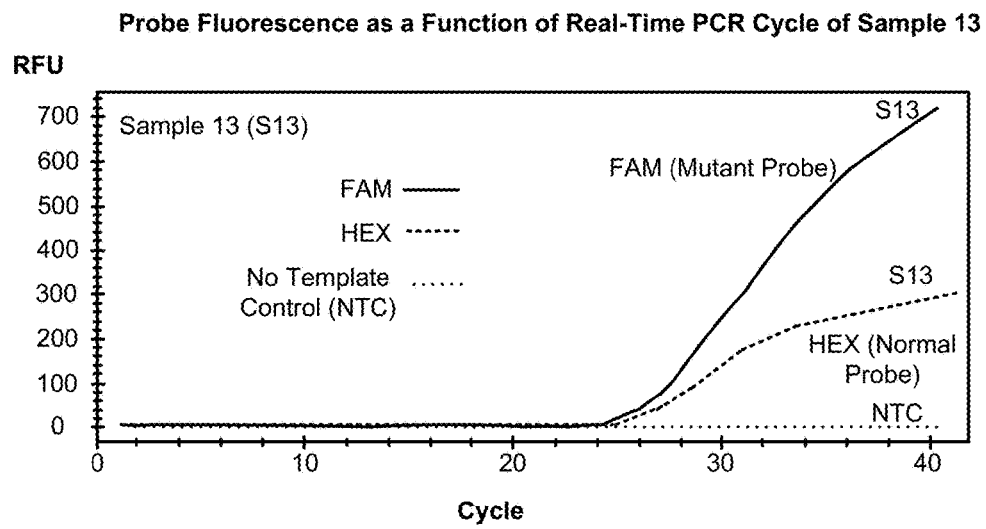
FIG. 7A illustrates amplification plots of DNA extracted or isolated from a patient sample.

FIG. 7A illustrates an amplification plot of DNA extracted or isolated from another patient sample (e.g., sample 13). For example, sample 13 can be injected, pipetted, or otherwise introduced to one of the wells in column 4 of the multi-well plate 100 of FIG. 1 containing the fourth α-thalassemia reagent mixture. Sample 13 can also be introduced to other wells of the multi-well plate 100 depending on the arrangement of the fourth α-thalassemia reagent mixture within the multi-well plate 100.

The amplification plots of FIG. 7A can be generated by the software program of the high-throughput PCR instrument (e.g., CFX Manager™ provided by Bio-Rad®). Sample 13 can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to the αCSα fluorescent normal probe and the FAM reporter or fluorophore can be coupled to the αCSα fluorescent mutant probe. Although two probe amplification plots for the sample are displayed in the example graph of FIG. 7A, it should be understood by one of ordinary skill in the art that the software program can display singular plots or any combination of plots to a user of the high-throughput PCR instrument.

In one embodiment, a method of detecting an αCSα mutation genotype within the sample can comprise the following steps: (1) calculating an RFU ratio involving the RFU of the FAM reporter at cycle 40, the RFU of the HEX reporter at cycle 40, and the RFU of the no template control (NTC), as shown in Equation 3 below (hereinafter known as a normalized RFU or NRFU) and (2) diagnosing the template or patient DNA within the sample as (i) likely having the heterozygous αCSα/αα genotype or (ii) likely not having the heterozygous αCSα/αα genotype or having the homozygous normal or wildtype αα/αα genotype if the conditions set forth in Conditions 7 and 8 below are satisfied.

$$NRFU_{cycle\,40} = FAM(RFU_{cycle\,40})/(FAM(RFU_{cycle\,40}) + HEX(RFU_{cycle\,40}) + NTC(RFU_{cycle\,40}))$$ Equation 3

Condition 7: If $NRFU \geq 0.25$, then genotype is αCSα/αα

Condition 8: If $NRFU < 0.25$, then genotype is not αCSα/αα or normal αα/αα

Figure 7B:
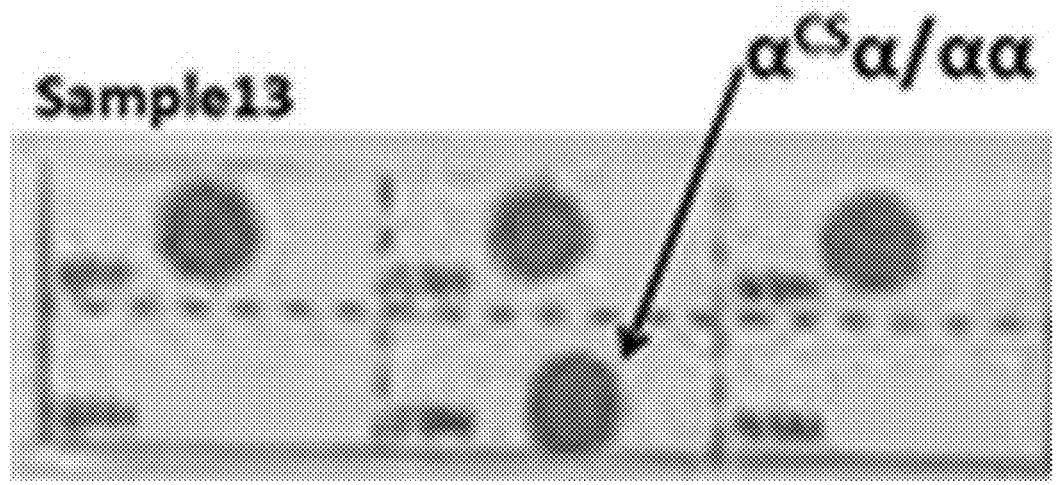
FIG. 7B is an annotated photograph of the results of a PCR-reverse dot blot hybridization corroborating the results of detection performed using the methods and kits described herein.

FIG. 7B illustrates an annotated photograph of a PCR-reverse dot blot showing the results of the same sample 13 described in the preceding sections diagnosed using PCR-reverse dot blot hybridization. As shown in FIG. 7B, the traditional method of using PCR-reverse dot blot hybridization confirmed sample 13 as the heterozygous αCSα/αα genotype.

Figure 8A:
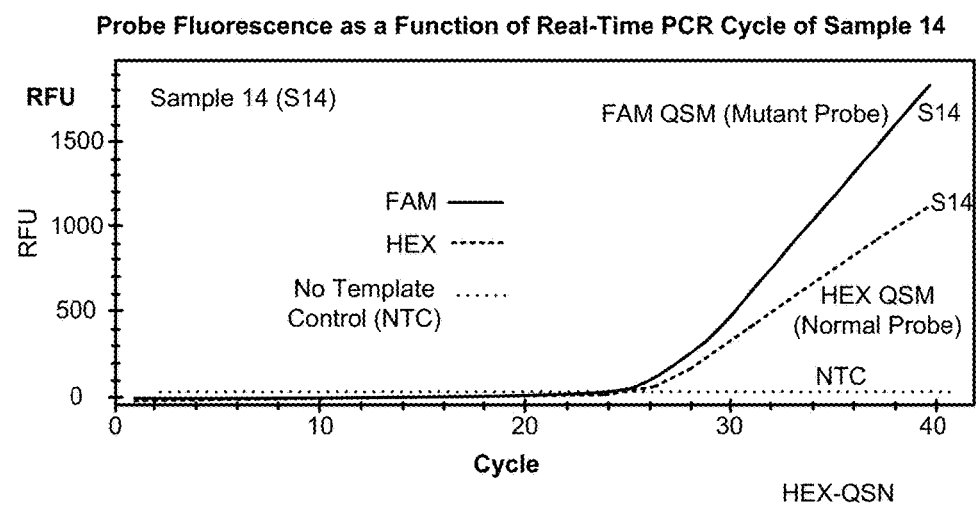
FIG. 8A illustrates amplification plots of DNA extracted or isolated from a patient sample.

FIG. 8A illustrates an amplification plot of DNA extracted or isolated from another patient sample (e.g., sample 14). For example, sample 14 can be injected, pipetted, or otherwise introduced to one of the wells in column 5 of the multi-well plate 100 of FIG. 1 containing the fifth α-thalassemia reagent mixture for detecting an α-thalassemia αQSα mutation genotype. Sample 14 can also be introduced to other wells of the multi-well plate 100 depending on the arrangement of the fifth α-thalassemia reagent mixture within the multi-well plate 100.

The amplification plots of FIG. 8A can be generated by the software program of the high-throughput PCR instrument (e.g., CFX Manager™ provided by Bio-Rad®). Sample 14 can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to the αQSα fluorescent normal probe and the FAM reporter or fluorophore can be coupled to the αQSα fluorescent mutant probe. Although two probe amplification plots for the sample are displayed in the example graph of FIG. 8A, it should be understood by one of ordinary skill in the art that the software program can display singular plots or any combination of plots to a user of the high-throughput PCR instrument.

In one embodiment, a method of detecting an αQSα mutation genotype within the sample can comprise the following steps: (1) calculating an NRFU or RFU ratio involving the RFU of the FAM reporter at cycle 40, the RFU of the HEX reporter at cycle 40, and the RFU of the NTC, as shown in Equation 3 in the preceding section and (2)

diagnosing the template or patient DNA within the sample as (i) likely having the heterozygous αQSα/αα genotype or (ii) likely not having the heterozygous αQSα/αα genotype or having the homozygous normal or wildtype αα/αα genotype if the conditions set forth in Conditions 9 and 10 below are satisfied.

Condition 9: If NRFU≥0.25, then genotype is αQSα/αα
Condition 10: If NRFU<0.25, then genotype is not αQSα/αα or normal αα/αα

Figure 8B:
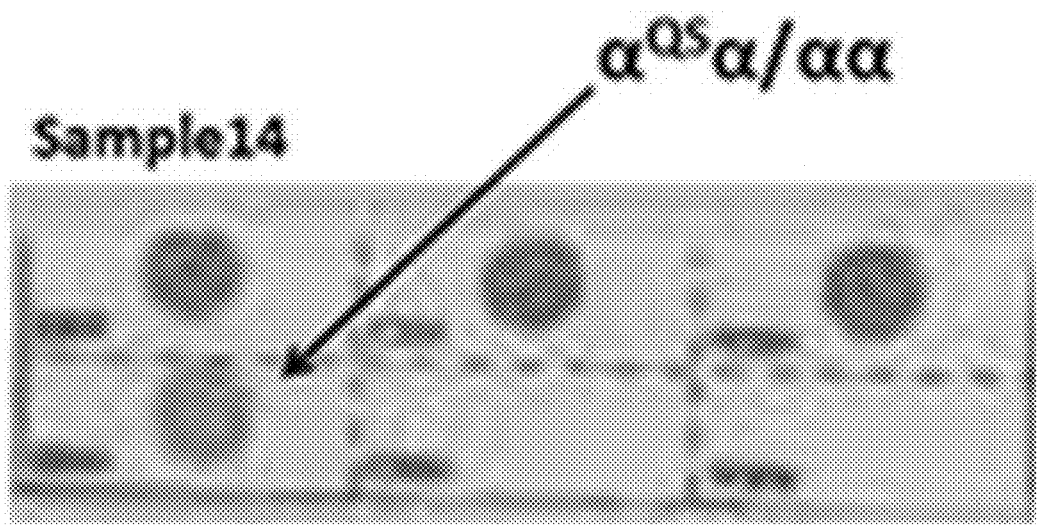
FIG. 8B is an annotated photograph of the results of a PCR-reverse dot blot hybridization corroborating the results of detection performed using the methods and kits described herein.

FIG. 8B illustrates an annotated photograph of a PCR-reverse dot blot showing the results of the same sample 14 described in the preceding sections diagnosed using PCR-reverse dot blot hybridization. As shown in FIG. 8B, the traditional method of using PCR-reverse dot blot hybridization confirmed sample 14 as the heterozygous αQSα/αα genotype.

Figure 9A:
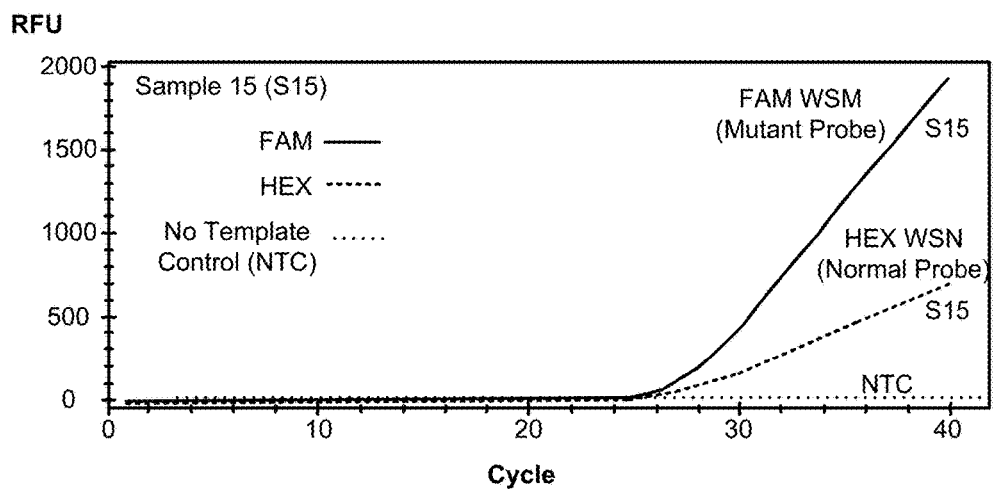
FIG. 9A illustrates amplification plots of DNA extracted or isolated from a patient sample.

FIG. 9A illustrates an amplification plot of DNA extracted or isolated from another patient sample (e.g., sample 15). For example, sample 14 can be injected, pipetted, or otherwise introduced to one of the wells in column 6 of the multi-well plate 100 of FIG. 1 containing the sixth α-thalassemia reagent mixture for detecting an α-thalassemia αWSα mutation genotype. Sample 15 can also be introduced to other wells of the multi-well plate 100 depending on the arrangement of the fifth α-thalassemia reagent mixture within the multi-well plate 100.

The amplification plots of FIG. 9A can be generated by the software program of the high-throughput PCR instrument (e.g., CFX Manager™ provided by Bio-Rad®). Sample 15 can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to the αWSα fluorescent normal probe and the FAM reporter or fluorophore can be coupled to the αWSα fluorescent mutant probe. Although two probe amplification plots for the sample are displayed in the example graph of FIG. 9A, it should be understood by one of ordinary skill in the art that the software program can display singular plots or any combination of plots to a user of the high-throughput PCR instrument.

In one embodiment, a method of detecting an αWSα mutation genotype within the sample can comprise the following steps: (1) calculating an NRFU or RFU ratio involving the RFU of the FAM reporter at cycle 40, the RFU of the HEX reporter at cycle 40, and the RFU of the NTC, as shown in Equation 3 in the preceding section and (2) diagnosing the template or patient DNA within the sample as (i) likely having the heterozygous αWSα/αα genotype or (ii) likely not having the heterozygous αWSα/αα genotype or having the homozygous normal or wildtype αα/αα genotype if the conditions set forth in Conditions 11 and 12 below are satisfied.

Condition 11: If NRFU≥0.25, then genotype is αWSα/αα
Condition 12: If NRFU<0.25, then genotype is not αWSα/αα or normal αα/αα

Figure 9B:
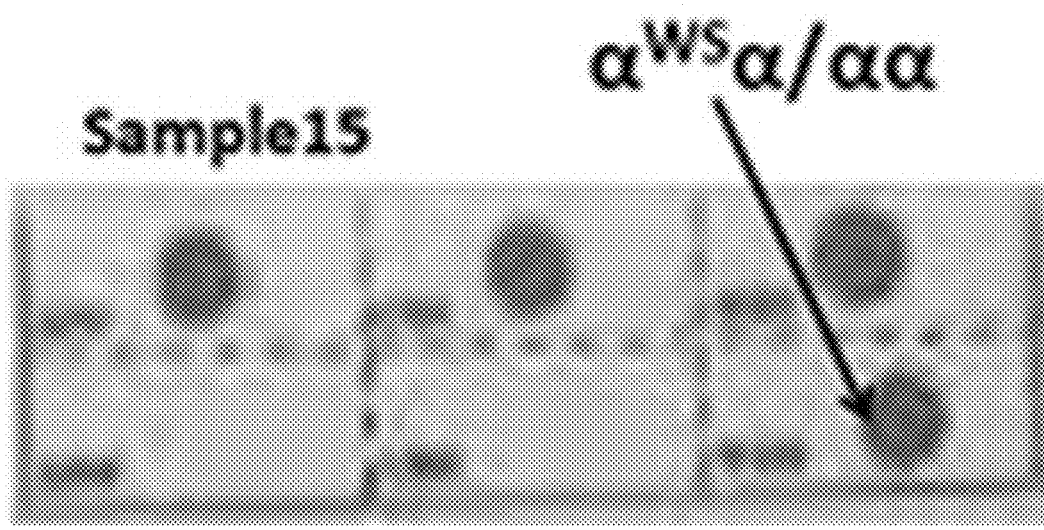
FIG. 9B is an annotated photograph of the results of a PCR-reverse dot blot hybridization corroborating the results of detection performed using the methods and kits described herein.

FIG. 9B illustrates an annotated photograph of a PCR-reverse dot blot showing the results of the same sample 15 described in the preceding sections diagnosed using PCR-reverse dot blot hybridization. As shown in FIG. 9B, the traditional method of using PCR-reverse dot blot hybridization confirmed sample 15 as the heterozygous αWSα/αα genotype.

Figure 10A:
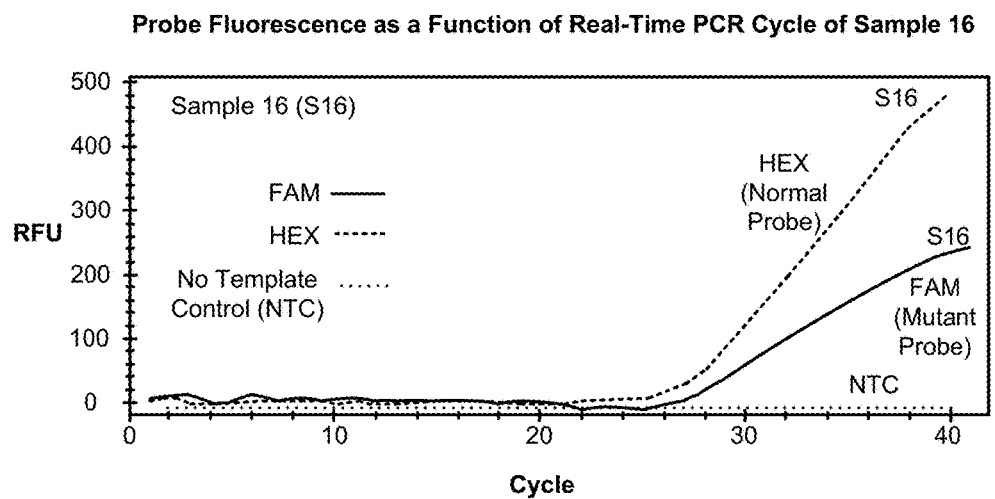
FIG. 10A illustrates amplification plots of DNA extracted or isolated from a patient sample.

FIG. 10A illustrates an amplification plot of DNA extracted or isolated from another patient sample (e.g., sample 16). For example, sample 16 can be injected, pipetted, or otherwise introduced to any of the wells in columns 4 through 6 of the multi-well plate 100 of FIG. 1 containing the fourth α-thalassemia reagent mixture, the fifth α-thalassemia reagent mixture, or the sixth α-thalassemia reagent mixture, respectively. Sample 16 can also be introduced to other wells of the multi-well plate 100 depending on the arrangement of the various α-thalassemia reagent mixtures within the multi-well plate 100.

The amplification plots of FIG. 10A can be generated by the software program of the high-throughput PCR instrument (e.g., CFX Manager™ provided by Bio-Rad®). Sample 16 can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to an α-thalassemia fluorescent normal probe (such as an αCSα, αQSα, or αWSα fluorescent normal probe) and the FAM reporter or fluorophore can be coupled to an α-thalassemia fluorescent mutation probe (such as an αCSα, αQSα, or αWSα fluorescent mutant probe). Although two probe amplification plots for the sample are displayed in the example graph of FIG. 10A, it should be understood by one of ordinary skill in the art that the software program can display singular plots or any combination of plots to a user of the high-throughput PCR instrument.

FIG. 10A illustrates that when DNA extracted or isolated from a patient sample does not have any of the α-thalassemia mutation genotypes discussed in the preceding sections (e.g., the αCSα, αQSα, or αWSα genotypes), the RFU of the HEX amplification plot at cycle 40 can be significantly greater than the FAM amplification plot at cycle 40. In addition, the NRFU or RFU ratio calculated using Equation 3 in the preceding section (involving the RFU of the FAM reporter at cycle 40, the RFU of the HEX reporter at cycle 40, and the RFU of the NTC) is less than 0.25. The presence of the FAM amplification plot is a result of nonspecific binding of mutant probes to template DNA not having any α-thalassemia mutation genotypes.

Figure 10B:
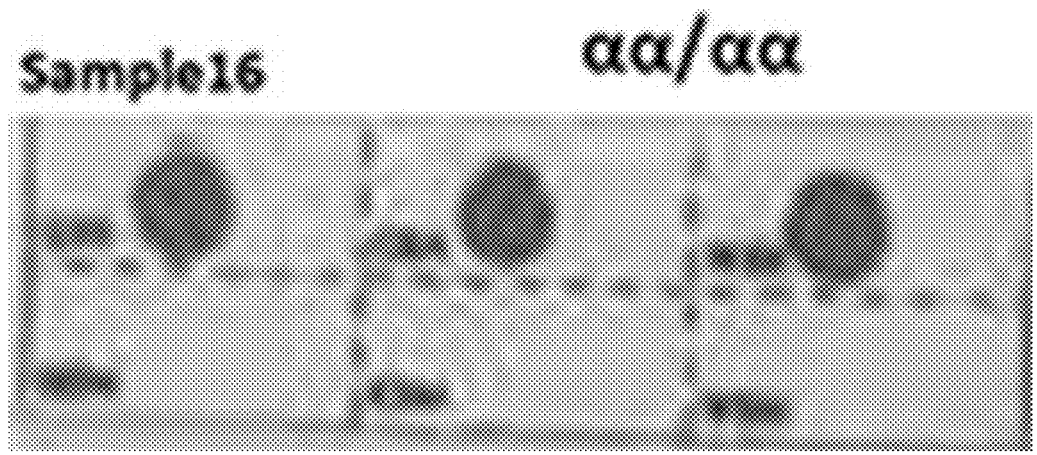
FIG. 10B is an annotated photograph of the results of a PCR-reverse dot blot hybridization corroborating the results of detection performed using the methods and kits described herein.

FIG. 10B illustrates an annotated photograph of a PCR-reverse dot blot showing the results of the same sample 16 described in the preceding sections diagnosed using PCR-reverse dot blot hybridization. As shown in FIG. 10B, the traditional method of using PCR-reverse dot blot hybridization confirmed sample 16 as the homozygous normal or wildtype αα/αα genotype.

Figure 11A:
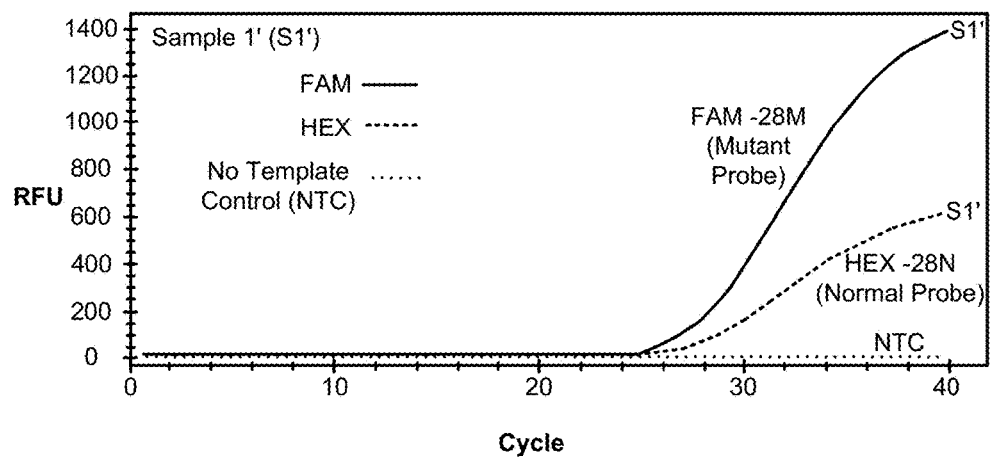
FIG. 11A illustrates amplification plots of DNA extracted or isolated from a patient sample.

FIG. 11A illustrates an amplification plot of DNA extracted or isolated from another patient sample (e.g., sample 1' or S1'). For example, sample 1' can be injected, pipetted, or otherwise introduced to one of the wells in column 7 of the multi-well plate 100 of FIG. 1 containing the second β-thalassemia reagent mixture for detecting a β-thalassemia −28M mutation genotype. Sample 1' can also be introduced to other wells of the multi-well plate 100 depending on the arrangement of the second β-thalassemia reagent mixture within the multi-well plate 100.

The amplification plots of FIG. 11A can be generated by the software program of the high-throughput PCR instrument (e.g., CFX Manager™ provided by Bio-Rad®). Sample 1' can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to the −28M fluorescent normal probe and the FAM reporter or fluorophore can be coupled to the −28M fluorescent mutant probe. Although two probe amplification plots for the sample are displayed in the example graph of FIG. 11A, it should be understood by one of ordinary skill in the art that the software program can display singular plots or any combination of plots to a user of the high-throughput PCR instrument.

In one embodiment, a method of detecting the −28M mutation genotype within the sample can comprise the following steps: (1) calculating an NRFU or RFU ratio involving the RFU of the FAM reporter at cycle 40, the RFU of the HEX reporter at cycle 40, and the RFU of the NTC, as shown in Equation 3 in the preceding section and (2) diagnosing the template or patient DNA within the sample as (i) likely having the heterozygous −28M/$\beta^N$ genotype or (ii) likely not having the heterozygous −28M/$\beta^N$ genotype or having the homozygous normal or wildtype $\beta^N/\beta^N$ genotype if the conditions set forth in Conditions 13 and 14 below are satisfied.

Condition 13: If NRFU≥0.25, then genotype is −28M/$\beta^N$ genotype

Figure 11B:
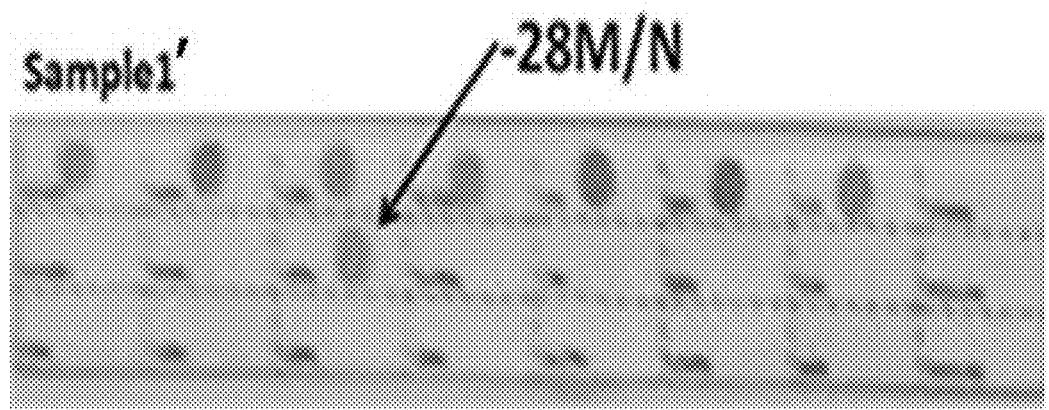
FIG. 11B is an annotated photograph of the results of a PCR-reverse dot blot hybridization corroborating the results of detection performed using the methods and kits described herein.

Condition 14: If NRFU<0.25, then genotype is not −28M/$\beta^N$ genotype or normal $\beta^N/\beta^N$ FIG. 11B illustrates an annotated photograph of a PCR-reverse dot blot showing the results of the same sample 1' described in the preceding sections diagnosed using PCR-reverse dot blot hybridization. As shown in FIG. 11B, the traditional method of using PCR-reverse dot blot hybridization confirmed sample 1' as the heterozygous −28M/$\beta^N$ mutation genotype.

Figure 12A:
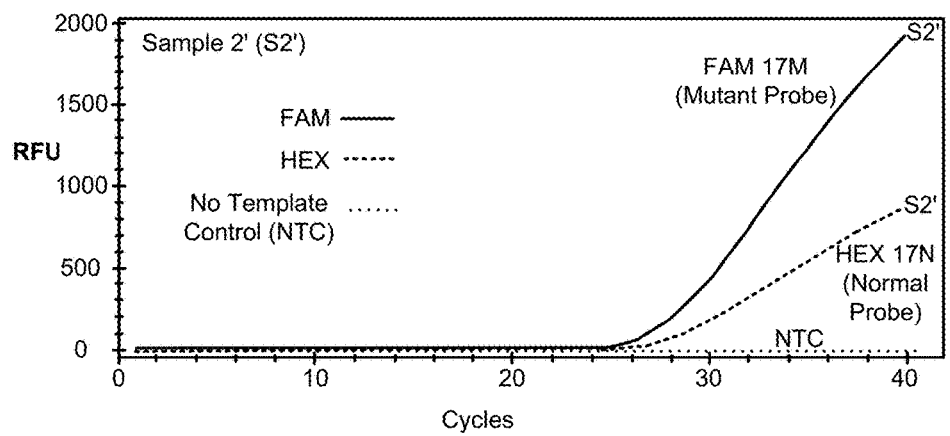
FIG. 12A illustrates amplification plots of DNA extracted or isolated from a patient sample.

FIG. 12A illustrates an amplification plot of DNA extracted or isolated from another patient sample (e.g., sample 2' or S2'). For example, sample 2' can be injected, pipetted, or otherwise introduced to one of the wells in column 8 of the multi-well plate 100 of FIG. 1 containing the fourth β-thalassemia reagent mixture for detecting a β-thalassemia 17M point mutation genotype. Sample 2' can also be introduced to other wells of the multi-well plate 100 depending on the arrangement of the fourth β-thalassemia reagent mixture within the multi-well plate 100.

The amplification plots of FIG. 12A can be generated by the software program of the high-throughput PCR instrument (e.g., CFX Manager™ provided by Bio-Rad®). Sample 2' can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to the 17M fluorescent normal probe and the FAM reporter or fluorophore can be coupled to the 17M fluorescent mutant probe. Although two probe amplification plots for the sample are displayed in the example graph of FIG. 12A, it should be understood by one of ordinary skill in the art that the software program can display singular plots or any combination of plots to a user of the high-throughput PCR instrument.

In one embodiment, a method of detecting the 17M mutation genotype within the sample can comprise the following steps: (1) calculating an NRFU or RFU ratio involving the RFU of the FAM reporter at cycle 40, the RFU of the HEX reporter at cycle 40, and the RFU of the NTC, as shown in Equation 3 in the preceding section and (2) diagnosing the template or patient DNA within the sample as (i) likely having the heterozygous 17M/$\beta^N$ genotype or (ii) likely not having the heterozygous 17M/$\beta^N$ genotype or having the homozygous normal or wildtype $\beta^N/\beta^N$ genotype if the conditions set forth in Conditions 15 and 16 below are satisfied.

Condition 15: If NRFU≥0.25, then genotype is 17M/$\beta^N$ genotype

Figure 12B:
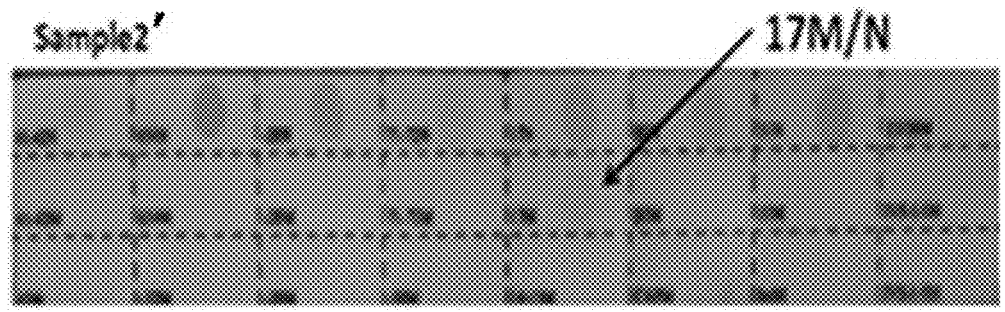
FIG. 12B is an annotated photograph of the results of a PCR-reverse dot blot hybridization corroborating the results of detection performed using the methods and kits described herein.

Condition 16: If NRFU<0.25, then genotype is not 17M/$\beta^N$ genotype or normal $\beta^N/\beta^N$ FIG. 12B illustrates an annotated photograph of a PCR-reverse dot blot showing the results of the same sample 2' described in the preceding sections diagnosed using PCR-reverse dot blot hybridization. As shown in FIG. 12B, the traditional method of using PCR-reverse dot blot hybridization confirmed sample 2' as the heterozygous 17M/$\beta^N$ mutation genotype.

Figure 13A:
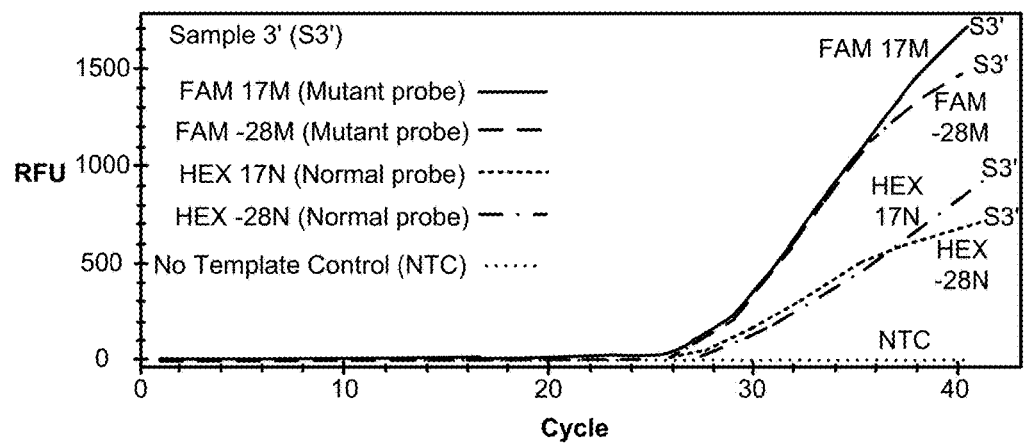
FIG. 13A illustrates amplification plots of DNA extracted or isolated from a patient sample.

FIG. 13A illustrates amplification plots of DNA extracted or isolated from another patient sample (e.g., sample 3' or S3'). For example, sample 3' can be injected, pipetted, or otherwise introduced to wells in column 7 (containing the −28M β-thalassemia reagent mixture) and column 8 (containing the 17M β-thalassemia reagent mixture) of the multi-well plate 100 of FIG. 1. Sample 3' can also be introduced to other wells of the multi-well plate 100 depending on alternative arrangements of the β-thalassemia reagent mixtures within the multi-well plate 100.

The amplification plots of FIG. 13A can be generated by the software program of the high-throughput PCR instrument (e.g., CFX Manager™ provided by Bio-Rad®). Sample 3' can have multiple probe plots associated with the sample. The multiple amplification plots can include the tracked fluorescence signals of the HEX and FAM fluorophores in two of the reaction wells, vessels, or tubes. As shown in FIG. 13A and using the methods described in the preceding sections for detecting the 17M and −28M mutation genotypes, sample 3' can be determined as comprising patient DNA having both the 17M mutation genotype and the −28M mutation genotype.

Figure 13B:
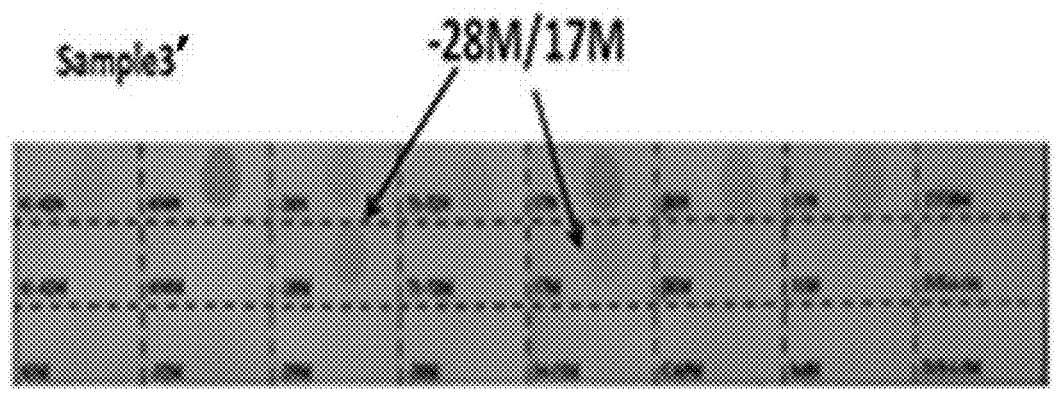
FIG. 13B is an annotated photograph of the results of a PCR-reverse dot blot hybridization corroborating the results of detection performed using the methods and kits described herein.

FIG. 13B illustrates an annotated photograph of a PCR-reverse dot blot showing the results of the same sample 3' described in the preceding sections diagnosed using PCR-reverse dot blot hybridization. As shown in FIG. 13B, the traditional method of using PCR-reverse dot blot hybridization confirmed sample 3' as having the 17M mutation genotype and the −28M mutation genotype.

Figure 14A:
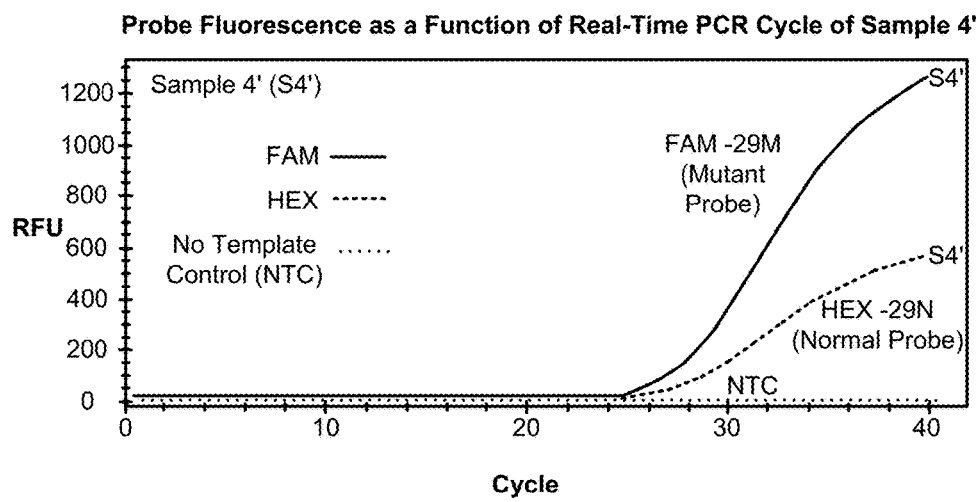
FIG. 14A illustrates amplification plots of DNA extracted or isolated from a patient sample.

FIG. 14A illustrates an amplification plot of DNA extracted or isolated from another patient sample (e.g., sample 4' or S4'). For example, sample 4' can be injected, pipetted, or otherwise introduced to one of the wells in column 9 of the multi-well plate 100 of FIG. 1 containing the third β-thalassemia reagent mixture for detecting a β-thalassemia −29M mutation genotype. Sample 4' can also be introduced to other wells of the multi-well plate 100 depending on the arrangement of the third β-thalassemia reagent mixture within the multi-well plate 100.

The amplification plots of FIG. 14A can be generated by the software program of the high-throughput PCR instrument (e.g., CFX Manager™ provided by Bio-Rad®). Sample 4' can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to the −29M fluorescent normal probe and the FAM reporter or fluorophore can be coupled to the −29M fluorescent mutant probe. Although two probe amplification plots for the sample are displayed in the example graph of FIG. 14A, it should be understood by one of ordinary skill in the art that the software program can display singular plots or any combination of plots to a user of the high-throughput PCR instrument.

In one embodiment, a method of detecting the −29M mutation genotype within the sample can comprise the following steps: (1) calculating an NRFU or RFU ratio involving the RFU of the FAM reporter at cycle 40, the RFU of the HEX reporter at cycle 40, and the RFU of the NTC, as shown in Equation 3 in the preceding section and (2) diagnosing the template or patient DNA within the sample as (i) likely having the heterozygous $-29M/\beta^N$ genotype or (ii) likely not having the heterozygous $-29M/\beta^N$ genotype or having the homozygous normal or wildtype $\beta^N/\beta^N$ genotype if the conditions set forth in Conditions 17 and 18 below are satisfied.

Condition 17: If NRFU≥0.25, then genotype is $-29M/\beta^N$ genotype

Figure 14B:
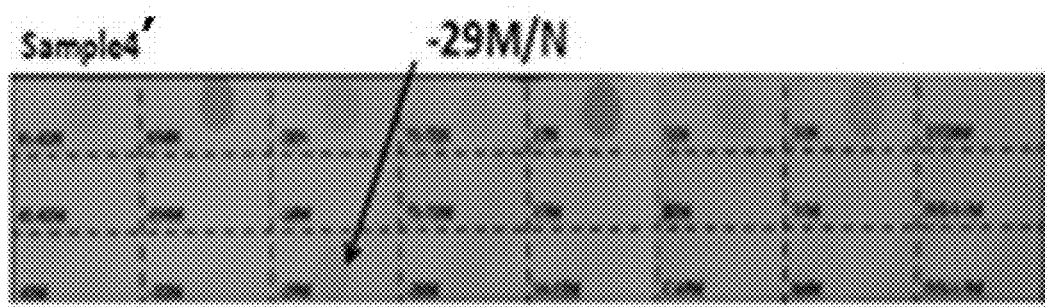
FIG. 14B is an annotated photograph of the results of a PCR-reverse dot blot hybridization corroborating the results of detection performed using the methods and kits described herein.

Condition 18: If NRFU<0.25, then genotype is not $-29M/\beta^N$ genotype or normal $\beta^N/\beta^N$ FIG. 14B illustrates an annotated photograph of a PCR-reverse dot blot showing the results of the same sample 4' described in the preceding sections diagnosed using PCR-reverse dot blot hybridization. As shown in FIG. 14B, the traditional method of using PCR-reverse dot blot hybridization confirmed sample 4' as the heterozygous $-29M/\beta^N$ mutation genotype.

Figure 15A:
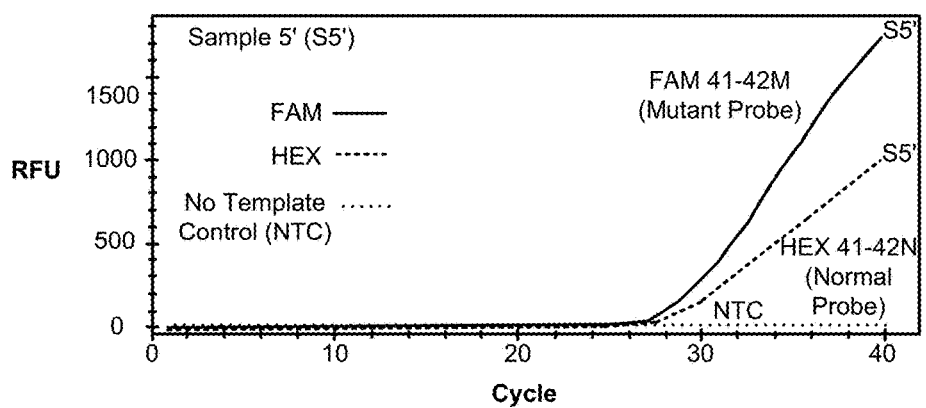
FIG. 15A illustrates amplification plots of DNA extracted or isolated from a patient sample.

FIG. 15A illustrates an amplification plot of DNA extracted or isolated from another patient sample (e.g., sample 5' or S5'). For example, sample 5' can be injected, pipetted, or otherwise introduced to one of the wells in column 10 of the multi-well plate 100 of FIG. 1 containing the first β-thalassemia reagent mixture for detecting a β-thalassemia 41-42M deletion genotype. Sample 5' can also be introduced to other wells of the multi-well plate 100 depending on the arrangement of the fourth β-thalassemia reagent mixture within the multi-well plate 100.

The amplification plots of FIG. 15A can be generated by the software program of the high-throughput PCR instrument (e.g., CFX Manager™ provided by Bio-Rad®). Sample 5' can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to the 41-42M fluorescent normal probe and the FAM reporter or fluorophore can be coupled to the 41-42M fluorescent mutant probe. Although two probe amplification plots for the sample are displayed in the example graph of FIG. 15A, it should be understood by one of ordinary skill in the art that the software program can display singular plots or any combination of plots to a user of the high-throughput PCR instrument.

In one embodiment, a method of detecting the 41-42M mutation genotype within the sample can comprise the following steps: (1) calculating an NRFU or RFU ratio involving the RFU of the FAM reporter at cycle 40, the RFU of the HEX reporter at cycle 40, and the RFU of the NTC, as shown in Equation 3 in the preceding section and (2) diagnosing the template or patient DNA within the sample as (i) likely having the heterozygous 41-42M/$\beta^N$ genotype or (ii) likely not having the heterozygous 41-42M/$\beta^N$ genotype or having the homozygous normal or wildtype $\beta^N/\beta^N$ genotype if the conditions set forth in Conditions 19 and 20 below are satisfied.

Condition 19: If NRFU≥0.25, then genotype is 41-42M/$\beta^N$ genotype

Figure 15B:
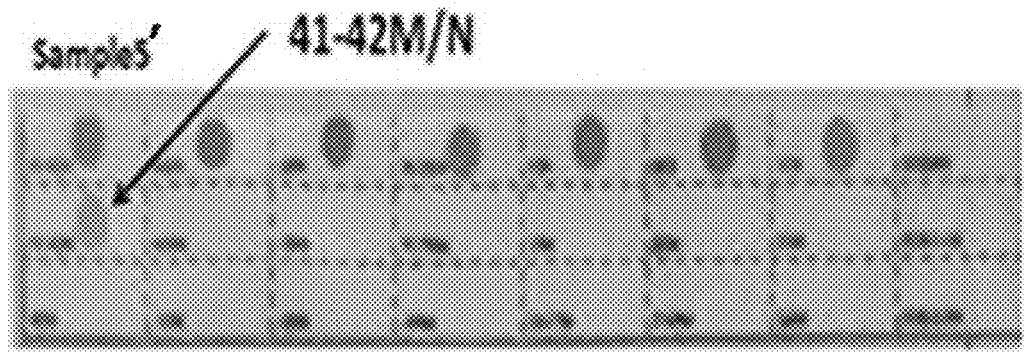
FIG. 15B is an annotated photograph of the results of a PCR-reverse dot blot hybridization corroborating the results of detection performed using the methods and kits described herein.

Condition 20: If NRFU<0.25, then genotype is not 41-42M/$\beta^N$ genotype or normal $\beta^N/\beta^N$ FIG. 15B illustrates an annotated photograph of a PCR-reverse dot blot showing the results of the same sample 5' described in the preceding sections diagnosed using PCR-reverse dot blot hybridization. As shown in FIG. 15B, the traditional method of using PCR-reverse dot blot hybridization confirmed sample 5' as the heterozygous 41-42M/$\beta^N$ mutation genotype.

Although not shown in the figures, the same method of detecting the 41-42M mutation genotype, the −28M mutation genotype, the 17M mutation genotype, and the −29M mutation genotype can also be applied to detecting the following β-thalassemia mutation genotypes: the 31M mutation, the CAPM mutation, the −30M mutation, the −32M mutation, the 43M mutation, the 90M mutation, the 654 M mutation, the IntM mutation, the IVS-I-1M mutation, the IVS-I-5M mutation, the IVS-II-5M mutation, the βEM mutation, the CD37M mutation, the 14-15M mutation, the 27/28M mutation, and the 71-72M mutation.

The method comprises the step of calculating an NRFU or RFU ratio, as shown in Equation 3, involving the cycle 40 RFU of the FAM reporter coupled to a mutant probe targeting one of the aforementioned β-thalassemia genotypes, the cycle 40 RFU of the HEX reporter coupled to a normal probe targeting a corresponding normal or wild-type allele, and the cycle 40 RFU of the NTC.

In some embodiments, the method can comprise diagnosing the template or patient DNA within the sample as (i) likely having the aforementioned β-thalassemia genotypes or (ii) likely not having the aforementioned β-thalassemia genotypes or having the homozygous normal or wildtype $\beta^N/\beta^N$ genotype if the conditions set forth in Conditions 21 and 22 below are satisfied.

Condition 21: If NRFU≥0.25, then genotype is one of the following β-thalassemia genotypes: the 31M mutation genotype, the CAPM mutation genotype, the −30M mutation genotype, the −32M mutation genotype, the 43M mutation genotype, the 90M mutation genotype, the IntM mutation genotype, the IVS-I-1M mutation genotype, the IVS-I-5M mutation genotype, the IVS-II-5M mutation genotype, the βEM mutation genotype, the CD37M mutation genotype, the 14-15M mutation genotype, the 27/28M mutation genotype, or the 71-72M mutation genotype Condition 22: If NRFU<0.25, then genotype is not one of the aforementioned β-thalassemia mutation genotypes or is a normal $\beta^N/\beta^N$ genotype In these and other embodiments, the method can further comprise diagnosing the template or patient DNA within the sample as (i) likely having the heterozygous 654M/$\beta^N$ genotype or (ii) likely not having the heterozygous 654M/$\beta^N$ genotype or having the homozygous normal or wildtype $\beta^N/\beta^N$ genotype if the conditions set forth in Conditions 23 and 24 below are satisfied.

Condition 23: If NRFU≥0.05, then genotype is 654 M/$\beta^N$ genotype

Figure 16A:
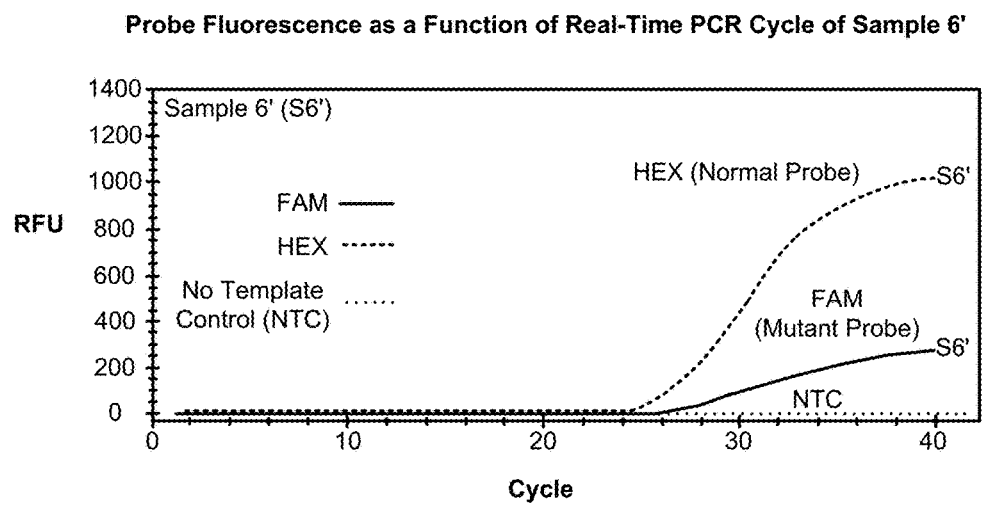
FIG. 16A illustrates amplification plots of DNA extracted or isolated from a patient sample.

Condition 24: If NRFU<0.05, then genotype is not 654 M/$\beta^N$ genotype or normal $\beta^N/\beta^N$ FIG. 16A illustrates an amplification plot of DNA extracted or isolated from another patient sample (e.g., sample 6'). For example, sample 6' can be injected, pipetted, or otherwise introduced to any of the wells in columns 7 through 10 of the multi-well plate 100 of FIG. 1 containing any of the aforementioned β-thalassemia reagent mixtures. Sample 6' can also be introduced to other wells of the multi-well plate 100 depending on the arrangement of the various β-thalassemia reagent mixtures within the multi-well plate 100.

The amplification plots of FIG. 16A can be generated by the software program of the high-throughput PCR instrument (e.g., CFX Manager™ provided by Bio-Rad®). Sample 6' can have two probe plots associated with the sample. The two plots can include the tracked fluorescence signals of the HEX and FAM fluorophores in the reaction well, vessel, or tube. As indicated in Tables 3 and 4, the HEX reporter or fluorophore can be coupled to an 3-thalassemia fluorescent normal probe and the FAM reporter or fluorophore can be coupled to a β-thalassemia fluorescent mutation probe. Although two probe amplification plots for the sample are displayed in the example graph of FIG. 16A, it should be understood by one of ordinary skill in the art that the software program can display singular plots or any combination of plots to a user of the high-throughput PCR instrument.

FIG. 16A illustrates that when DNA extracted or isolated from a patient sample does not have any of the β-thalassemia mutation genotypes discussed in the preceding sections, the RFU of the HEX normal probe plot at cycle 40 can be significantly greater than the FAM mutant probe plot at cycle 40. In addition, the NRFU or RFU ratio calculated using Equation 3 in the preceding section (involving the RFU of the FAM reporter at cycle 40, the RFU of the HEX reporter at cycle 40, and the RFU of the NTC) is less than 0.25. The presence of the FAM amplification plot is a result of nonspecific binding of mutant probes to template DNA not having any t-thalassemia mutation genotypes.

Figure 16B:
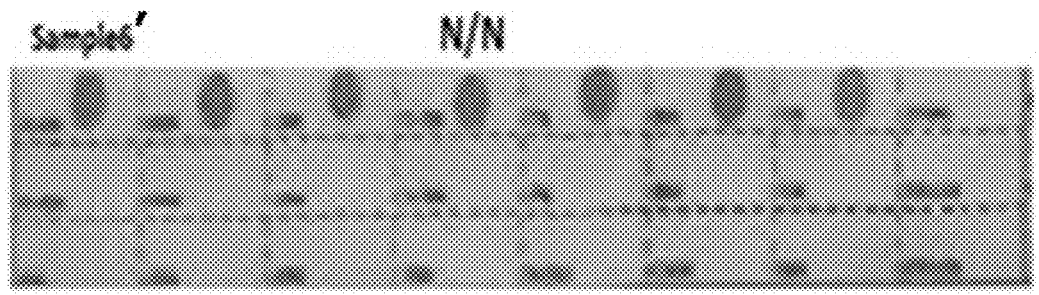
FIG. 16B is an annotated photograph of the results of a PCR-reverse dot blot hybridization corroborating the results of detection performed using the methods and kits described herein.

FIG. 16B illustrates an annotated photograph of a PCR-reverse dot blot showing the results of the same sample 6' described in the preceding sections diagnosed using PCR-reverse dot blot hybridization. As shown in FIG. 16B, the traditional method of using PCR-reverse dot blot hybridization confirmed sample 6' as the homozygous normal or wildtype $\beta^N/\beta^N$ genotype.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

What is claimed is:

1. A diagnostic kit for detecting multiple forms of thalassemia using real-time polymerase chain reaction (PCR), comprising:
 a reagent mixture for detecting an α-thalassemia –α3.7 deletion genotype or an α-thalassemia –α4.2 deletion genotype, comprising:
  a first forward oligonucleotide primer consisting of SEQ ID NO 1;
  a second forward oligonucleotide primer consisting of SEQ ID NO 3;
  a first reverse oligonucleotide primer consisting of SEQ ID NO 2;
  a second reverse oligonucleotide primer consisting of SEQ ID NO 4;
  a first fluorescent probe comprising an oligonucleotide consisting of SEQ ID NO 5 and a fluorescent label;
  a second fluorescent probe comprising an oligonucleotide consisting of SEQ ID NO 6 and a fluorescent label;
  a forward reference oligonucleotide primer for an internal reference gene consisting of SEQ ID NO 7;
  a reverse reference oligonucleotide primer for the internal reference gene consisting of SEQ ID NO 8; and
  a reference fluorescent probe for the internal reference gene comprising an oligonucleotide consisting of SEQ ID NO 9 and a fluorescent label.

2. The diagnostic kit of claim 1, wherein the reagent mixture is an aqueous mixture contained in a single reaction vessel of a multi-vessel container.

3. The diagnostic kit of claim 1, wherein the reagent mixture is pre-spotted in lyophilized form in a single well of a multi-well PCR plate.

4. The diagnostic kit of claim 1, wherein the reagent mixture further comprises tris(hydroxymethyl)aminomethane (Tris) buffer, deoxynucleotide triphosphates (dNTPs), magnesium chloride (MgCl$_2$), and *Thermus aquaticus* (Taq) polymerase.

5. The diagnostic kit of claim 1, wherein the first fluorescent probe comprises a 6-carboxy-fluorescein (FAM) fluorophore.

6. The diagnostic kit of claim 5, wherein the first fluorescent probe comprises a dye having an absorption spectra between about 480 nm and 580 nm.

7. The diagnostic kit of claim 1, wherein the second fluorescent probe comprises a hexachloro-6-carboxy-fluorescein (HEX) fluorophore.

8. The diagnostic kit of claim 7, wherein the second fluorescent probe comprises a dye having an absorption spectra between about 560 nm and about 670 nm.

9. The diagnostic kit of claim 1, wherein the reference fluorescent probe comprises a 6-carboxy-X-rhodamine (ROX) fluorophore.

10. The diagnostic kit of claim 1, further comprising:
 another reagent mixture for detecting an α-thalassemia ––SEA deletion genotype, comprising:
  an SEA forward oligonucleotide primer consisting of SEQ ID NO 10;
  an SEA reverse oligonucleotide primer consisting of SEQ ID NO 11; and
  an SEA fluorescent probe comprising an oligonucleotide consisting of SEQ ID NO 12 and a fluorescent label.

11. The diagnostic kit of claim 1, further comprising:
 another reagent mixture for detecting an α-thalassemia ––THAI deletion genotype, comprising:
  a THAI forward oligonucleotide primer consisting of SEQ ID NO 100;
  a THAI reverse oligonucleotide primer consisting of SEQ ID NO 101; and
  a THAI fluorescent probe comprising an oligonucleotide consisting of SEQ ID NO 108 and a fluorescent label.

12. The diagnostic kit of claim 1, further comprising:
 another reagent mixture for detecting an α-thalassemia αCSα mutation genotype, comprising:
  an αCSα forward oligonucleotide primer consisting of SEQ ID NO 13;
  an αCSα reverse oligonucleotide primer consisting of SEQ ID NO 14;
  an αCSα fluorescent normal probe comprising an oligonucleotide consisting of SEQ ID NO 19 and a fluorescent label; and an αCSα fluorescent mutant probe comprising an oligonucleotide consisting of SEQ ID NO 20 and a fluorescent label.

13. The diagnostic kit of claim 1, further comprising:
another reagent mixture for detecting an α-thalassemia αQSα mutation genotype, comprising:
an αQSα forward oligonucleotide primer consisting of SEQ ID NO 15;
an αQSα reverse oligonucleotide primer consisting of SEQ ID NO 16;
an αQSα fluorescent normal probe comprising an oligonucleotide consisting of SEQ ID NO 21 and a fluorescent label; and
an αQSα fluorescent mutant probe comprising an oligonucleotide consisting of SEQ ID NO 22 and a fluorescent label.

14. The diagnostic kit of claim 1, further comprising:
another reagent mixture for detecting an α-thalassemia αWSα mutation genotype, comprising:
an αWSα forward oligonucleotide primer consisting of SEQ ID NO 17;
an αWSα reverse oligonucleotide primer consisting of SEQ ID NO 18;
an αWSα fluorescent normal probe comprising an oligonucleotide consisting of SEQ ID NO 23 and a fluorescent label; and
an αWSα fluorescent mutant probe comprising an oligonucleotide consisting of SEQ ID NO 24 and a fluorescent label.

15. The diagnostic kit of claim 1, further comprising:
another reagent mixture for detecting a β-thalassemia 41-42M deletion mutation genotype, comprising:
a 41-42M forward oligonucleotide primer consisting of SEQ ID NO 25;
a 41-42M reverse oligonucleotide primer consisting of SEQ ID NO 26;
a 41-42M fluorescent normal probe comprising an oligonucleotide consisting of SEQ ID NO 59 and a fluorescent label; and
a 41-42M fluorescent mutant probe comprising an oligonucleotide consisting of SEQ ID NO 60 and a fluorescent label.

16. The diagnostic kit of claim 1, further comprising:
another reagent mixture for detecting a β-thalassemia −28M mutation genotype, comprising:
a −28M forward oligonucleotide primer consisting of SEQ ID NO 27;
a −28M reverse oligonucleotide primer consisting of SEQ ID NO 28;
a −28M fluorescent normal probe comprising an oligonucleotide consisting of SEQ ID NO 61 and a fluorescent label; and
a −28M fluorescent mutant probe comprising an oligonucleotide consisting of SEQ ID NO 62 and a fluorescent label.

17. The diagnostic kit of claim 1, further comprising:
another reagent mixture for detecting a β-thalassemia −29M mutation genotype, comprising:
a −29M forward oligonucleotide primer consisting of SEQ ID NO 55;
a −29M reverse oligonucleotide primer consisting of SEQ ID NO 56;
a −29M fluorescent normal probe comprising an oligonucleotide consisting of SEQ ID NO 90 and a fluorescent label; and
a −29M fluorescent mutant probe comprising an oligonucleotide consisting of SEQ ID NO 91 and a fluorescent label.

18. The diagnostic kit of claim 1, further comprising:
another reagent mixture for detecting a β-thalassemia 17M mutation genotype, comprising:
a 17M forward oligonucleotide primer consisting of SEQ ID NO 31;
a 17M reverse oligonucleotide primer consisting of SEQ ID NO 32;
a 17M fluorescent normal probe comprising an oligonucleotide consisting of SEQ ID NO 65 and a fluorescent label; and
a 17M fluorescent mutant probe comprising an oligonucleotide consisting of SEQ ID NO 66 and a fluorescent label.

19. The diagnostic kit of claim 1, further comprising:
another reagent mixture for detecting a β-thalassemia mutation genotype, comprising:
a forward oligonucleotide primer selected from the group consisting of a 71-72 forward oligonucleotide primer consisting of SEQ ID NO 29, a 31M forward oligonucleotide primer consisting of SEQ ID NO 37, a CAPM forward oligonucleotide primer consisting of SEQ ID NO 49, a −30M forward oligonucleotide primer consisting of SEQ ID NO 53, a −32M forward oligonucleotide primer consisting of SEQ ID NO 57, a 43M forward oligonucleotide primer consisting of SEQ ID NO 41, a 90M forward oligonucleotide primer consisting of SEQ ID NO 96, a 654M forward oligonucleotide primer consisting of SEQ ID NO 35, an IVS-I-1M forward oligonucleotide primer consisting of SEQ ID NO 45, an IVS-I-5M forward oligonucleotide primer consisting of SEQ ID NO 47, an IVS-II-5M forward oligonucleotide primer consisting of SEQ ID NO 98, a CD37M forward oligonucleotide primer consisting of SEQ ID NO 94, a 14-15M forward oligonucleotide primer consisting of SEQ ID NO 39, a 27/28M forward oligonucleotide primer consisting of SEQ ID NO 43, a βEM forward oligonucleotide primer consisting of SEQ ID NO 33, and an IntM forward oligonucleotide primer consisting of SEQ ID NO 51;
a reverse oligonucleotide primer selected from the group consisting of a 71-72 reverse oligonucleotide primer consisting of SEQ ID NO 30, a 31M reverse oligonucleotide primer consisting of SEQ ID NO 37, a CAPM reverse oligonucleotide primer consisting of SEQ ID NO 50, a −30M reverse oligonucleotide primer consisting of SEQ ID NO 54, a −32M reverse oligonucleotide primer consisting of SEQ ID NO 58, a 43M reverse oligonucleotide primer consisting of SEQ ID NO 42, a 90M reverse oligonucleotide primer consisting of SEQ ID NO 97, a 654M reverse oligonucleotide primer consisting of SEQ ID NO 36, an IVS-I-1M reverse oligonucleotide primer consisting of SEQ ID NO 46, an IVS-I-5M reverse oligonucleotide primer consisting of SEQ ID NO 48, an IVS-II-5M reverse oligonucleotide primer consisting of SEQ ID NO 99, a CD37M reverse oligonucleotide primer consisting of SEQ ID NO 95, a 14-15M reverse oligonucleotide primer consisting of SEQ ID NO 40, a 27/28M reverse oligonucleotide primer consisting of SEQ ID NO 44, a βEM reverse oligonucleotide primer consisting of SEQ ID NO 34, and an IntM reverse oligonucleotide primer consisting of SEQ ID NO 52;

a fluorescent normal probe selected from the group consisting of a 71-72 fluorescent normal probe comprising an oligonucleotide consisting of SEQ ID NO 63 and a fluorescent label, a 31M fluorescent normal probe comprising an oligonucleotide consisting of SEQ ID NO 37 and a fluorescent label a CAPM fluorescent normal probe comprising an oligonucleotide consisting of SEQ ID NO 84 and a fluorescent label a −30M fluorescent normal probe comprising an oligonucleotide consisting of SEQ ID NO 88 and a fluorescent label a −32M fluorescent normal probe comprising an oligonucleotide consisting of SEQ ID NO 92 and a fluorescent label a 43M fluorescent normal probe comprising an oligonucleotide consisting of SEQ ID NO 75 and a fluorescent label a 90M fluorescent normal probe comprising an oligonucleotide consisting of SEQ ID NO 105 and a fluorescent label a 654M fluorescent normal probe comprising an oligonucleotide consisting of SEQ ID NO 69 and a fluorescent label, an IVS-I-1M fluorescent normal probe comprising an oligonucleotide consisting of SEQ ID NO 79 and a fluorescent label, an IVS-I-5M fluorescent normal probe comprising an oligonucleotide consisting of SEQ ID NO 82 and a fluorescent label an IVS-II-5M fluorescent normal probe comprising an oligonucleotide consisting of SEQ ID NO 107 and a fluorescent label, a CD37M fluorescent normal probe comprising an oligonucleotide consisting of SEQ ID NO 103 and a fluorescent label, a 14-15M fluorescent normal probe comprising an oligonucleotide consisting of SEQ ID NO 73 and a fluorescent label a 27/28M fluorescent normal probe comprising an oligonucleotide consisting of SEQ ID NO 77 and a fluorescent label a βEM fluorescent normal probe comprising an oligonucleotide consisting of SEQ ID NO 67 and a fluorescent label, and an IntM fluorescent normal probe comprising an oligonucleotide consisting of SEQ ID NO 86 and a fluorescent label; and one or more fluorescent mutant probes selected from the group consisting of a 71-72 fluorescent mutant probe comprising an oligonucleotide consisting of SEQ ID NO 64 and a fluorescent label, a 31M fluorescent mutant probe comprising an oligonucleotide consisting of SEQ ID NO 37 and a fluorescent label, a CAPM fluorescent mutant probe comprising an oligonucleotide consisting of SEQ ID NO 85 and a fluorescent label, a −30M fluorescent mutant probe comprising an oligonucleotide consisting of SEQ ID NO 89 and a fluorescent label a −32M fluorescent mutant probe comprising an oligonucleotide consisting of SEQ ID NO 93 and a fluorescent label a 43M fluorescent mutant probe comprising an oligonucleotide consisting of SEQ ID NO 76 and a fluorescent label a 90M fluorescent mutant probe comprising an oligonucleotide consisting of SEQ ID NO 104 and a fluorescent label a 654M fluorescent mutant probe comprising an oligonucleotide consisting of SEQ ID NO 70 and a fluorescent label a first IVS-I-1M fluorescent mutant probe comprising an oligonucleotide consisting of SEQ ID NO 80 and a fluorescent label, a second IVS-I-1M fluorescent mutant probe comprising an oligonucleotide consisting of SEQ ID NO 81 and a fluorescent label, an IVS-I-5M fluorescent mutant probe comprising an oligonucleotide consisting of SEQ ID NO 83 and a fluorescent label an IVS-II-5M fluorescent mutant probe comprising an oligonucleotide consisting of SEQ ID NO 106 and a fluorescent label, a CD37M fluorescent mutant probe comprising an oligonucleotide consisting of SEQ ID NO 102 and a fluorescent label, a 14-15M fluorescent mutant probe comprising an oligonucleotide consisting of SEQ ID NO 74 and a fluorescent label a 27/28M fluorescent mutant probe comprising an oligonucleotide consisting of SEQ ID NO 78 and a fluorescent label a βEM fluorescent mutant probe comprising an oligonucleotide consisting of SEQ ID NO 68 and a fluorescent label, and an IntM fluorescent mutant probe comprising an oligonucleotide consisting of SEQ ID NO 87 and a fluorescent label.

* * * * *

SEQUENCE LISTING

<160> NUMBER OF SEQ ID NOS: 108

<210> SEQ ID NO 1
<211> LENGTH: 25
<212> TYPE: DNA
<213> ORGANISM: Homo sapiens

<400> SEQUENCE: 1
tgtgtgtact tgtgtgatgg ttaga                                    25

<210> SEQ ID NO 2
<211> LENGTH: 28
<212> TYPE: DNA
<213> ORGANISM: Homo sapiens

<400> SEQUENCE: 2
ctggttaaac aggtaaacaa agcaatag                                 28

<210> SEQ ID NO 3
<211> LENGTH: 18
<212> TYPE: DNA
<213> ORGANISM: Homo sapiens

-continued

```
<400> SEQUENCE: 3
tccttgcacc ggcccttc                                                    18

<210> SEQ ID NO 4
<211> LENGTH: 22
<212> TYPE: DNA
<213> ORGANISM: Homo sapiens

<400> SEQUENCE: 4
gtccttggtc tgagacaggt aa                                               22

<210> SEQ ID NO 5
<211> LENGTH: 28
<212> TYPE: DNA
<213> ORGANISM: Homo sapiens

<400> SEQUENCE: 5
tgcctacctc ccagaggagg ttgaatgc                                         28

<210> SEQ ID NO 6
<211> LENGTH: 31
<212> TYPE: DNA
<213> ORGANISM: Homo sapiens

<400> SEQUENCE: 6
tgaataaagt ctgagtgggc agcagcctgt g                                     31

<210> SEQ ID NO 7
<211> LENGTH: 20
<212> TYPE: DNA
<213> ORGANISM: Homo sapiens

<400> SEQUENCE: 7
gattgccaca gcctgctgct                                                  20

<210> SEQ ID NO 8
<211> LENGTH: 21
<212> TYPE: DNA
<213> ORGANISM: Homo sapiens

<400> SEQUENCE: 8
agggctcatt acatgtggac c                                                21

<210> SEQ ID NO 9
<211> LENGTH: 29
<212> TYPE: DNA
<213> ORGANISM: Homo sapiens

<400> SEQUENCE: 9
ccagacatcc tccatgtgag aagcagcga                                        29

<210> SEQ ID NO 10
<211> LENGTH: 23
<212> TYPE: DNA
<213> ORGANISM: Homo sapiens

<400> SEQUENCE: 10
ctctgtgttc tcagtattgg agg                                              23

<210> SEQ ID NO 11
<211> LENGTH: 22
<212> TYPE: DNA
```

<213> ORGANISM: Homo sapiens

<400> SEQUENCE: 11
gagtgcagtg ttgtagtcat gg                                    22

<210> SEQ ID NO 12
<211> LENGTH: 26
<212> TYPE: DNA
<213> ORGANISM: Homo sapiens

<400> SEQUENCE: 12
aggggagaag ctgagtgatg ggtccg                                26

<210> SEQ ID NO 13
<211> LENGTH: 21
<212> TYPE: DNA
<213> ORGANISM: Homo sapiens

<400> SEQUENCE: 13
ctggacaagt tcctggcttc t                                     21

<210> SEQ ID NO 14
<211> LENGTH: 18
<212> TYPE: DNA
<213> ORGANISM: Homo sapiens

<400> SEQUENCE: 14
gtgcaaggag gggaggag                                         18

<210> SEQ ID NO 15
<211> LENGTH: 18
<212> TYPE: DNA
<213> ORGANISM: Homo sapiens

<400> SEQUENCE: 15
acctccccgc cgagttca                                         18

<210> SEQ ID NO 16
<211> LENGTH: 21
<212> TYPE: DNA
<213> ORGANISM: Homo sapiens

<400> SEQUENCE: 16
gaggctccag cttaacggta t                                     21

<210> SEQ ID NO 17
<211> LENGTH: 18
<212> TYPE: DNA
<213> ORGANISM: Homo sapiens

<400> SEQUENCE: 17
acctccccgc cgagttca                                         18

<210> SEQ ID NO 18
<211> LENGTH: 21
<212> TYPE: DNA
<213> ORGANISM: Homo sapiens

<400> SEQUENCE: 18
gaggctccag cttaacggta t                                     21

<210> SEQ ID NO 19
<211> LENGTH: 30

```
<212> TYPE: DNA
<213> ORGANISM: Homo sapiens

<400> SEQUENCE: 19
caccgtgctg acctccaaat accgttaagc                                          30

<210> SEQ ID NO 20
<211> LENGTH: 30
<212> TYPE: DNA
<213> ORGANISM: Homo sapiens

<400> SEQUENCE: 20
caccgtgctg acctccaaat accgtcaagc                                          30

<210> SEQ ID NO 21
<211> LENGTH: 22
<212> TYPE: DNA
<213> ORGANISM: Homo sapiens

<400> SEQUENCE: 21
ctgcggtgca cgcctccctg ga                                                  22

<210> SEQ ID NO 22
<211> LENGTH: 22
<212> TYPE: DNA
<213> ORGANISM: Homo sapiens

<400> SEQUENCE: 22
ctgcggtgca cgcctccccg ga                                                  22

<210> SEQ ID NO 23
<211> LENGTH: 22
<212> TYPE: DNA
<213> ORGANISM: Homo sapiens

<400> SEQUENCE: 23
ctgcggtgca cgcctccctg ga                                                  22

<210> SEQ ID NO 24
<211> LENGTH: 22
<212> TYPE: DNA
<213> ORGANISM: Homo sapiens

<400> SEQUENCE: 24
ctgcggtgca ggcctccctg ga                                                  22

<210> SEQ ID NO 25
<211> LENGTH: 21
<212> TYPE: DNA
<213> ORGANISM: Homo sapiens

<400> SEQUENCE: 25
cttaggctgc tggtggtcta c                                                   21

<210> SEQ ID NO 26
<211> LENGTH: 22
<212> TYPE: DNA
<213> ORGANISM: Homo sapiens

<400> SEQUENCE: 26
cagcatcagg agtggacaga tc                                                  22

<210> SEQ ID NO 27
```

```
<211> LENGTH: 16
<212> TYPE: DNA
<213> ORGANISM: Homo sapiens

<400> SEQUENCE: 27
gcagggaggg caggag                                                    16

<210> SEQ ID NO 28
<211> LENGTH: 25
<212> TYPE: DNA
<213> ORGANISM: Homo sapiens

<400> SEQUENCE: 28
gttgtgtcag aagcaaatgt aagca                                          25

<210> SEQ ID NO 29
<211> LENGTH: 21
<212> TYPE: DNA
<213> ORGANISM: Homo sapiens

<400> SEQUENCE: 29
aaggctcatg gcaagaaagt g                                              21

<210> SEQ ID NO 30
<211> LENGTH: 21
<212> TYPE: DNA
<213> ORGANISM: Homo sapiens

<400> SEQUENCE: 30
aaaggtgccc ttgaggttgt c                                              21

<210> SEQ ID NO 31
<211> LENGTH: 22
<212> TYPE: DNA
<213> ORGANISM: Homo sapiens

<400> SEQUENCE: 31
gaggagaagt ctgccgttac tg                                             22

<210> SEQ ID NO 32
<211> LENGTH: 20
<212> TYPE: DNA
<213> ORGANISM: Homo sapiens

<400> SEQUENCE: 32
ggcctcacca ccaacttcat                                                20

<210> SEQ ID NO 33
<211> LENGTH: 21
<212> TYPE: DNA
<213> ORGANISM: Homo sapiens

<400> SEQUENCE: 33
gcaaggtgaa cgtggatgaa g                                              21

<210> SEQ ID NO 34
<211> LENGTH: 26
<212> TYPE: DNA
<213> ORGANISM: Homo sapiens

<400> SEQUENCE: 34
gtctccttaa acctgtcttg taacct                                         26
```

```
<210> SEQ ID NO 35
<211> LENGTH: 25
<212> TYPE: DNA
<213> ORGANISM: Homo sapiens

<400> SEQUENCE: 35
tgcctctttg caccattcta aagaa                                      25

<210> SEQ ID NO 36
<211> LENGTH: 34
<212> TYPE: DNA
<213> ORGANISM: Homo sapiens

<400> SEQUENCE: 36
aacctcttac atcagttaca atttatatgc agaa                            34

<210> SEQ ID NO 37
<211> LENGTH: 23
<212> TYPE: DNA
<213> ORGANISM: Homo sapiens

<400> SEQUENCE: 37
actgactctc tctgcctatt ggt                                        23

<210> SEQ ID NO 38
<211> LENGTH: 20
<212> TYPE: DNA
<213> ORGANISM: Homo sapiens

<400> SEQUENCE: 38
cctctgggtc caagggtaga                                            20

<210> SEQ ID NO 39
<211> LENGTH: 24
<212> TYPE: DNA
<213> ORGANISM: Homo sapiens

<400> SEQUENCE: 39
ctagcaacct caaacagaca ccat                                       24

<210> SEQ ID NO 40
<211> LENGTH: 21
<212> TYPE: DNA
<213> ORGANISM: Homo sapiens

<400> SEQUENCE: 40
caccaacttc atccacgttc a                                          21

<210> SEQ ID NO 41
<211> LENGTH: 21
<212> TYPE: DNA
<213> ORGANISM: Homo sapiens

<400> SEQUENCE: 41
cttaggctgc tggtggtcta c                                          21

<210> SEQ ID NO 42
<211> LENGTH: 22
<212> TYPE: DNA
<213> ORGANISM: Homo sapiens

<400> SEQUENCE: 42
cagcatcagg agtggacaga tc                                         22
```

```
<210> SEQ ID NO 43
<211> LENGTH: 22
<212> TYPE: DNA
<213> ORGANISM: Homo sapiens

<400> SEQUENCE: 43
ggtgaacgtg gatgaagttg gt                                             22

<210> SEQ ID NO 44
<211> LENGTH: 26
<212> TYPE: DNA
<213> ORGANISM: Homo sapiens

<400> SEQUENCE: 44
gtctccttaa acctgtcttg taacct                                         26

<210> SEQ ID NO 45
<211> LENGTH: 22
<212> TYPE: DNA
<213> ORGANISM: Homo sapiens

<400> SEQUENCE: 45
ggtgaacgtg gatgaagttg gt                                             22

<210> SEQ ID NO 46
<211> LENGTH: 25
<212> TYPE: DNA
<213> ORGANISM: Homo sapiens

<400> SEQUENCE: 46
gcccagtttc tattggtctc cttaa                                          25

<210> SEQ ID NO 47
<211> LENGTH: 22
<212> TYPE: DNA
<213> ORGANISM: Homo sapiens

<400> SEQUENCE: 47
ggtgaacgtg gatgaagttg gt                                             22

<210> SEQ ID NO 48
<211> LENGTH: 25
<212> TYPE: DNA
<213> ORGANISM: Homo sapiens

<400> SEQUENCE: 48
gcccagtttc tattggtctc cttaa                                          25

<210> SEQ ID NO 49
<211> LENGTH: 25
<212> TYPE: DNA
<213> ORGANISM: Homo sapiens

<400> SEQUENCE: 49
gcttacattt gcttctgaca caact                                          25

<210> SEQ ID NO 50
<211> LENGTH: 21
<212> TYPE: DNA
<213> ORGANISM: Homo sapiens

<400> SEQUENCE: 50
ctcaggagtc agatgcacca t                                              21
```

<210> SEQ ID NO 51
<211> LENGTH: 24
<212> TYPE: DNA
<213> ORGANISM: Homo sapiens

<400> SEQUENCE: 51
ctgtgttcac tagcaacctc aaac                                    24

<210> SEQ ID NO 52
<211> LENGTH: 21
<212> TYPE: DNA
<213> ORGANISM: Homo sapiens

<400> SEQUENCE: 52
ggcagtaacg gcagacttct c                                       21

<210> SEQ ID NO 53
<211> LENGTH: 16
<212> TYPE: DNA
<213> ORGANISM: Homo sapiens

<400> SEQUENCE: 53
gcagggaggg caggag                                             16

<210> SEQ ID NO 54
<211> LENGTH: 25
<212> TYPE: DNA
<213> ORGANISM: Homo sapiens

<400> SEQUENCE: 54
gttgtgtcag aagcaaatgt aagca                                   25

<210> SEQ ID NO 55
<211> LENGTH: 16
<212> TYPE: DNA
<213> ORGANISM: Homo sapiens

<400> SEQUENCE: 55
gcagggaggg caggag                                             16

<210> SEQ ID NO 56
<211> LENGTH: 25
<212> TYPE: DNA
<213> ORGANISM: Homo sapiens

<400> SEQUENCE: 56
gttgtgtcag aagcaaatgt aagca                                   25

<210> SEQ ID NO 57
<211> LENGTH: 16
<212> TYPE: DNA
<213> ORGANISM: Homo sapiens

<400> SEQUENCE: 57
gcagggaggg caggag                                             16

<210> SEQ ID NO 58
<211> LENGTH: 25
<212> TYPE: DNA
<213> ORGANISM: Homo sapiens

<400> SEQUENCE: 58
gttgtgtcag aagcaaatgt aagca 25

<210> SEQ ID NO 59
<211> LENGTH: 18
<212> TYPE: DNA
<213> ORGANISM: Homo sapiens

<400> SEQUENCE: 59
aggactcaaa gaacctct 18

<210> SEQ ID NO 60
<211> LENGTH: 17
<212> TYPE: DNA
<213> ORGANISM: Homo sapiens

<400> SEQUENCE: 60
caaaggactc aacctct 17

<210> SEQ ID NO 61
<211> LENGTH: 17
<212> TYPE: DNA
<213> ORGANISM: Homo sapiens

<400> SEQUENCE: 61
ccctgacttt tatgccc 17

<210> SEQ ID NO 62
<211> LENGTH: 16
<212> TYPE: DNA
<213> ORGANISM: Homo sapiens

<400> SEQUENCE: 62
cctgacttct atgccc 16

<210> SEQ ID NO 63
<211> LENGTH: 15
<212> TYPE: DNA
<213> ORGANISM: Homo sapiens

<400> SEQUENCE: 63 tcggtgccttt tagtg 15

<210> SEQ ID NO 64
<211> LENGTH: 15
<212> TYPE: DNA
<213> ORGANISM: Homo sapiens

<400> SEQUENCE: 64
cggtgccttt aagtg 15

<210> SEQ ID NO 65
<211> LENGTH: 18
<212> TYPE: DNA
<213> ORGANISM: Homo sapiens

<400> SEQUENCE: 65
cacgttcacc ttgcccca 18

<210> SEQ ID NO 66
<211> LENGTH: 17
<212> TYPE: DNA
<213> ORGANISM: Homo sapiens

<400> SEQUENCE: 66
acgttcacct agcccca                                              17

<210> SEQ ID NO 67
<211> LENGTH: 15
<212> TYPE: DNA
<213> ORGANISM: Homo sapiens

<400> SEQUENCE: 67
tggtggtgag gccct                                                15

<210> SEQ ID NO 68
<211> LENGTH: 16
<212> TYPE: DNA
<213> ORGANISM: Homo sapiens

<400> SEQUENCE: 68
ttggtggtaa ggccct                                               16

<210> SEQ ID NO 69
<211> LENGTH: 21
<212> TYPE: DNA
<213> ORGANISM: Homo sapiens

<400> SEQUENCE: 69
agatattgct attgccttaa c                                         21

<210> SEQ ID NO 70
<211> LENGTH: 21
<212> TYPE: DNA
<213> ORGANISM: Homo sapiens

<400> SEQUENCE: 70
agatattgct attaccttaa c                                         21

<210> SEQ ID NO 71
<211> LENGTH: 15
<212> TYPE: DNA
<213> ORGANISM: Homo sapiens

<400> SEQUENCE: 71
caccagcagc ctaag                                                15

<210> SEQ ID NO 72
<211> LENGTH: 15
<212> TYPE: DNA
<213> ORGANISM: Homo sapiens

<400> SEQUENCE: 72
ccaccagcac ctaag                                                15

<210> SEQ ID NO 73
<211> LENGTH: 16
<212> TYPE: DNA
<213> ORGANISM: Homo sapiens

<400> SEQUENCE: 73
cgttactgcc ctgtgg                                               16

<210> SEQ ID NO 74
<211> LENGTH: 16
<212> TYPE: DNA
<213> ORGANISM: Homo sapiens

```
<400> SEQUENCE: 74
cgttactgcc ctggtg                                              16

<210> SEQ ID NO 75
<211> LENGTH: 19
<212> TYPE: DNA
<213> ORGANISM: Homo sapiens

<400> SEQUENCE: 75
agaggttctt tgagtcctt                                           19

<210> SEQ ID NO 76
<211> LENGTH: 20
<212> TYPE: DNA
<213> ORGANISM: Homo sapiens

<400> SEQUENCE: 76
cagaggttct tttagtcctt                                          20

<210> SEQ ID NO 77
<211> LENGTH: 16
<212> TYPE: DNA
<213> ORGANISM: Homo sapiens

<400> SEQUENCE: 77
tgaggcccct gggcag                                              16

<210> SEQ ID NO 78
<211> LENGTH: 15
<212> TYPE: DNA
<213> ORGANISM: Homo sapiens

<400> SEQUENCE: 78
tgaggccctg ggcag                                               15

<210> SEQ ID NO 79
<211> LENGTH: 16
<212> TYPE: DNA
<213> ORGANISM: Homo sapiens

<400> SEQUENCE: 79
ctgggcaggt tggtat                                              16

<210> SEQ ID NO 80
<211> LENGTH: 16
<212> TYPE: DNA
<213> ORGANISM: Homo sapiens

<400> SEQUENCE: 80
ctgggcagat tggtat                                              16

<210> SEQ ID NO 81
<211> LENGTH: 16
<212> TYPE: DNA
<213> ORGANISM: Homo sapiens

<400> SEQUENCE: 81
ctgggcagtt tggtat                                              16

<210> SEQ ID NO 82
<211> LENGTH: 16
<212> TYPE: DNA
```

```
<400> SEQUENCE: 82
caggttggta tcaagg                                              16

<210> SEQ ID NO 83
<211> LENGTH: 16
<212> TYPE: DNA
<213> ORGANISM: Homo sapiens

<400> SEQUENCE: 83
caggttgcta tcaagg                                              16

<210> SEQ ID NO 84
<211> LENGTH: 18
<212> TYPE: DNA
<213> ORGANISM: Homo sapiens

<400> SEQUENCE: 84
caacctcaaa cagacacc                                            18

<210> SEQ ID NO 85
<211> LENGTH: 17
<212> TYPE: DNA
<213> ORGANISM: Homo sapiens

<400> SEQUENCE: 85
tagcaacctc agacacc                                             17

<210> SEQ ID NO 86
<211> LENGTH: 17
<212> TYPE: DNA
<213> ORGANISM: Homo sapiens

<400> SEQUENCE: 86
tcaaacagac accatgg                                             17

<210> SEQ ID NO 87
<211> LENGTH: 17
<212> TYPE: DNA
<213> ORGANISM: Homo sapiens

<400> SEQUENCE: 87
tcaaacagac accaggg                                             17

<210> SEQ ID NO 88
<211> LENGTH: 19
<212> TYPE: DNA
<213> ORGANISM: Homo sapiens

<400> SEQUENCE: 88
ccctgacttt tatgcccag                                           19

<210> SEQ ID NO 89
<211> LENGTH: 18
<212> TYPE: DNA
<213> ORGANISM: Homo sapiens

<400> SEQUENCE: 89
cctgactttt gtgcccag                                            18

<210> SEQ ID NO 90
<211> LENGTH: 17
<212> TYPE: DNA
```

<213> ORGANISM: Homo sapiens

<400> SEQUENCE: 90 ccctgactttt tatgccc                                                     17

<210> SEQ ID NO 91
<211> LENGTH: 16
<212> TYPE: DNA
<213> ORGANISM: Homo sapiens

<400> SEQUENCE: 91
cctgactttc atgccc                                                       16

<210> SEQ ID NO 92
<211> LENGTH: 20
<212> TYPE: DNA
<213> ORGANISM: Homo sapiens

<400> SEQUENCE: 92
cctgactttt atgcccagcc                                                   20

<210> SEQ ID NO 93
<211> LENGTH: 21
<212> TYPE: DNA
<213> ORGANISM: Homo sapiens

<400> SEQUENCE: 93 ccctgactttt tattcccagc c                                                21

<210> SEQ ID NO 94
<211> LENGTH: 26
<212> TYPE: DNA
<213> ORGANISM: Homo sapiens

<400> SEQUENCE: 94
tctctctgcc tattggtcta ttttcc                                            26

<210> SEQ ID NO 95
<211> LENGTH: 22
<212> TYPE: DNA
<213> ORGANISM: Homo sapiens

<400> SEQUENCE: 95
gatccccaaa ggactcaaag aa                                                22

<210> SEQ ID NO 96
<211> LENGTH: 24
<212> TYPE: DNA
<213> ORGANISM: Homo sapiens

<400> SEQUENCE: 96
caggtacggc tgtcatcact taga                                              24

<210> SEQ ID NO 97
<211> LENGTH: 22
<212> TYPE: DNA
<213> ORGANISM: Homo sapiens

<400> SEQUENCE: 97
tagatggctc tgccctgact tt                                                22

<210> SEQ ID NO 98
<211> LENGTH: 20

```
<212> TYPE: DNA
<213> ORGANISM: Homo sapiens

<400> SEQUENCE: 98
ctggacaacc tcaagggcac                                               20

<210> SEQ ID NO 99
<211> LENGTH: 22
<212> TYPE: DNA
<213> ORGANISM: Homo sapiens

<400> SEQUENCE: 99
aaagaaaaca tcaagggtcc ca                                            22

<210> SEQ ID NO 100
<211> LENGTH: 23
<212> TYPE: DNA
<213> ORGANISM: Homo sapiens

<400> SEQUENCE: 100
tgactgcatc ataattccag cag                                           23

<210> SEQ ID NO 101
<211> LENGTH: 21
<212> TYPE: DNA
<213> ORGANISM: Homo sapiens

<400> SEQUENCE: 101
caagtgggct gagcccttga g                                             21

<210> SEQ ID NO 102
<211> LENGTH: 16
<212> TYPE: DNA
<213> ORGANISM: Homo sapiens

<400> SEQUENCE: 102
tggtctaccc ttagac                                                   16

<210> SEQ ID NO 103
<211> LENGTH: 16
<212> TYPE: DNA
<213> ORGANISM: Homo sapiens

<400> SEQUENCE: 103
tggtctaccc ttggac                                                   16

<210> SEQ ID NO 104
<211> LENGTH: 14
<212> TYPE: DNA
<213> ORGANISM: Homo sapiens

<400> SEQUENCE: 104
tggagccata ccct                                                     14

<210> SEQ ID NO 105
<211> LENGTH: 14
<212> TYPE: DNA
<213> ORGANISM: Homo sapiens

<400> SEQUENCE: 105
tggagccaca ccct                                                     14

<210> SEQ ID NO 106
```

```
<211> LENGTH: 16
<212> TYPE: DNA
<213> ORGANISM: Homo sapiens

<400> SEQUENCE: 106
acttcagggt gactct                                                        16

<210> SEQ ID NO 107
<211> LENGTH: 17
<212> TYPE: DNA
<213> ORGANISM: Homo sapiens

<400> SEQUENCE: 107
aacttcaggg tgagtct                                                       17

<210> SEQ ID NO 108
<211> LENGTH: 34
<212> TYPE: DNA
<213> ORGANISM: Homo sapiens

<400> SEQUENCE: 108
aggaagaata aagcgagagg aatcacattc ctca                                    34
```